United States Patent
Tarazanova et al.

(10) Patent No.: US 11,066,639 B2
(45) Date of Patent: Jul. 20, 2021

(54) METHOD FOR THE PRODUCTION OF A DAIRY FOOD PRODUCT AND A METHOD FOR GENE TRANSFER BY CONJUGATION

(71) Applicant: DSM IP ASSETS B.V., Heerlen (NL)

(72) Inventors: Mariya Alexeevna Tarazanova, Zwolle (NL); Thom Huppertz, Ede (NL); Herwig Bachmann, Amsterdam (NL); Jan Kok, Groningen (NL); Marke Beerthuyzen, Ede (NL)

(73) Assignee: DSM IP ASSETS B.V., Heerlen (NL)

( * ) Notice: Subject to any disclaimer, the term of this patent is extended or adjusted under 35 U.S.C. 154(b) by 200 days.

(21) Appl. No.: 16/084,591

(22) PCT Filed: Mar. 16, 2016

(86) PCT No.: PCT/EP2016/055676
§ 371 (c)(1),
(2) Date: Sep. 13, 2018

(87) PCT Pub. No.: WO2017/157430
PCT Pub. Date: Sep. 21, 2017

(65) Prior Publication Data
US 2020/0253229 A1     Aug. 13, 2020

(51) Int. Cl.
| | | |
|---|---|---|
| *C12N 1/20* | (2006.01) | |
| *A23C 9/123* | (2006.01) | |
| *A23L 33/135* | (2016.01) | |
| *C07K 14/195* | (2006.01) | |
| *C12R 1/46* | (2006.01) | |
| *C07K 14/315* | (2006.01) | |

(52) U.S. Cl.
CPC .............. *C12N 1/20* (2013.01); *A23C 9/1236* (2013.01); *A23L 33/135* (2016.08); *C07K 14/195* (2013.01); *C07K 14/315* (2013.01); *C12R 1/46* (2013.01); *A23V 2002/00* (2013.01); *A23Y 2220/23* (2013.01); *A23Y 2220/49* (2013.01); *A23Y 2240/75* (2013.01)

(58) Field of Classification Search
None
See application file for complete search history.

(56) References Cited

PUBLICATIONS

Rhee et al., "Effect of Environmental pH on Chain Length of Lactobacillus bulgaricus", Journal of Bacteriology, vol. 144, pp. 865-868 (Year: 1980).*
"Handbook of Dairy Foods Analysis", edited by Leo M.L. Nollet and Fidel Todra, 2010, p. 473, CRC Press.
Gasson, M.J., "Plasmid Complements of *Streptococcus Lactis* NCDO 712 and Other Latic Streptococci After Protoplast-Induced Curing," Journal of Bacteriology, American Society for Microbiology, US, vol. 154, No. 1, Apr. 1, 1983, pp. 1-09, XP000983104.
Meyrand, Mickael et al., "Surface Proteome Analysis of a Natural Isolate of Lactococcus lactis Reveals the Presence of Pili Able to Bind Human Intestinal Epithelial Cells," Molecular & Cellular Proteomics, vol. 12, No. 12, Dec. 2013, pp. 3935-3947, XP002757685.
Oxaran, Virginie et al., "Pilus Biogenesis in Lactococcus lactis: Molecular Characterization and Role in Aggregation and Biofilm Formation," PLOS ONE, vol. 7, No. 12, Dec. 2012, pp. 1-18, XP002757686.
Reunanen J. et al., "Characterization of the SpaCBA pilus fibers in the probiotic Lactobacillus rhamnosus GG," Applied and Environmental Microbiology Apr. 2012 American Society for Microbiology USA, vol. 78, No. 7, Apr. 2012, pp. 2337-2344, XP002757687.
International Search Report in corresponding application No. PCT/EP2016/055676 dated May 30, 2016.

* cited by examiner

*Primary Examiner* — Michelle F. Paguio Frising
(74) *Attorney, Agent, or Firm* — McBee Moore & Vanik IP, LLC

(57) ABSTRACT

The present invention relates to the field of microbiology, specifically the field of production of a dairy food product using fermentation and the field of gene transfer by conjugation.

Figure 1:
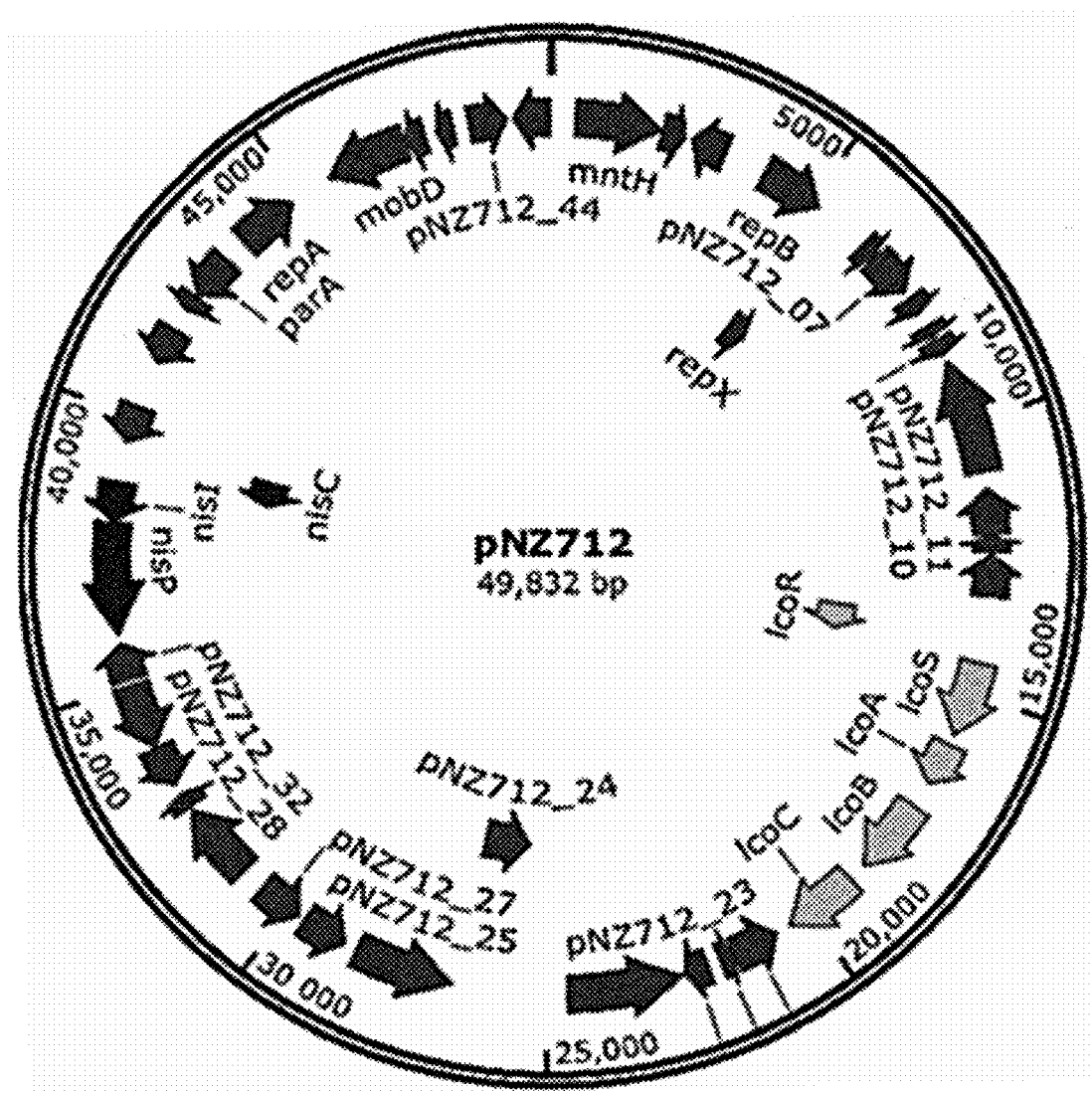

15 Claims, 8 Drawing Sheets
Specification includes a Sequence Listing.

METHOD FOR THE PRODUCTION OF A DAIRY FOOD PRODUCT AND A METHOD FOR GENE TRANSFER BY CONJUGATION

CROSS REFERENCE TO RELATED APPLICATIONS

This application is a National Stage entry of International Application No. PCT/EP2016/055676 filed 16 Mar. 2016. The contents of the aforementioned application is incorporated herein by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing 2919208-481000_ST25.txt" created on 30 Aug. 2018, and 11,809 bytes in size) is submitted concurrently with the instant application, and the entire contents of the Sequence Listing are incorporated herein by reference.

FIELD OF THE INVENTION

The present invention relates to the field of microbiology, specifically the field of production of a dairy food product using fermentation and the field of gene transfer by conjugation.

DESCRIPTION OF RELATED ART

Lactic acid bacteria (LAB) are gram-positive bacteria that are generally regarded as safe and they are used extensively in food and feed fermentations. They are also found on mucosal surfaces of humans and animals (34, 37). One of the dominant features during fermentation processes with LABs is that they produce lactic acid as the main metabolic end product and this leads to rapid acidification and hence preservation of the fermented material. An additional functionality of many strains is the production of volatile metabolites that are important flavour compounds (51-53). In fermentation the bacteria can also play a significant role in altering textural properties of the material through e.g. proteolytic activity or the production of extracellular polysaccharides (50).

In general the structure of fermented dairy products is very complex, consisting of caseins, whey proteins, fat droplets, serum or whey pockets, minerals, salts and microorganisms. Herein, we refer to such structure as the matrix. In such a matrix interactions between milk components and their functionality are studied extensively (14, 24, 31, 35, 46). For example, the rheological properties of a milk gel depend on the size and number of fat droplets and the nature of available emulsifiers (43). If the matrix is stabilized by low molecular weight surfactants, then the milk gel is weak and has a high meltability, the extent to which gel flows and spreads upon heating, because the surface of fat droplets is smooth and non-interactive. However, if fat droplets are stabilized by whey proteins, then the milk gel is strong and has a low meltability because protein-protein cross-linking interactions are formed between emulsified fat droplets. Other interactions in the food matrix can be hydrophobic (30), electrostatic (11), hydrogen bonding (64), Van der Waals, depletion interaction (59), steric repulsion (16) and salt bridges (5).

In contrast to interactions between the milk components themselves very little is known about so called microbematrix interactions which describe the interaction between lactic acid bacteria and matrix components of the fermented products (7-10, 47).

Interactions between microorganisms and milk components occur via surface properties of both particles. Bacteria as well as matrix components have a charge and hydrophobicity. The surface properties of bacteria are determined by molecular composition of its cell wall, which can be decorated with (lipo-) teichoic acids, proteins, pili, or (exo/capsular)polysaccharides (EPS/CPS) (13, 22, 45). The molecular composition of the cell wall has a significant impact on the roughness of the bacterial surface, on bacterial chaining and on cell aggregation. These properties govern the interactions between bacteria and the food matrix (7, 41). A well-studied example of a change in textural properties is the production of EPS by the bacterial culture used for the fermentation. EPS are hydrocolloids that can bind high amounts of water, increasing water holding capacity in protein-free pores of the fermented milk matrix. This leads to an increase in milk viscosity and it reduces syneresis (2, 26, 48). Additionally, the charge, stiffness and linearity of EPS molecules impact on rheological and physical properties of the fermented milk matrix. EPS modification by partial removal of side groups leads to its reduced efficiency as thickener (58).

Besides the role of EPS on textural properties of fermented milk little is known about the influence of bacterial surface properties on interactions with the matrix and its functional consequences on flavour and texture.

SUMMARY

In an aspect, the invention provides for a dairy bacterial strain with clumping and/or chaining properties, preferably when cultured under liquid conditions, preferably without a substantial amount of a clumping agent, wherein the clumping property results in clumps of at least 20 bacteria per average clump and wherein the chaining property results in chains of at least 8 bacteria per average chain.

In a further aspect, the invention provides for a method for the production of a dairy bacterial strain according to the invention, comprising:
  culturing a precursor dairy bacterial strain under conditions that are conducive to the development of clumping and/or chaining properties and, optionally, isolating a dairy bacterial strain according to the invention.

In a further aspect, the invention provides for a dairy bacterial strain obtainable by a method according to the invention.

In a further aspect, the invention provides for a composition comprising a dairy bacterial strain according to the invention.

In a further aspect, the invention provides for a method for the production of a food product, preferably a dairy food product, more preferably a fermented milk product, from a precursor food product comprising inoculating the precursor food product with a strain according to the invention or with a composition according to the invention and incubating the inoculated precursor food product.

In a further aspect, the invention provides for a food product, preferably a dairy food product, obtainable by the method according to the invention.

In a further aspect, the invention provides for a food product, preferably a dairy food product, comprising a dairy bacterial strain according to the invention.

In a further aspect, the invention provides for the use of a dairy bacterial strain according to the invention, or of a composition according to the invention for the preparation of a food product, preferably a dairy food product.

In a further aspect, the invention provides for a bacterial strain comprising an increased amount of expression product of a pilin gene cluster, wherein the amount of expression product is increased in view of *Lactococcus lactis* subsp *cremoris* NCDO712.

In a further aspect, the invention provides for a method for gene transfer by conjugation comprising, providing a composition comprising at least one bacterial strain according to the invention and incubating the composition under conditions conducive to conjugation.

In a further aspect, the invention provides for a method for the production of a desired bacterial strain comprising a genetic trait of interest, comprising providing a composition comprising:
  a precursor of the desired bacterial strain, wherein the precursor lacks the genetic trait of interest, and
  a donor bacterial strain comprising the genetic trait of interest, incubating the composition under conditions conducive to conjugation, and optionally isolating the desired bacterial strain comprising the genetic trait of interest, wherein at least one bacterial strain in the composition comprises a pilin gene cluster.

In a further aspect, the invention provides for a bacterial strain comprising a genetic trait of interest obtainable by a method according to the invention

DETAILED DESCRIPTION OF A PREFERRED EMBODIMENT

The present inventors have found a novel gene cluster that encodes pilin structures. These pilin structures surprisingly enhance conjugation efficiency and provide texturing properties to the bacteria expressing the pili gene cluster. Accordingly, in a first aspect the present invention provides for a dairy bacterial strain with clumping and/or chaining properties, preferably when cultured under liquid conditions, preferably without substantial amounts of a clumping agent, wherein the clumping property results in clumps of at least 20 bacteria per average clump and wherein the chaining property results in chains of at least 8 bacteria per average chain. Said bacterial strain is herein referred to as a dairy bacterial strain or a bacterial strain according to the invention; individual bacteria from such strain are herein referred to as bacteria according to the invention.

The term "dairy bacterial strain" is herein defined as any bacterial strain that is suitable for use in a dairy product and/or in the production of a dairy product. Dairy products are known to the person skilled in the art; preferred dairy products are the dairy products described elsewhere herein. The terms "culturing" and "fermenting" are herein used interchangeably. The term "clumping" is herein defined as the aggregation under liquid conditions of bacteria according to the invention into a single aggregate or clump (said terms are used interchangeably herein) comprising twenty bacteria or more. Preferably, the average aggregate or clump comprises at least 20, at least 25, 30, 35, 40, 45, 50, 55, 60, 65, 70, 75, 80, 85, 90, 95, or at least 100 bacteria according to the invention. Preferably, the average aggregate or clump comprises between 20 and 100 bacteria according to the invention, more preferably between 40 and 60 bacteria according to the invention. The term "chaining" is herein defined as the arrangement of a number of bacterial cells according to the invention into a chain or chord-like structure. Preferably, the average chain comprises at least 8, at least 9, 10, 11, 12, 13, 14, 15, 20, 25, 30, 35, 40, 45, 50, 60, 70, 80, 90, or at least 100 bacteria according to the invention. Preferably, the average chain comprises between 8 and 60 bacteria according to the invention. Preferably, at least 10%, at least 20%, 30%, 40%, 50%, 60%, 70%, 80%, 90%, or at least 95% of the bacteria according to the invention are part of a clump or chain. In the invention, the clumping and/or chaining properties of the bacteria according to the invention are intrinsic properties of a bacterial strain according to the invention; said properties are present without the induction by an external agent. An external clumping agent is ethanol or salts such as ammonium sulfate. The term "without substantial amounts of a clumping agent" means that such agent is not present in an amount that would induce clumping of bacteria according to the invention. Preferably, less than 10%, less than 5%, 4%, 3%, 2%, 1%, 0.5%, or most preferably less than 0.1% of clumping agent is present. In case of ethanol, preferably less than 5%, less than 4%, 3%, 2%, 1%, 0.5%, or most preferably less than 0.1% (v/v) ethanol is present. In case of ammonium sulfate, preferably less than 2M, less than 1M, 0.5M, 0.4M, 0.3M, 0.2M, or most preferably less than 0.1M is present.

Preferably, a dairy bacterial strain according to the invention, comprises an increased amount of expression product of a pilin gene cluster. Expression is herein understood to include any step involved in the production of a polypeptide including, but not limited to transcription, post-transcriptional modification, translation, post-translational modification, and secretion. Accordingly, an expression product is herein defined as any product within the process of expression, including preRNA, mRNA, pre-polypeptide and mature polypeptide. A preferred expression product is a mature polypeptide, more preferably a cluster of polypeptides arranged in the form of a pilin. The pilin gene cluster is a cluster of genes which final expression product is a pilin and may comprise several different genes, such as a sortase gene and one or more genes encoding one or more respective pilin subunits. The pilin cluster is preferably organized into a single operon. Preferably, the amount of expression product of the pilin cluster is increased in view of the expression of said pilin cluster in *Lactococcus lactis* subsp *cremoris* NCDO712 when cultured and assayed under identical conditions. The person skilled in the art knows how to determine the amount of expression product. Methods for determining the amount of expression product (expression level) include, but are not limited to, measurement of (m)RNA using Northern blot or (quantitative) PCR and measurement of protein using Western blot or another immune-based assay. Also within the scope of the present invention is a dairy bacterial strain derived from a parental strain wherein the expression of a pilin cluster is higher in the derived strain as compared to the parental strain, such that the clumping and/or chaining properties of the derived strain are higher as compared to the parental strain. Such strain may be derived by recombinant techniques or by classical techniques such as mutagenesis, preferably followed by screening for a mutant strain comprising the desired properties.

In an embodiment, the dairy bacterial strain according to the invention is a dairy bacterial strain with clumping and/or chaining properties wherein the clumping property results in clumps of at least 20 bacteria per average clump and wherein the chaining property results in chains of at least 8 bacteria per average chain, and comprising increased amount of expression product of a pilin gene cluster.

In an embodiment, the dairy bacterial strain according to the invention is a dairy bacterial strain with clumping and/or chaining properties wherein the clumping property results in clumps of at least 20 bacteria per average clump and wherein the chaining property results in chains of at least 8 bacteria per average chain, wherein the amount of expression product is increased in view of *Lactococcus lactis* subsp *cremoris* NCDO712 when cultured under identical conditions.

In an embodiment, the dairy bacterial strain according to the invention is a dairy bacterial strain with clumping and/or chaining properties, wherein the clumping property results in clumps of at least 20 bacteri per average clump and wherein the chaining property results in chains of at least 8 bacteria per average chain, wherein the pilin gene cluster has a nucleotide sequence that has at least 30% sequence identity with SEQ ID NO: 1, or a part thereof.

In a preferred dairy bacterial strain according to the invention, the pilin gene cluster has a nucleotide sequence that has at least 30%, at least 35%, 40%, 45%, 50%, 55%, 60%, 65%, 70%, 75%, 80%, 85%, 90%, 91%, 92%, 93%, 94%, 95%, 96%, 97%, 98%, 99%, or most preferably at least 100% sequence identity with SEQ ID NO: 1, or a part thereof. "Sequence identity" is herein defined as a relationship between two or more amino acid (polypeptide or protein) sequences or two or more nucleic acid (nucleotide, polynucleotide) sequences, as determined by comparing the sequences. In the art, "identity" also means the degree of sequence relatedness between amino acid or nucleic acid sequences, as the case may be, as determined by the match between strings of such sequences "Identity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux et al., 1984). BestFit, BLASTP, BLASTN, and FASTA (Altschul, et al., 1990). The BLAST X program is publicly available from NCBI and other sources (BLAST Manual, Altschul, S., et al., NCBI NLM NIH Bethesda, Md. 20894). The well-known Smith Waterman algorithm may also be used to determine identity.

Preferred parameters for polypeptide sequence comparison include the following: Algorithm: Needleman and Wunsch (1970); Comparison matrix: BLOSSUM62 from Hentikoff and Hentikoff (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu. Preferably, sequence identity is determined by comparing the whole length of a sequence as identified herein.

A dairy bacterial strain according to the invention may be any suitable dairy bacterial strain known to the person skilled in the art. A preferred dairy bacterial strain is a lactic acid bacterial strain. Lactic acid bacteria are known to the person skilled in the art and are preferably defined as Gram positive, non-spore-forming, anaerobic, catalase negative cocci or rods, forming lactic acid as an end product of their carbohydrate metabolism. Lactic acid bacteria include, but are not limited to, bacterial strains selected from the group consisting of the genera of *Lactobacillus, Lactococcus, Leuconostoc, Carnobacterium, Streptococcus, Bifidobacterium, Bacteroides, Eubacterium, Clostridium, Fusobacterium, Propionibacterium, Enterococcus, Staphylococcus, Peptostreptococcus*, and *Escherichia*, preferably consisting of *Lactobacillus* and *Bifidobacterium*. Preferred species of *Lactobacillus, Bifidobacterium, Streptococcus, Leuconostoc* and *Pediococcus*. are *Lactobacillus reuteri, L. fermentum, L. acidophilus, L. crispatus, L. gasseri, L. johnsonii, L. plantarum, L. paracasei, L. murinus, L. jensenii, L. salivarius, L. minutis, L. brevis, L. gallinarum, L. amylovorus, Streptococcus thermophilus, Leuconostoc mesenteroides, Pediococcus damnosus, P. acidilactici, P. parvulus, Bifidobacterium bifidum, B. longum, B. infantis, B. breve, B. adolescente, B. animalis, B. gallinarum, B. magnum*, and *B. thermophilum*. A more preferred dairy bacterial strain according to the invention is a *Lactococcus* strain, more preferably a *Lactococcus lactis* strain, even more preferably a *Lactococcus lactis* subsp. *lactis* strain or a *Lactococcus lactis* subsp. *cremoris* strain.

The dairy bacterial strain according to the invention with its specific clumping and/or chaining properties when cultured under liquid conditions preferably has the capacity to texturize milk, such as but not limited to, the capacity to increase viscosity when cultured in milk and capacity to increase stress to shearing when cultured in milk. A further preferred property of the dairy bacterial strain according to the invention is that it influences the bacterial localization in cheese. A dairy bacterial strain according to the invention has the property that an increased fraction of bacteria remain in curd during cheese making Fifty percent to 80% of bacterial strains that are not the bacterial strain according to the invention typically remains in the curd. With a the dairy bacterial strain according to the invention, the percentage bacteria in the curd can be increased to at least 85%, 90%, 91%, 92%, 93%, 94%, 95%, 96%, 97%, 98% or at least 99%. Accordingly, the dairy bacterial strain according to the invention preferably has the capacity to increase the fraction of bacteria that remain in curd during cheese making. The cheese can be any cheese and preferably is a cheese as defined herein below. The percentage bacteria that remain in the curd is preferably increased to at least 85%, 90%, 91%, 92%, 93%, 94%, 95%, 96%, 97%, 98% or at least 99%. Preferably, the fraction of bacteria that remain in the curd is increased by at least 10%, 20%, 30%, 40%, 50%, 60%, 70%, 80%, 90%, or to at least 100% as compared to the fraction of bacteria that remain in the curd when using a bacterial strain that is not a bacterial strain according to the invention.

The person skilled in the art knows how dairy bacterial strains can texturize milk, an example is the thickening of milk when producing yoghurt, thus increasing viscosity. A further example is the gel strength, also called gel hardness of fermented milk, such as of yoghurt and cheese. Preferably, the texturizing capacity of a dairy bacterial strain according to the invention is higher than the texturizing capacity of *Lactococcus lactis* subsp *cremoris* NCDO712 when cultured and assayed under identical conditions.

When the dairy bacterial strain according to the invention is a dairy bacterial strain derived from a parental strain such as defined previously herein, the texturizing capacity of said derived strain is preferably compared to the texturizing capacity of the parental strain; the texturizing capacity of the derived bacterial strain preferably being higher than the texturizing capacity of the parental bacterial strain. Higher texturizing capacity preferably is at least 10%, at least 20%, 30%, 40%, 50%, 60%, 70%, 80%, 90%, 100%, 200%, 300%, 400%, 500%, or at least 1000% higher respective texturizing capacity. It is understood that replicates of a diary bacterial strain according to the invention are encompassed by the invention. The term "replicate" refers to the biological material that represents a substantially unmodified copy of the material, such as material produced by growth of micro-organisms, e.g. growth of bacteria in a culture medium.

In a further aspect, the invention provides for a method for the production of a dairy bacterial strain according to the invention, comprising:

culturing a precursor dairy bacterial strain under conditions that are conducive to the development of clumping and/or chaining properties and, optionally, screening for a dairy bacterial strain according to the invention and/or isolating a dairy bacterial strain according to the invention. Preferably, the clumping and/or chaining properties of the dairy bacterial strain obtained by the method are kept for at least 5, at least 10, 15, 20, 25, 30, 35, 40, 45, or at least 50 generations, allowing e.g. the dairy bacterial strain with the clumping and chaining properties to be used as a starter strain for the production of a dairy food product. Preferably, the clumping and/or chaining properties of the dairy bacterial strain obtained by the method are (also) kept during storage such as cold storage (between 0 and 4 degrees Celsius), storage at room temperature and longer term storage in freeze dried, frozen or liquid suspension state. The conditions to be applied to provide the clumping and/or chaining properties to the dairy bacterial strain may be any condition available to the person skilled in the art. Preferably, such condition comprises at least one of mutating the dairy bacterial strain, preferably by chemical treatment, radiation treatment and/or recombinant treatment. Such method is preferably followed by screening for and/or isolating a dairy bacterial strain according to the invention. The person skilled in the art knows classical mutagenesis methods using e.g. chemical treatment and/or radiation treatment. As an example such method comprises providing a dairy bacterial strain, subjecting such strain to mutagenesis by chemical treatment and/or radiation treatment and screening for a dairy bacterial strain according to the invention. When the method is a recombinant method, it preferably comprises bringing a pilin gene cluster, or a part thereof, to overexpression in a dairy bacterial strain, so as to provide the clumping and/or chaining properties according to the invention said dairy bacterial strain. Methods for overexpressing a gene cluster, or a part thereof, are known to the person skilled in the art. The invention further provides for a dairy bacterial strain obtainable by the method of this aspect of the invention.

In a further aspect, the invention provides for a composition comprising a dairy bacterial strain according to the invention. Such composition may or may not be a kit of parts. Such composition is herein referred to as a composition according to the invention. Such composition may be any useful composition, it may e.g. be a food product, food-grade substance or a formulation and may be in any form or state of constitution known to the person skilled in the art. Preferably, in a composition according to the invention, the concentration of bacteria according to the invention ranges from about 1 E–8 weight percent 1 to about 1 weight percent, more preferably from about 5 E–8 to about 0.9 weight percent, more preferably from about 5 E–8 to about 0.8, more preferably from about 5E–8 to about 0.7, more preferably from about 5 E–8 to about 0.6, more preferably from about 1 E–7, 2 E–7, 3 E–7 or 4 E–7 to about 5 E–7 weight percent with respect to the total weight of the formulation, and/or about 1 E+4, 1 E+5, or 1 E+6 to about 1 E+8, 1 E+9, or about 1 E+10 colony forming units/ml of composition, even more preferably about 1 E+6 to about 1 E+10 colony forming units/ml of composition.

More preferably, in a composition according to the invention, the concentration of bacteria according to the invention ranges from 1 E–8 weight percent 1 to 1 weight percent, more preferably from 5 E–8 to 0.9 weight percent, more preferably from 5 E–8 to 0.8, more preferably from 5E–8 to 0.7, more preferably from 5 E–8 to 0.6, more preferably from 1 E–7, 2 E–7, 3 E–7 or 4 E–7 to 5 E–7 weight percent with respect to the total weight of the formulation, and/or 1 E+4, 1 E+5, or 1 E+6 to 1 E+8, 1 E+9, or 1 E+10 colony forming units/ml of composition, even more preferably 1 E+6 to 1 E+10 colony forming units/ml of composition. A colony forming unit is a term known to the person skilled in the art and one unit typically refers to the amount of bacteria that forms one colony on a culture plate; it is a term to refer to viable bacteria. Even more preferably, in a composition according to the invention, the concentration of bacteria according to the invention ranges from 1 E−7 to 5 E−7 weight percent with respect to the total weight of the composition and/or 1 E+6 to 1 E+10 colony forming units/ml of composition. A composition according to the invention may further comprise another dairy bacterial strain. Such further dairy bacterial strain may be present in the same, single, composition or may be present separately in a kit of parts. Such further dairy bacterial strain may be any dairy bacterial strain defined elsewhere herein. A preferred further dairy bacterial strain is a *Streptococcus thermophilus* and/or a *Lactobacillus* species. Another preferred further bacterial strain may be a probiotic bacterial strain. Probiotic bacteria are known to the person skilled in the art and preferably are bacteria of a *Bifidobacterium* species or lactic acid bacteria e.g. of a *Lactobacillus rhamnosus* species. Within the scope of the invention is the composition according to the invention as a starter culture for the production of a food product, preferably in freeze dried, frozen or liquid suspension state. A composition according to the invention comprising a dairy bacterial strain according to the invention, may also itself be a food product. A food product as defined herein is a substance suitable for consumption by a subject, preferably a human or an animal, more preferably a human. A food product may be of plant or animal origin, and may contain essential nutrients, such as carbohydrates, fats, proteins, vitamins, and/or minerals. A food product may be intended for ingestion by an organism and subsequently assimilation by the organism's cells to produce energy, maintain life, and/or stimulate growth. A food product according to the invention includes but is not limited to a substance selected from the group consisting of a dairy-, grain-, vegetable-, fruit-, fish-, or meat-based product; a preferred food product according to the invention is dairy food product, preferably a yoghurt, a curd or a cheese. A preferred cheese is selected from the group consisting of Gouda, Cheddar, Edam, Brie, Camembert, Stilton, Gorgonzola, Blue cheese, Goat cheese, Swiss cheese such as Emmental, Gruyere Brick, Maasdam, and Mozarella. The term "based product" is herein defined that the food product is produced from a specific raw material or precursor food product such as dairy, grain, vegetable, fruit, fish, or meat. The food product may be based on a mixture of different raw materials e.g. a mixture of dairy and grain including legumes, a mixture of dairy and fruit or a mixture of meat and fruit.

In a further aspect, the invention further provides for a method for the production of a food product according to the invention, preferably a dairy food product according to the invention, more preferably a fermented milk product such as a yoghurt or a cheese, from a precursor food product comprising inoculating the precursor food product with a dairy bacterial strain according to the invention or with a composition according to the invention and incubating the inoculated precursor food product. When the food product according to the invention is a cheese or a yoghurt, the precursor food product is preferably milk, preferably a milk selected from the group consisting of cows, buffalo, goats, sheeps or mixes thereof. Depending on the food product to be produced the person skilled in the art knows to select to proper temperature and time for the incubation. In the method according to the invention for the production of a food product, preferably a further ingredient is added to the incubation, preferably an ingredient selected from the group consisting of a flavoring agent, a fruit or fruit concentrate, a syrup, a prebiotic, a bacterial strain, such as a probiotic strain, a coloring agent, a thickening agent, a preserving agent, a sweetener, and an enzyme. A thickening agent is preferably a starch, a starch derivative, a cellulose derivative, a gelatin, gum Arabic, a carrageenan, gellan gum, xanthan gum, guar gum, and locust bean gum. A thickening agent may also be an enzyme such as a transglutaminase. A sweetener may be any sweetener known to the person skilled in the art, such as a sugar, a polyol sweetener, *Stevia* or an intense sweetener, or mixtures thereof. The polyol sweetener is preferably a sweetener selected from the group consisting of sorbitol and xylitol. The intense sweetener is preferably a sweetener selected from the group consisting of aspartame, acesulfame-K and a saccharin. The invention further provides for a food product, preferably a dairy food product according to the invention, obtainable by a method according to this aspect of the invention. The invention further provides for a food product, preferably a dairy food product, comprising a dairy bacterial strain according to the invention. When the food product is a cheese, the cheese preferably has an increased fraction of bacteria that remain in the curd, as defined here above, compared to the fraction of bacteria that remain in the curd when using a bacterial strain that is not a bacterial strain according to the invention. Preferably, the food product, preferably a dairy food product according to the invention is packaged in a suitable container. The container is preferably a closed container which is capable to prevent or retard oxygen gas from diffusing from the atmosphere into the food product. Preferably, said container further comprises a headspace above the food product, wherein preferably more than 90% (v/v) occupied by the headspace is provided as an inert gas such as nitrogen or carbon dioxide. Accordingly, preservation of the food product is enhanced and/or survival of the dairy bacterial strain according to the invention is enhanced.

The invention further provides for the use of a dairy bacterial strain according to the invention, or of a composition according to the invention for the preparation of a food product, preferably a dairy food product.

The inventors have demonstrated that a dairy bacterial strain according to the invention comprises increased conjugation efficiency. This property is not limited to dairy use of the bacterial strain. Accordingly, in a further aspect, the invention provides for a bacterial strain comprising an increased amount of expression product of a pilin gene cluster, wherein the amount of expression product is increased in view of *Lactococcus lactis* subsp *cremoris* NCDO712. Such strain is herein referred to as a bacterial strain according to the invention or a bacterial strain according to the invention with increased conjugation properties, or a bacterial strain according to the invention with increased conjugation efficiency; it should be noted that this aspect of the invention is not limited to dairy bacterial strains but applies to any bacterial strain that has conjugation capacity, at least to some extent. Preferably, the conjugation efficiency is increased with at least 10%, at least 15%, 20%, 25%, 30%, 40%, 50%, 60%, 70%, 80%, 90%, 100%, 200% (two-fold), 500% (five-fold), ten-fold, 20-fold, 30-fold, 40-fold, 50-fold, sixty-fold, seventy-fold, eighty-fold, ninety-fold, 100-fold, 1000-fold, 10,000-fold, 100,000-fold or at least 1000,000-fold in view of *Lactococcus lactis* subsp *cremoris* NCDO712. When a bacterial strain with increased conjugation efficiency is derived from a parental strain, the conjugation efficiency and the above depicted increase thereof may be compared to the parental strain where the strain according to the invention is derived from. In a preferred bacterial strain according to the invention, the pilin gene cluster has a nucleotide sequence that has at least 30% percentage sequence identity with SEQ ID NO: 1, or a part thereof. More preferably, the pilin cluster, has at least 35%, at least 40%, 45%, 50%, 55%, 60%, 65%, 70%, 75%, 80%, 85%, 90%, 91%, 92%, 93%, 94%, 95%, 96%, 97%, 98%, 99%, or most preferably at least 100% sequence identity with SEQ ID NO: 1 or a part thereof.

The invention further provides for a method for gene transfer by conjugation comprising, providing a composition, referred to as composition for gene transfer, comprising at least one bacterial strain according to the invention and incubating the composition under conditions conducive to conjugation. The person skilled in the art is aware of gene transfer by conjugation and knows how to perform the technique. Preferably, the composition for gene transfer comprises at least two bacterial strains, one bacterial strain being a bacterial strain according to the invention.

The invention further provides for a method for the production of a desired bacterial strain comprising a genetic trait of interest, comprising providing a composition comprising:
- a precursor of the desired bacterial strain, wherein the precursor lacks the genetic trait of interest, and
- a donor bacterial strain comprising the genetic trait of interest, incubating the composition under conditions conducive to conjugation, and optionally isolating the desired bacterial strain comprising the genetic trait of interest, wherein at least one bacterial strain in the composition is a bacterial strain according to the invention.

The invention further provides for a bacterial strain comprising a genetic trait of interest, obtainable by a method according to this aspect of the invention.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) more or less 0.1% of the value.

The sequence information as provided herein should not be so narrowly construed as to require inclusion of erroneously identified bases. The skilled person is capable of identifying such erroneously identified bases and knows how to correct for such errors. In case of sequence errors, the sequence of the polypeptides obtainable by expression of the genes as represented by SEQ ID NO: 2 should prevail.

All patent and literature references cited in the present specification are hereby incorporated by reference in their entirety.

Sequences

| SEQ ID NO | Description | Sequence |
|---|---|---|
| 1 | Pilin gene cluster | See sequence listing |
| 2 | Leader sequence | See sequence listing |
| 3 | pLP712H_FW | GGACCAGATGGTACTTTTGAAGCG |
| 4 | pLP712H_RV | GGTAAAGTCACTATTGATGGACAGCC |

-continued

Sequences

| SEQ ID NO | Description | Sequence |
|---|---|---|
| 5 | pilinPstI forw | CCGctgcagTTTGCAACAGAACCGTAATTGA TTAGC |
| 6 | pilinXhoI rev | CGGctcgagTTAAGTAATTTGAATTACTTGC TTTGAGAGTTGTTTAAAGG |

FIGURE LEGENDS

FIG. 1. Plasmid maps of pSH73, pSH74, and pNZ712. Plasmid pNZ712 includes genes encoding functional nisin immunity (nisCIP) and copper resistance (lcoRSABC). A 16-kb plasmid pSH74 contains a novel 8-kb pilus gene cluster spaCB-spaA-srtC1-srtC2. Plasmid pSH73 harbors repX, repB and cadCA genes. The latter encode a cadmium resistance regulatory protein and a cadmium efflux ATPase.

Figure 2:
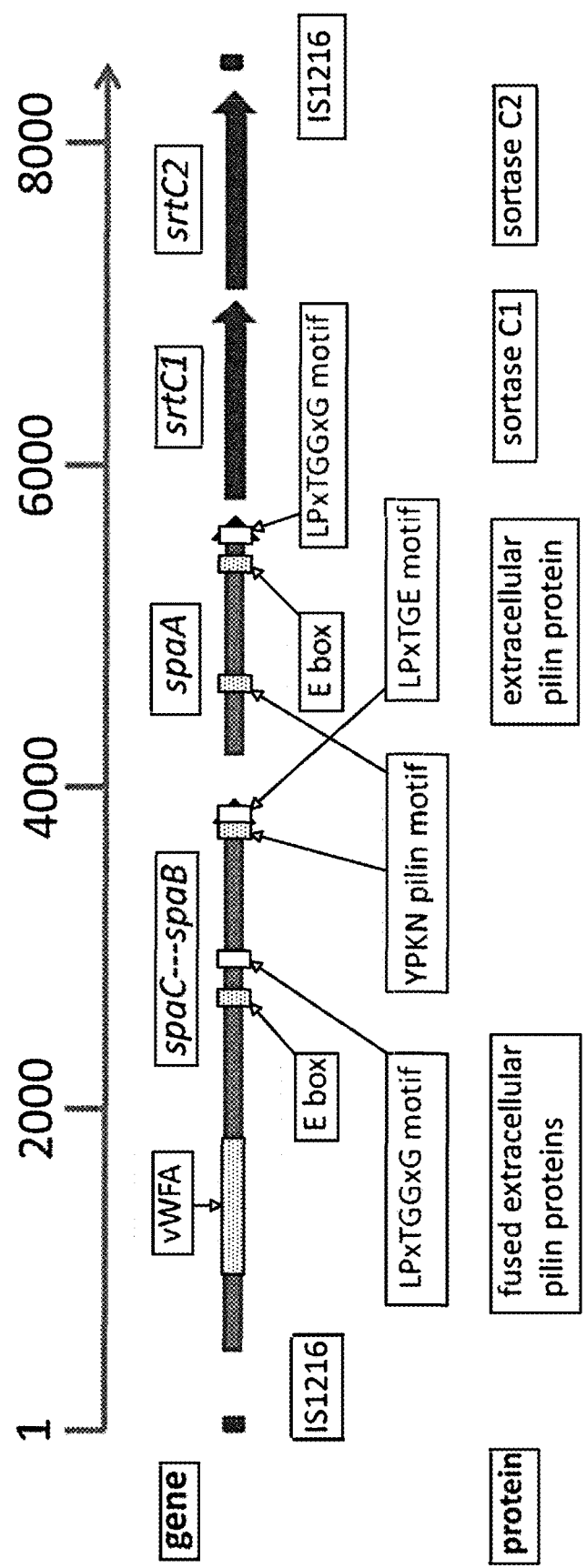

FIG. 2. Pilin gene cluster and their suggested functions. The pilin cluster consists of spaCB-spaA-srtC1-srtC2 genes with 2 insertion regions IS1216 at the ends. The pilin cluster contains two adjacent srtC genes encoding sortase C proteins, which probably would catalyze the assembly of pilin proteins into pili. The spaA gene encodes SpaA protein and we suggest that SpaA is the major pilin backbone subunit. The spaC and spaB genes are fused, but SpaCB is expected to be cleaved by sortase C. SpaB is expected to be the basal pilus subunit and linked to the peptidoglycan by sortase A. SpaC has an "E box" (YALTETKTP) and a vonWillebrand type-A domain (vWFA). The "E box" is necessary to link SpaC to SpaA proteins. It has been speculated that the SpaC segment might be involved in bacterial adhesion to surfaces and might be the pilin tip protein.

Figure 3:
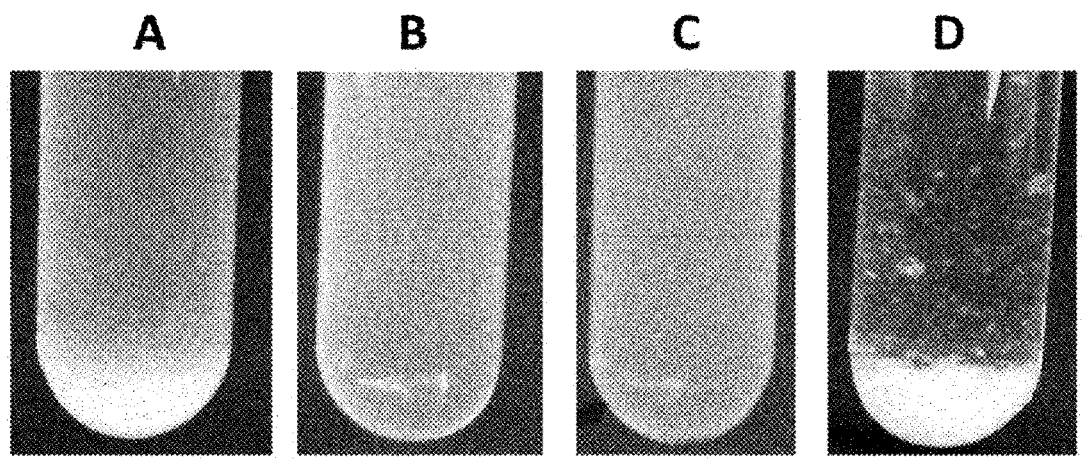

FIG. 3. Cell aggregation after pilus over-expression. A—L. lactis NCDO712, B—empty vector control MG1363 (pIL253), C—MG1363(pIL253pilΔ1), D—MG1363 (pIL253pil). The images were taken in 3 minutes after re-suspending the cells in the buffer, pH 6.8.

Figure 4:
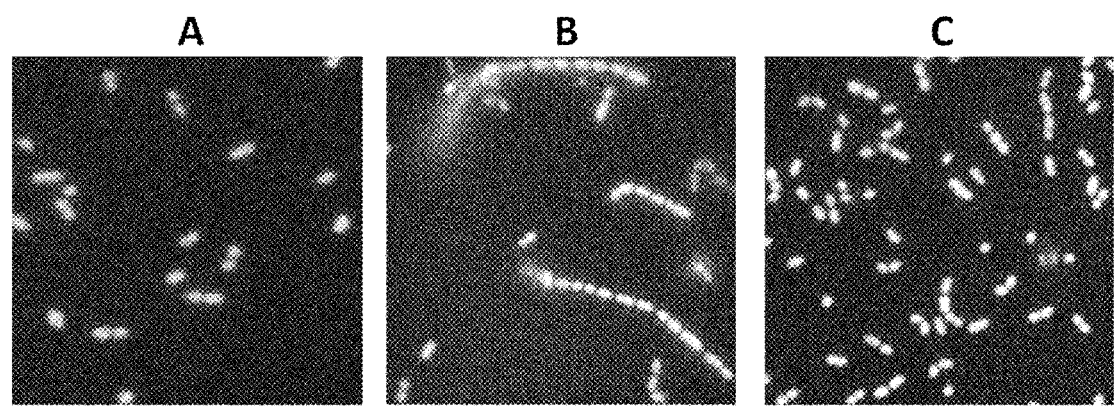

FIG. 4. Pilin expression in L. lactis leads to increased chain length. A—MG1363pIL253, B—MG1363 (pIL253pil), C—MG1363(pIL253pilΔ1).

Figure 5:
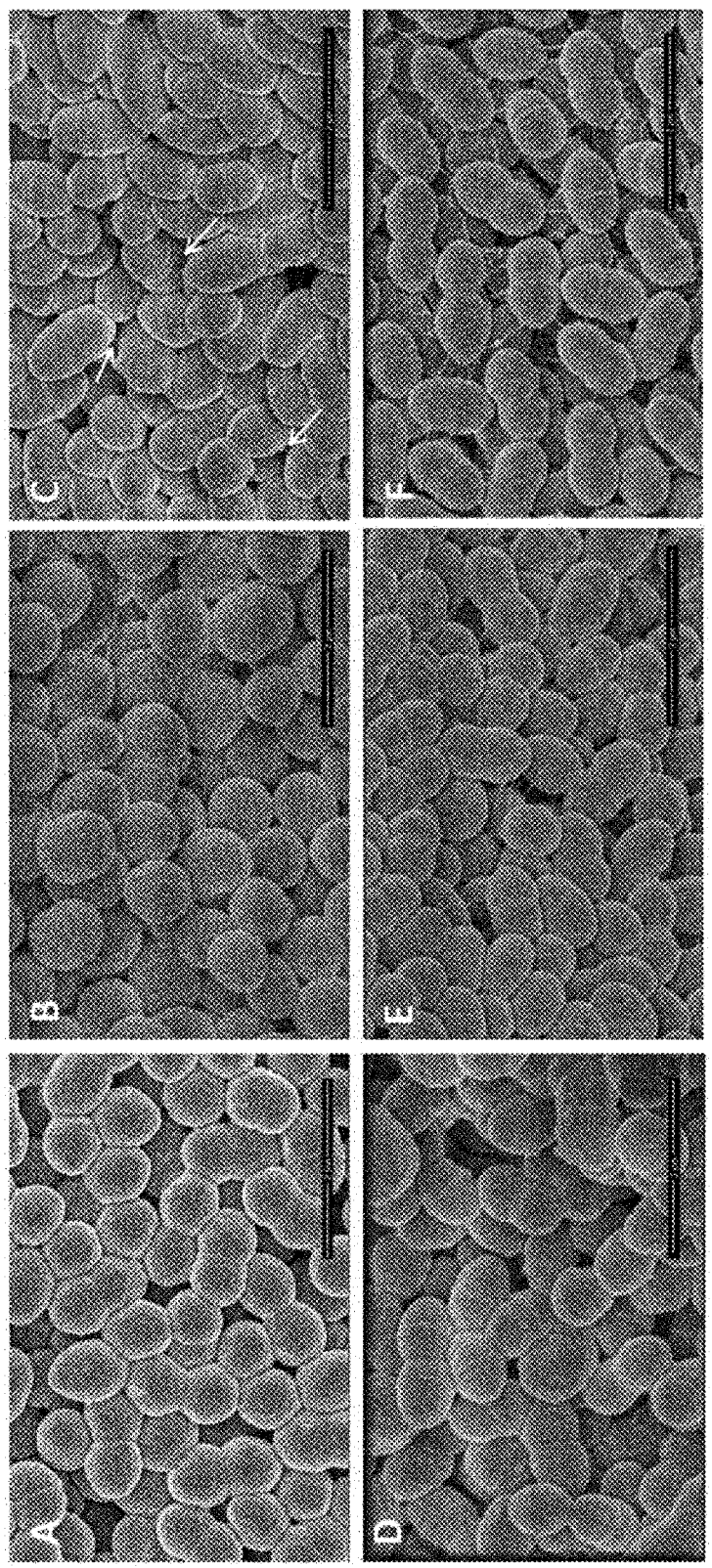

FIG. 5. Scanning electron microscopy of pilin overexpressing L. lactis strains. A—NCDO712, B—IL1403, C—IL1403(pIL253pil), D—MG1363(pIL253), E—MG1363(pIL253pil), F—MG1363(pIL253pilΔ1). White errors indicate pili in panel C. White bars: 2 μm in all panels. All panels have the same 50 000× magnification.

Figure 6:
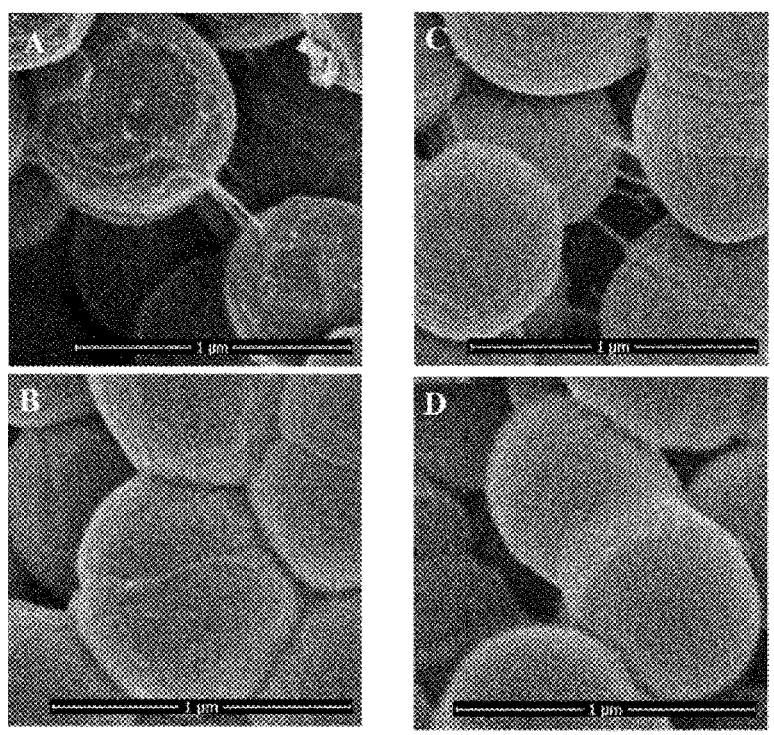

FIG. 6. Scanning electron microscopy of pilin overexpressing L. lactis strains. A—NCDO712(pIL253pil), B—NCDO712, C—MG1363(pIL253pil), D—MG1363 (pIL253). White bars: 1 μm in all panels.

Figure 7:
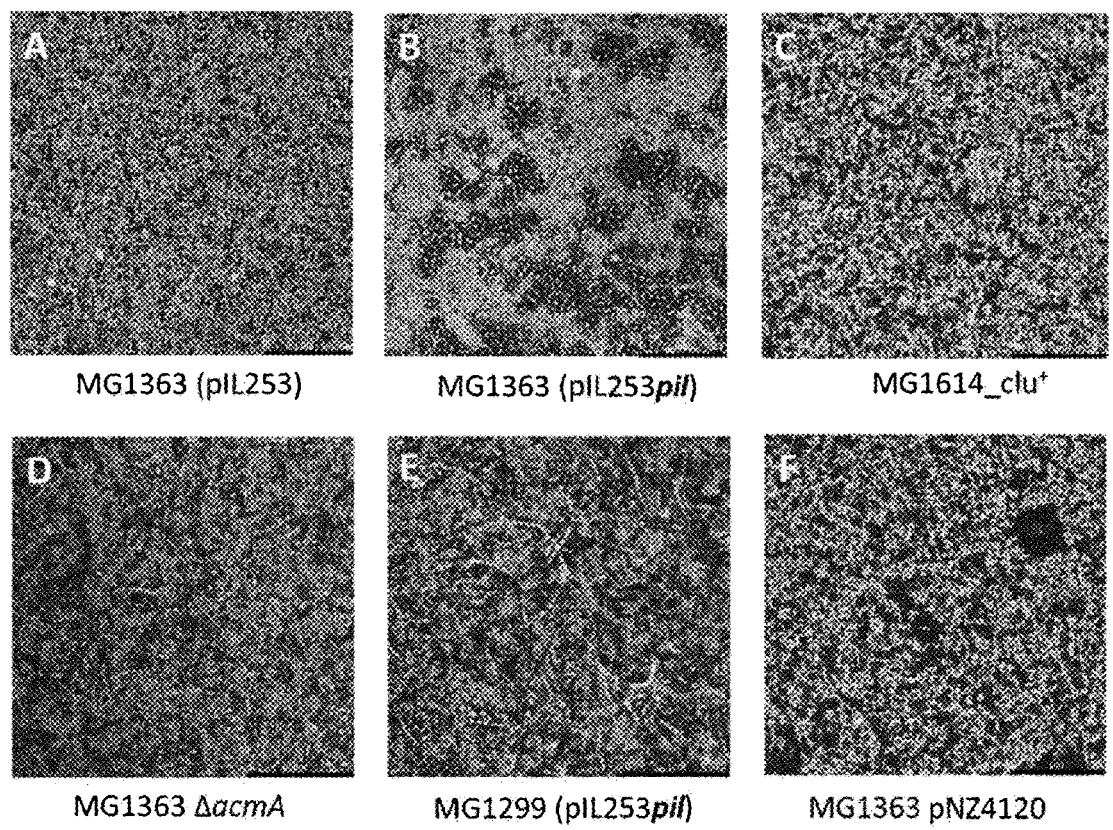
Figure 8A:
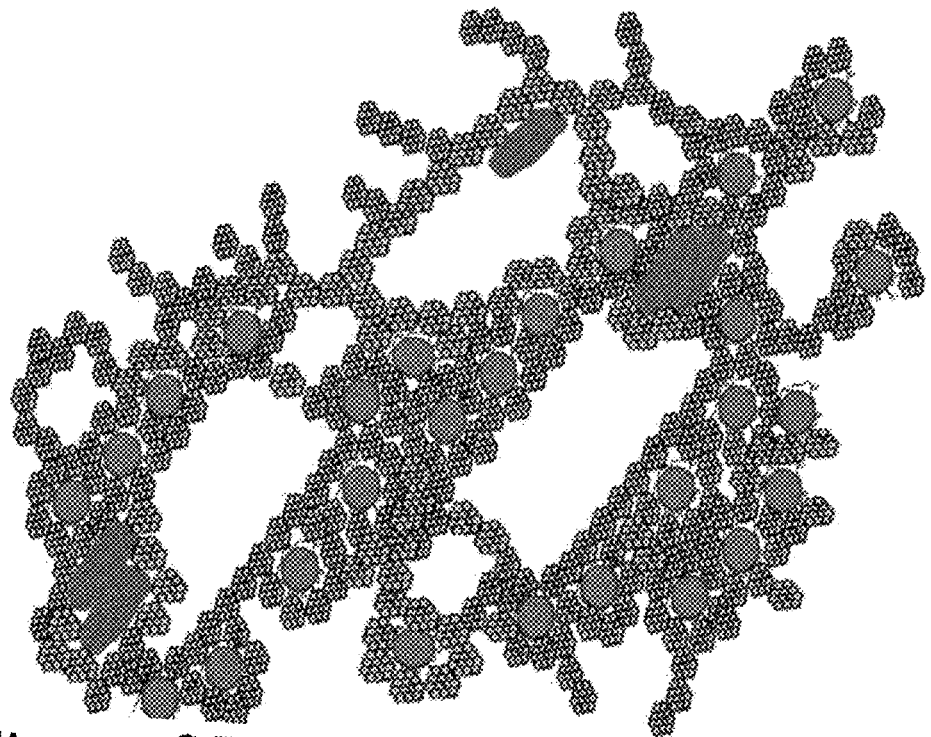
Figure 8B:
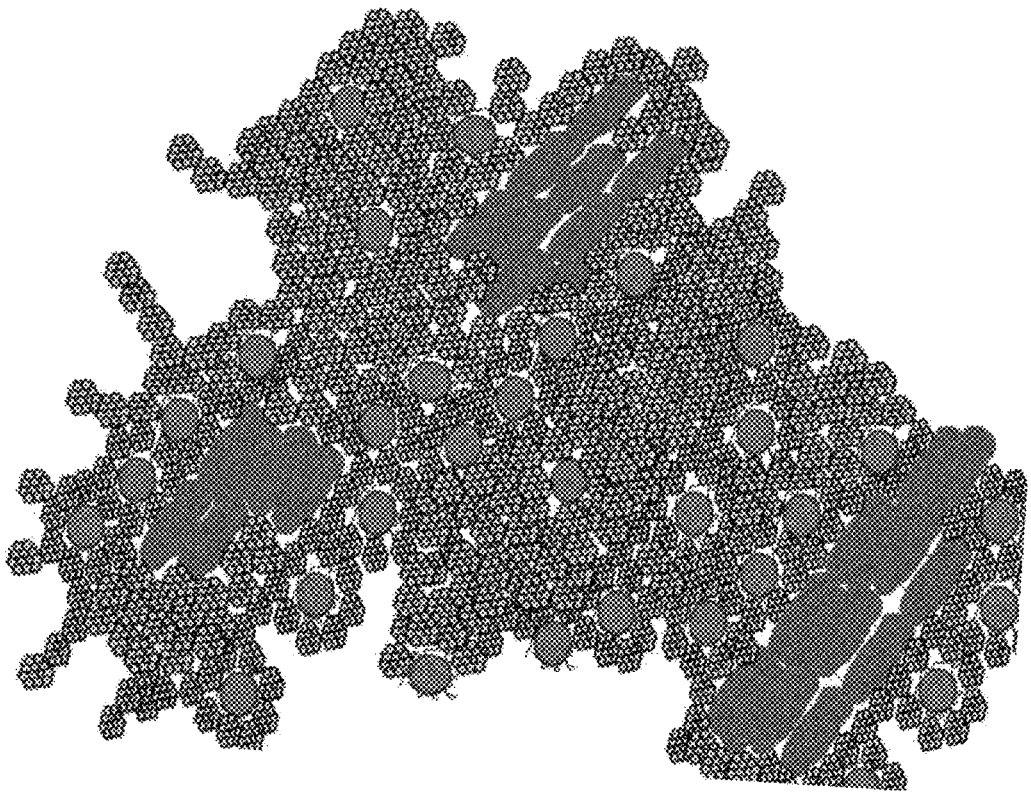
Figure 8C:
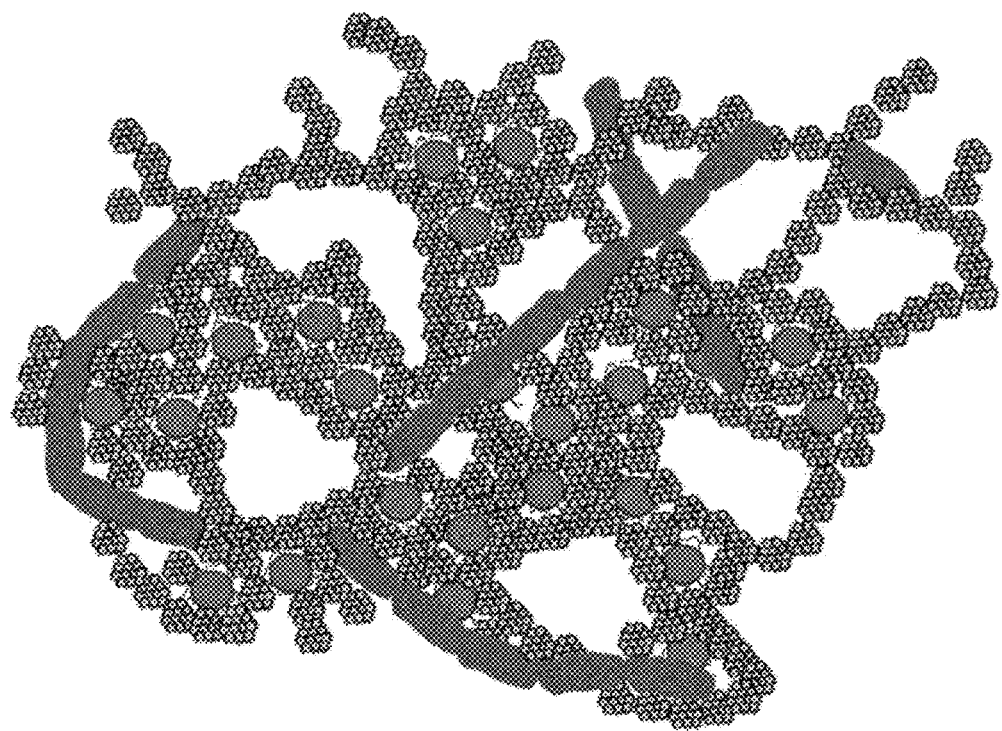
Figure 8D:
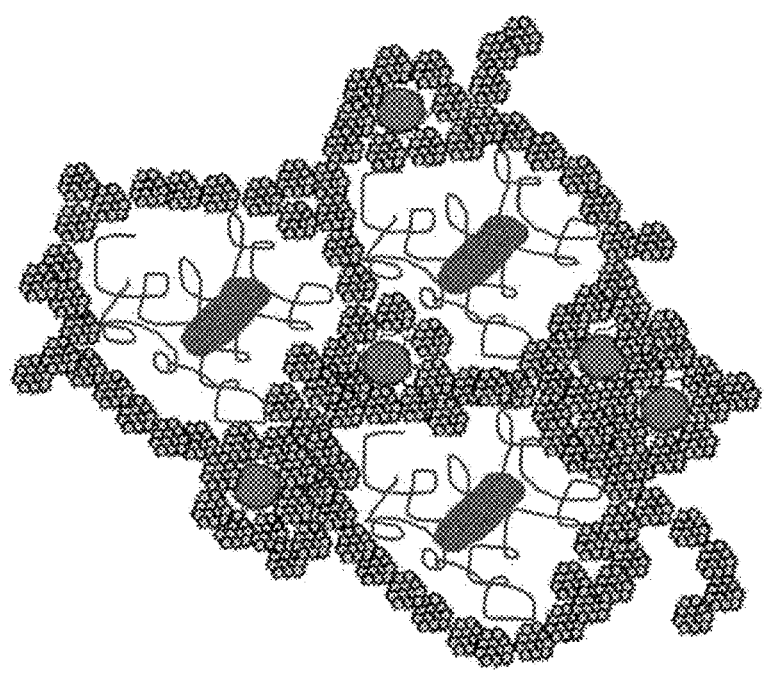

FIG. 7. Microstructure of milk fermented by L. lactis strains with altered surface properties. Bacterial cells are ◆, while proteins ✦ and fat droplets ● form aggregated matrix; the black areas represent the serum fraction. The black bar in the right corner displays the 25 (B) L. lactis MG1363 expressing pili shown chaining, clumping, hydrophobic phenotype seemed to be located in serum regions compared to (A) its control strain, (C) clumping and hydrophobic transconjugant MG1614 harboring pLP712 seem to be attached to protein matrix, (D) chaining MG1363 seems to go through the protein matrix and serum regions, (E) pili expressing MG1299 shown cell chaining, clumping and hydrophobicity similar to (D) does not show exact pattern of localization in milk matrix, (F) EPS producing MG1363 seems prefer localization in serum regions.

FIG. 8. Model: bacteria as structure elements in fermented foods. ● is fat droplet (Ø=1 μm, can be up to 5-6 μm, $10^{10}$ droplets/ml) stabilized by whey proteins (Ø=4-6 nm, $10^{77}$ proteins/ml), ☼—casein micelle (Ø=200 nm, $10^{14}$ micelles/ml), ✦—bacterial cell (Ø=1 μm, $10^9$ cell/ml). Panel A shows the structure of milk fermented with unmodified cell surface: the fat droplets and cells are part of casein network with cavities in which the serum phase is confined. Such a gel has a weak network. Panel B shows the structure of milk fermented with pili over-expressing cells that locate in cavities where aqueous phase should be located (consistent with chaining and clumping lactococcal phenotypes studied here). Panel C shows the structure of milk fermented with chaining cells. The gel structure is weak because of spaces in the casein network and long bacterial chains which probably work as structure breakers; but the viscosity of such fermented milk increases possibly due to long cell chains which increase solid content. Panel D shows the gel structure of milk with cavities in protein matrix fermented with EPS producing strains.

FIG. 9.

Types of interactions in milk between bacterial cell and milk components. The covalent bond (e.g. C—C) possesses 350 kJ/mol, van der Waal's—10 kJ/mol, electrostatic—15 kJ/mol, and hydrogen—21 kJ/mol. Force between micellar casein (or denatured whey) protein and cell for LGG is about 0.4 nN (7), and it is very strain-dependent.

EXAMPLES

The present invention is further described by the following examples which should not be construed as limiting the scope of the invention.

Unless stated otherwise, the practice of the invention will employ standard conventional methods of molecular biology, virology, microbiology or biochemistry. Such techniques are described in Sambrook et al. (1989) Molecular Cloning, A Laboratory Manual ($2^{nd}$ edition), Cold Spring Harbor Laboratory, Cold Spring Harbor Laboratory Press; in Sambrook and Russell (2001) Molecular Cloning: A Laboratory Manual, Third Edition, Cold Spring Harbor Laboratory Press, NY; in Volumes 1 and 2 of Ausubel et al. (1994) Current Protocols in Molecular Biology, Current Protocols, USA; and in Volumes I and II of Brown (1998) Molecular Biology LabFax, Second Edition, Academic Press (UK); Oligonucleotide Synthesis (N. Gait editor); Nucleic Acid Hybridization (Hames and Higgins, eds.).

Example 1. Plasmid Complement of Lactococcus lactis NCDO712 Reveals a Novel Pilin Gene Cluster Introduction Lactococcus lactis is a Gram-positive, non-pathogenic, non-spore forming lactic acid bacterium (LAB) that is often isolated from plant material or a dairy environment (75, 159). It is widely used in the dairy industry as a starter culture for the production of cheese, butter milk and quark. Strains of L. lactis typically contain one to eight different plasmids (67, 93) ranging from 1 kb (69) to more than 100 kb in size (110, 146). The plasmids often specify traits of industrial importance such as growth on lactose, milk protein utilization and stress resistance (68, 83). Examples are the 5 plasmids of L. lactis SK11, a phage-resistant dairy strain used in cheese making (143), and in the 7 plasmids of L. lactis IL594, the parent of the plasmid-free strain IL1403 (100). Other important plasmid-encoded functions for L. lactis include bacteriocin production (74, 81, 85, 92, 104) and resistance (77, 101, 120), antibiotic resistance (92, 136) and bacteriophage resistance (66, 84, 130, 131, 148, 149). Also metal ion resistance systems are found frequently to be plasmid encoded (129). Moreover, a recent publication described a CRISPR-Cas system that was encoded on a lactococcal plasmid, although it was concluded not to be functional (125). In addition several genes related to lactococcal surface properties are carried on plasmids (109, 125, 132), such as aggL—a gene responsible for cell auto-aggregation, or genes responsible for adhesion to mucus (105). One of the most intensively studied L. lactis strains is MG1363, a plasmid-cured derivative of strain NCDO712 (95, 118). NCDO712 was originally isolated from a dairy starter culture and was shown to harbour 5 plasmids with molecular sizes of 33, 9, 5.2, 2.5, and 1.8 MDa (95). During plasmid curing of strain NCDO712, derivatives harboring individual plasmids were obtained, allowing a targeted analysis of plasmid-encoded functions (95). Important biotechnological properties of the strain, namely lactose utilization and proteolysis, were linked to the 33 MDa (55 kb) plasmid pLP712 (95, 160). This lactose/protease plasmid pLP712 (160) can be transferred to other lactococcal strains by conjugation (96). Conjugation can occur through various rearrangements which include co-integrate formation between pLP712 and a genome-encoded sex factor (SF). The co-integrate is roughly double the size of pLP712 since the SF is 59.498 kb (97). After conjugation approximately half of the transconjugants displayed an aggregating phenotype and transferred the lactose/protease plasmid with high-frequency (71, 96, 107, 117, 158). The aggregating phenotype is only seen in transconjugants carrying the pLP712-SF co-integrate (97, 148) and it was linked to the cluA gene which is located on the SF (99, 148). The cluA gene encodes a surface protein involved in cell-to-cell contact and cell aggregation (99, 148).

Some L. lactis strains also express proteinaceous surface appendages called pili (113, 123, 130). Pili are known to have different functions in bacteria, including adhesion to surfaces (type I pili) or motility (type IV pili) (94, 121, 113, 122). One of the best described is the sex pilus involved in conjugation in Escherichia coli (80). Pilin biosynthesis genes can be encoded by the chromosome (132) or on plasmids (125) and they are described to be involved in cell aggregation (155), bacterial adherence to host cells (105, 151, 157) or attachment to environmental substrates/surfaces (150). Two plasmids of L. lactis NCDO712 have already been sequenced and published. Plasmid pLP712 (55395 bp) harbors the genes for lactose import and catabolism, the extracellular protease PrtP, and genes encoding extracellular proteins, transposases, and hypothetical proteins (160). Plasmid pSH71, the smallest one (2062 bp) (88), is highly similar to pWV01 (88, 116) and both of them are the basis of a broad range of lactococcal cloning vectors (88, 111, 112, 126, 127, 138).

We here sequenced the plasmids of NCDO712 and found that contrary to earlier reports it contains 6 but not 5 plasmids (95). The additional plasmid encodes functional nisin immunity and copper resistance genes and on one of the other plasmids we could identify a novel pilin gene cluster which we showed to be functional by overexpression analysis followed by phenotypic characterizations.

Materials and Methods

Bacterial strains, growth conditions and medium.

*L. lactis* subsp. *cremoris* NCDO712 (95) and its derivatives (Table 1) were grown at 30° C. in M17 (Oxoid, Thermo Scientific, Hampshire, UK) supplemented with 1% glucose (GM17). When required, erythromycin (Ery; 10 μg/ml), chloramphenicol (Cm; 5 ug/ml), rifampicin (Rif; 50 μg/ml), and streptomycin (Str; 100 μg/ml) were added to the indicated final concentrations. The lactose-positive *L. lactis* strains ND0712, SH4109, and MG1299 were grown in M17 containing 1% lactose (LM17). All incubations were carried out at 30° C.

TABLE 1

Strains and plasmids used in this study.

| Strain or plasmid | Characteristics | Reference |
|---|---|---|
| *L. lactis* strains | | |
| NCDO712 | *L. lactis* dairy isolate (pLP712, pSH71, pSH72, pSH73, pSH74, pNZ712) | (95) This study |
| MG1363 | Plasmid-cured derivative of *L. lactis* NCDO712 | (95) |
| SH4109 | Prophage-cured derivative of *L. lactis* NCDO712 containing all 6 plasmids found in this study | (95) |
| MG1388 | A phage T712 lysogen derived from *L. lactis* MG1363 | (95) |
| MG1362 | Derivative of *L. lactis* NCDO712 (harbors pSH72) | (95) |
| MG1063 | Derivative of *L. lactis* NCDO712 (harbors pSH73 and pSH72) | (95) |
| MG1261 | Derivative of *L. lactis* NCDO712 (harbors pSH73) | (95) |
| MG1365 | Derivative of *L. lactis* NCDO712 (harbors pSH71) | (95) |
| MG1299 | Derivative of *L. lactis* NCDO712 (harbors pLP712) | (95) |
| NZ9700 | Nis$^R$; Derivative of *L. lactis* MG1363; pepN::nisRK | (72) |
| MG1614 | Str$^R$ and Rif$^R$ derivative of *L. lactis* MG1363 | (95) |
| IL1403 | Plasmid-free derivative of *L. lactis* IL594 | (75) |
| Plasmids | | |
| pIL253 | Ery$^R$; 4.9 kb; Low copy-number derivative of pAMβ1 | (145) |
| pIL253pil | Ery$^R$; 13.1 kb; pIL253 harboring pSH74 pilin operon spaCB-spaA-srtC1-srtC2 with 300 bp upstream region | This study |
| pIL253pilΔ1 | Ery$^R$; 11.6 kb; pIL253 harboring spaCB-spaA-srtC1-srtC2 with 1,5-kb internal deletion in spaCB | This study |

Sequencing of *L. lactis* NCDO712 Total DNA and Sequence Assembly.

Total DNA of *L. lactis* NCDO712 and derivatives was isolated using phenol-chloroform extraction as previously described (140) with the following modifications. The exponentially growing cells were harvested by centrifugation (10 min at 6240 g) after which the cell pellet was re-suspended in THMS buffer (30 mM Tris-HCL (pH 8), 3 mM magnesium chloride, 25% sucrose) containing lysozyme (2 mg/ml) and 50 μg/ml RNase and incubated for 1 h at 37° C. Subsequently, the cells were treated with SDS (final concentration 1%) for 20 min at 65° C. After that proteinase K (0.3 mg/mi) was added and incubation was continued for 10 min at 37° C. Total DNA was extracted from the lysate using several extractions with phenol/chloroform after which it was precipitated with isopropanol. The DNA was dissolved in sterile water.

The purified total DNA was sheared to fragments of approximately 500 bp using the Covaris ultrasone device (KBioscience, LGC, Köln, Germany) The paired-end NEB NExtGen library preparation kit (New England Biolabs, Inc., MA, US) was used according to the manufacturer's instructions to prepare the NGS library. The libraries were 101 bases paired-end sequenced on an Illumina HiSeq2000 (Illumina, Inc., San Diego, Calif., USA). Velvet (162, 163) was used in combination with VelvetOptimiser (http://bio-informatics.net.au/software.velvetoptimiser.shtml) to perform de novo paired-end assembly of the genome. All contigs that did not map to the *L. lactis* MG1363 genome were assumed to be plasmid fragments; these were first scaffolded by mapping onto known *L. lactis* plasmids in the NCBI database. Further scaffolding was supported by PacBio sequencing (BaseClear, Leiden, the Netherlands) on a 5-kb library of NCDO712 total DNA. Remaining gaps in the plasmid sequences were closed with dedicated PCR reactions followed by amplicon sequencing (BaseClear, Leiden, the Netherlands).

Initial automatic annotation of the plasmids was performed using the RAST annotation server (72). Manual curation of plasmid-encoded features was performed with Artemis (88, 137), followed by family, domain, motif and context analyses of encoded proteins using BlastP (NCBI) and Interpro (http://www.ebi.ac.uk/interpro/). IS elements and transposase genes were identified using IS Finder (https://www-is.biotoul.fr//). The DNA sequences of the assembled plasmids were used for a BLAST search (http://blast.ncbi.nlm nih.gov/Blast.cgi) in the NCBI plasmid database containing complete plasmids. The determination of single nucleotide polymorphisms of NCDO712 in comparison to the sequenced derivative MG1363 was performed using the Breseq software package (83) and the GenBank file: NC_009004 in combination with corresponding next generation sequencing data: SRA064225 as templates.

For non-synonymous SNPs the software SIFT (113) and the UniProt-TrEMBL database (http://www.uniprot.org/) were used to predict whether an amino acid substitution would affect protein function.

Determination of nisin and copper resistance.

Overnight cultures of *L. lactis* were diluted in fresh M17 medium to a final optical density at 600 nm ($OD_{600}$) of 0.03. To measure nisin resistance, the medium was supplemented with nisin from *L. lactis* (N6764-5G, Sigma-Aldrich, Steinheim, Germany) at different end concentrations (0-20 ng/ml). *L. lactis* NZ9700 was used as a control (Table 1). The strains were grown in 10 ml sterile tubes for 7 h at 30° C. The $OD_{600}$ was measured after 4 h and after 7 h using a UV/Visible Ultrospec 2000 spectrophotometer (Pharmacia Biotech, Cambridge, England).

To measure copper resistance, $CuSO_4$ (0-4.8 mM end concentrations) was added to the growth medium. A 96 well microplate with the samples was incubated for 21 h at 30° C. The $OD_{600}$ was measured every 15 min with a SpectraMax spectrophotometer (Molecular Devices, Wokingham, Berkshire, UK).

Pilin overexpressing in *L. lactis*.

The spaCBA-srtC1-srtC2 locus (designated as pil locus) including its 300 bp upstream region was amplified with KOD Hot Start Polymerase (Merck Millipore, Madison, Wis., USA) using the pilinPstI forward primer (SEQ ID NO: 5) and the pilinXhoI reverse primer (SEQ ID NO: 6). The purified PCR product was digested with PstI and XhoI and ligated to similar digested pIL253 using T4 DNA Ligase (Invitrogen, Breda, The Netherlands). The ligation mixture was transformed (161) to electro-competent (102) MG1363 cells. Transformants harbouring the anticipated pIL253pil plasmid (Table 1) were selected using colony PCR confirmation with primers pLP712H_FW and pLP712H_RV (SEQ ID NO:'s 3 and 4, respectively).

An internal deletion of 1451 bp in the spaCB gene was constructed by digestion of pIL253pil with AatII followed by re-ligation and introduction of the plasmid in L. lactis MG1363. The resulting plasmid was designated pIL253pilΔ1 (Table 1).

Cell aggregation.

L. lactis cells from a 10 ml overnight culture were washed twice with 10 ml sterile 10 mM phosphate buffer, pH 6.8, re-suspended in the same buffer, after which cell sedimentation was observed visually, while cell chaining was examined by light microscopy.

Scanning Electron Microscopy (SEM). Bacterial cells were cultured for 1 day on GM17 agar plates. From plates with 50-100 colonies small pieces of agar gel carrying less than 5 colonies were cut out and placed in a microscope sample holder. All further steps of cell fixation, washing, dehydration, staining, freeze-drying, electron microscopy, and image analysis were performed according to (103). For imaging a FEI Magellan 400 FESEM electron microscopy (Wageningen Electron Microscopy Centre, The Netherlands) was used.

Conjugation experiments.

Conjugation experiment were performed as described previously (124, 147) with L. lactis MG1614 as a recipient strain. Transconjugants were selected on milk agar plates containing 0.004% bromocresol purple (Merck, Darmstadt, Germany), streptomycin (100 µg/ml) and rifampicin (50 µg/ml) when donor strains were NCDO712 or MG1299 (pIL253pil). Transconjugants were selected on glucose Elliker agar plates supplemented with streptomycin (100 µg/ml) and erythromycin (10 µg/ml) when donor strain was MG1363(pIL253pil). For the conjugation of pNZ712 encoding copper resistance genes from NCDO712 to MG1614 LM17 plates were supplemented with streptomycin (100 µg/ml), rifampicin (50 µg/ml) and 1.2 mM $CuSO_4$.

Results

Chromosomal differences between L. lactis NCDO712 and MG1363.

Re-sequencing of the total DNA of NCDO712 allowed the detection of 11 Single Nucleotide Polymorphisms (SNPs) between the chromosomes of L. lactis NCDO712 and its plasmid-cured derivative MG1363 (159), which was isolated in 1983 following multiple rounds of chemical- and protoplast-induced plasmid curing (95). Amongst the 11 SNPs found in the chromosome of L. lactis NCDO712, three are synonymous, three are in intergenic regions, while the other five lead to amino acid changes in proteins. The sequencing data also suggests the occurrence of genome re-arrangements but their verification was out of scope of this study.

Only one of the three SNPs in the intergenic regions is predicted to be in a promoter region, that of the mtlA gene encoding a putative mannitol-specific PTS system EIIBC component. For mtlA the differential RNA sequencing has pinpointed the transcription start site (TSS) at position 26465 (van der Meulen et al. accepted). The mutation at the position 26455 suggests that the −10 box is altered from an optimal TATAAT into TACAAT. Furthermore, three of the protein sequence-affecting SNPs in the genes encoding a hypothetical protein and 2 transposases were predicted not to affect protein function. These predictions were made using SIFT, an algorithm that analyzes the effect of mutations based on the degree of conservation of amino acid residues (113, 144). Mutation in the gapB and tsf genes encoding the glyceraldehyde 3-phosphate dehydrogenase and elongation factor TS respectively are predicted to affect the protein function. Whether these mutations are caused by genetic drift or if they confer a fitness advantage in a laboratory environment is unclear. However, the data indicate that the number of SNPs occurring between MG1363 and NCDO712 is limited.

L. lactis NCDO712 harbors six plasmids.

Assembly of all nucleotide sequence reads that did not map onto the chromosome of L. lactis MG1363 revealed that L. lactis NCDO712 carries a total of 6 rather than the previously described 5 plasmids (95). Using L. lactis NCDO712 derivatives harboring single plasmid species (95) we linked the plasmids identified here to the earlier described plasmids of this strain (Table 2). The plasmid sizes did not fully correspond to the respective sizes determined here, which this is most likely caused by the limitations of size estimation based upon agarose gel electrophoresis (95). However, we cannot exclude that plasmid rearrangements accounting for (part of) the differences have occurred during strain propagation over the years (160). The additional plasmid identified in this study, designated pNZ712, has a size similar to that of pLP712, which may explain why it escaped detection in 1983 (95).

The copy number of the individual plasmids varied between 2 and 4, based on mean coverage number of chromosomal DNA and plasmid coverage (Table). The plasmid replication mode was determined using previously described criteria (68, 119). Rolling circle replication (RCR) was identified on basis of the presence of Rep-family protein encoding genes and a double-stranded origin (dso) of replication; while a replication initiator protein encoding repB gene and an origin of replication (ori) are indicative of theta-type plasmid replication (68). These analyses indicated that pSH71 replicates through a rolling circle mechanism (68, 88), while the other 5 plasmids replicate using a theta-type mechanism (68).

Plasmids pLP712 and pSH71 have been sequenced and described earlier (88, 160). The nucleotide sequence of the pLP712 is identical to the one determined here, except for a single nucleotide difference, whereas the pSH71 sequence differs by 6 nucleotides (Table) and plasmid origin.

To investigate the relationships of plasmids pSH72, pSH73, pNZ712, and pSH74 with other known plasmids we compared them with 1.955 plasmid sequences in the NCBI database (database consulted on Feb. 1, 2015). pSH72 (3.597 bp) had the highest copy number, approximately 4 copies per cell, and only appeared to encode the replication genes repB, repX, and rep C. Except for 3 nucleotide differences pSH72 was identical to plasmid pND324 which was isolated from L. lactis subsp. lactis LL57-1 (90) (Table). The biological function of this plasmid is unclear. pSH73 is identical to pAG6, a plasmid isolated from Lactococcus lactis ssp. cremoris 712 (acession number: AB198069, GI: 70067197), which is most likely the same strain as NCDO712 or a derivative of it (97). The only SNP (A→G, pAG6→pSH73) detected is at nucleotide position 1143 of the hsdS gene encoding a type I restriction/modification system specificity subunit. Plasmid pSH73 harbours next to the replication genes repX and repB also cadCA genes that were predicted to encode a cadmium resistance regulatory protein and a cadmium efflux ATPase.

The two other plasmids pSH74 and pNZ712 were found to have partial similarity to known *L. lactis* plasmids with 93-99% nucleotide identity. Identities were found in genes encoding for several functions such as replication, transposases, resolvases, copper resistance associated genes and nisCiP of which nisi encodes nisin immunity. Detailed sequence analysis of pSH74 identified putative pilin biosynthesis genes which we annotated as spaCB-spaA-srtC1-srtC2.

TABLE 2

The comparison of NCDO712 plasmids with the earlier work.

| Plasmids described in (95) | | Plasmids annotated in this work | | | |
|---|---|---|---|---|---|
| Plasmid | Size$ | Plasmid | Size | Plasmid copy number*/ mean coverage‡ | Replication mode |
| pLP712 | 33 MDa, ~50 kb | pLP712 | 55 395 bp | 2 (423) | Theta |
| pSH71 | 1.8 MDa, ~3 kb | pSH71$^{RS}$ | 2 062 bp | 3 (673) | RCR |
| pSH72¥ | 2.5 MDa, ~4 kb | pSH72 (99% identical to pND324) | 3 597 bp | 4 (921) | Theta |
| pSH73 | 5.2 MDa, ~8 kb | pSH73 (identical to pAG6) | 8 663 bp | 3 (674) | Theta |
| pSH74 | 9 MDa, ~14 kb | pSH74 | 15 518 bp | 3 (697) | Theta |
| — | — | pNZ712 | 49 832 bp | 2 (471) | Theta |

*Estimated on the bases sequence coverage in comparison to that of the chromosomal DNA.
$Plasmid size in original publication is given in MDa. Plasmid size in kb is estimated through the relationship – 1 MDa ds-DNA = 1.52 kb (https://tools.thermofisher.com).
‡Coverage number is based on the analysis of 6 million sequence reads. Chromosomal DNA coverage in the same analysis was 198.
¥pSH72 differs by 3 bp from pND324 (90) (NCBI reference sequence: NC_008436.1): T1295G, G1384A and C3349-deleted.
$^{RS}$pSH71 sequence differs from pSH71 (NCBI accession number A09339; de Vos W.M., 1987) by 6 bp: T712-deleted, T713-deleted, A731-deleted, G803A, -deleted1234T, C1414-deleted.

Nisin immunity and copper resistance are specified by pNZ712.

Nisin is a lanthionine-containing antimicrobial peptide that binds to lipid II, disrupts the cytoplasmic membrane and causes death of susceptible bacterial cells. The nisin operon nisABTCIPRKFEG was previously described to be present on the sucrose-nisin transposon Tn5276 and carries, next to the nisin structural gene nisA, genes responsible for modification, transport and precursor cleavage, genes involved in the regulation of the nisin operon and genes specifying resistance to the bacteriocin (126, 156). Plasmid pNZ712 carries nisCiP, but nisC is only partially present. The nisC gene encodes an enzyme involved in posttranslational modification (in concerted activity with NisB) of the nisin precursor, nisi encodes nisin immunity, and nisP encodes the serine protease which is involved in maturation of the nisin precursor.

To determine if nisi is functional, *L. lactis* NCDO712 was grown in LM17 medium supplemented with 0 and 20 ng/ml nisin. *L. lactis* NZ9700 was used as a nisin resistant control. In the absence of nisin all strains reached a maximal $OD_{600}$ of 2.96±0.63 after 7 h of growth. When the strains were grown in the presence of 20 ng/ml nisin, the positive control NZ9700 reached an $OD_{600}$ of 1.8±0.06. *L. lactis* NCDO712 and SH4109, strains carrying all 6 plasmids including pNZ712 with the plasmid-encoded nisCIP, reached an $OD_{600}$ of 0.63±0.01 and 0.67±0.09, respectively. The optical density reached is less compared to NZ9700 which has the full immunity function. This difference is a lack of nisFEG, genes encoding an ABC transporter that contributes to nisin immunity in NCDO712. The plasmid-free derivative *L. lactis* MG1363 and other derivatives carrying single plasmids but not pNZ712 from *L. lactis* NCDO712 reached an $OD_{600}$ of only 0.06±0.046. Hence, the pNZ712-encoded nisi is functional and provides nisin immunity to *L. lactis* NCDO712.

To determine if the putative copper resistance genes lcoRSABC on pNZ712 are functional, *L. lactis* NCDO712 and several of its derivatives not carrying pNZ712 were grown in the presence or absence of $CuSO_4$. MG1363 showed no growth if 0.8 mM or more $CuSO_4$ was added to the medium. *L. lactis* NCDO712, harboring pNZ712 with the lcoRSABC genes, was the only tested strain able to grow in the presence of 1.2 mM $CuSO_4$, indicating that the gene cluster on pNZ712 is functional. At 2, 4 and 4.8 mM of $CuSO_4$ NCDO712 started to grow after 5, 10 and 15 hours respectively. We could also show that pNZ712 harboring the copper- and nisin-resistance genes can be transferred from one lactococcal strain to another via conjugation when copper is used as a selective marker, which corroborates the functionality of the genes.

A novel pilin gene cluster is present on pSH74.

Plasmid pSH74 was found to harbour an 8-kb gene cluster which we annotated as spaCB-spaA-srtC1-srtC2. It is flanked by IS1216 elements (FIG. 2). Different gene-orders of pilin biosynthesis genes have been reported in gram-positive bacteria (121, 154), but the gene-order found on pSH74 mostly resembles that of the spaC-spaB-spaA-srtC cluster of *Lactobacillus rhamnosus* GG (105, 134, 157) although the encoded proteins display only 30 to 45% amino acid sequence identity. In addition, the plasmid-encoded pilin cluster of pSH74 contains two adjacent srtC genes, which encode sortase C proteins of 413 and 392 amino acid residues, respectively. The two sortases are only 38% identical, and two or even three consecutive srtC genes have previously also been found in the pilin biosynthesis gene clusters in *Streptococcus agalactiae*, *S. pneumoniae*, and *Clostridium* diphteriae (89, 142). Similarly to *Lactobacillus rhamnosus* GG (89, 111, 112), srtC in *L. lactis* NCDO712 might be responsible for the assembly of pilin proteins into pili, while the chromosomally encoded srtA (llmg_1449) should recognize LPxTGE or LPxTGD motifs and covalently anchor pili to peptidoglycan of the cell wall (89).

Also similar to *L. rhamnosus* GG, the SpaA protein of *L. lactis* NCDO712 is presumably the pilin main backbone subunit. It contains the typical LPSTGGAG motif near the C-terminus for cleavage by sortase C and has the characteristic YPKN "pilin motif" with a conserved lysine residue. SpaA also carries the YVLNETKAP "E box", which is suggested to have a structural role in pilus assembly (80, 127, 144).

The spaC and spaB genes, which are separate genes in *Lactobacillus rhamnosus* GG, are fused in *L. lactis* NCDO712. In *L. rhamnosus* GG SpaB is the basal pilus subunit and SpaC is the pilin tip protein. In *L. lactis* NCDO712 the first approximately 840 amino acid residues of SpaCB correspond to SpaC, the remaining C-terminal 260 residues to SpaB. The SpaC segment in SpaCB contains an LPSTGGAG motif that could be cleaved by sortase C, possibly splitting the SpaCB into 2 separate proteins SpaC and SpaB. Moreover, predicted with PePPER (87) an alternative transcription start site downstream of the LPSTG- GAG motif of the SpaC encoding region of the spaCB gene may support independent synthesis of only SpaB. The SpaB resembling part of SpaCB contains a C-terminal LPDTGE motif that is predicted to be targeted by sortase A and serves as a peptidoglycan anchoring sequence (89, 134). RNAseq obtained under different stress conditions revealed that srtC1 and srtC2 are usually co-expressed, while there is no correlation in expression levels between the other genes of this gene cluster (van der Meulen et al. accepted).

SpaC has an "E box" (YALTETKTP) and a von Willebrand type-A domain (vWFA). The SpaC segment also contains a collagen-binding domain and two collagen-binding surface-protein-Cna B-type domains, which might be involved in bacterial adhesion to surfaces (IPR008970; SSF49478) (http://supfam.org). Taken together, these structure analyses suggest that analogous to the *L. rhamnosus* GG pilin, SpaB forms the basal pilus subunit and SpaC fulfills the tip protein function. We found based on protein comparisons similar pilus clusters are also present in *L. lactis* subsp. *cremoris* CNCM I-1631 contig_071 (accession number: AGHX01000000; LLCRE1631_01806, LLCRE1631_01807, LLCRE1631_01808, LLCRE1631_01809) (97% identity), in *L. lactis* subsp. *lactis* 1AA59 contig_056 (accession number: AZQT01000047.1 and AZQT01000000) (100% identity), as well as in the *Leuconostoc citreum* genome (accession numbers: WP_048699698, WP_048699696, WP_048699695, WP_048699693) (>90% identity). However, the sequences of those organisms are annotated as hypothetical proteins. In all three of those strains the spaCB genes are fused as well which suggests that this may be of relevance for e.g. the regulation of the protein's ratio to each other.

The *L. lactis* NCDO712 pilin operon is functional.

To examine whether the identified putative pilin genes are functional in *L. lactis*, the entire operon with its native promoter was cloned in the medium-copy number plasmid pIL253 (105), resulting in pIL253pil. Initial attempts to clone the pilin operon downstream of the nisin-inducible nisA promoter failed, and the few clones obtained carried the same internal deletion in the spaCB genes. Deletion of a similar internal fragment of 1.5 kb from the spaCB gene in pIL253pil resulted in pIL253pilΔ1 (Table 1). This deletion in spaCB leads to an out of the frame mutation shortening the SpaCB protein by 591 amino acid residues and retaining a 394-residue truncated protein. The native pilin operon as well as the one with the spaCB deletion were introduced in *L. lactis* strains MG1363 and IL1403. An obvious consequence of the plasmid-based pilin over-expression was cell aggregation and sedimentation of the culture in both strains (results for MG1363 are shown in FIG. 3). The cells also grew in chains much longer than 10 cells per chain (FIG. 4). Cells expressing the truncated version of SpaCB displayed neither cell aggregation (FIG. 3) nor cell chaining (FIG. 4).

Scanning electron microscopy (SEM) revealed that cells of *L. lactis* NCDO712 (FIG. 5, panel A) have a relatively rough surface compared to those of *L. lactis* IL1403 (FIG. 5, panel B), which were very smooth. The control strain *L. lactis* MG1363(pIL253) showed an intermediate state of surface roughness (FIG. 5, panel D). Furthermore, even though *L. lactis* NCDO712 harbors the pil operon, no pili were visible on the surface of these bacteria. The pili were seen in *L. lactis* NCDO712 only when the pIL253pil plasmid was introduced (data not shown). This indicates that the expression level of the pilin operon from the native plasmid, which was estimated to be present in 3 copies per cell, is not sufficient for the detection of pili on the cell surface. However, expression of the same operon from the plasmid pIL253, which is present in higher copy numbers (145) is sufficient to detect the pili. The introduction of pIL253pil into *L. lactis* IL1403 led to pilin-like structures, albeit at relatively low abundance (FIG. 5, panel C), whereas *L. lactis* MG1363 harbouring pIL253pil clearly carries more appendices on its cell surface (FIG. 5, panel E). In addition, an increased roughness of the cell surface was observed in both IL1403 and MG1363 when they harbour pIL253pil. Interestingly, MG1363(pIL253pilΔ1) cells expressing the truncated version of spaCB (FIG. 5, panel F) were also decorated with pilus-like structures on the surface, but these appendices appeared to be more disoriented than those present on MG1363 harbouring pIL253pil (FIG. 5, panels E and F). The observed disorientation could imply that the pili of MG1363 harbouring pIL253pilΔ1 are not appropriately attached to the peptidoglycan, which would be consistent with the prediction that the truncated spaCB lacks the predicted SrtA motif for peptidoglycan anchoring. These results revealed that expression of the spaCB-spaA-srtC1-srtC2 pilin gene cluster derived from pSH74 of *L. lactis* NCDO712 leads to the formation of pilin-like appendices on the surface of lactococcal cells.

In gram-negative bacteria the length of pili is approximately 1-2 μm, and the diameter is between 1 nm and 10 nm. In gram-positive bacteria pili have been reported to have a length of 0.3-3 μm, and a diameter of 3-10 nm (151). In *L. rhamnosus* GG the length of pili is up to 1 μm and the diameter is 1-10 nm (105). Pili in *L. lactis* IL1403 reached up to 3 μm in length and a diameter of approximately 5 nm (132). On the surface of *L. lactis* TIL448 pili were short and thin with a length up to 450 nm, but on the surface of the overexpressing strain pili became longer with average length of 2 μm and diameter of 2.3 nm (125). Interestingly, the pili overexpressed in MG1363(pIL253pil) from pSH74 of *L. lactis* NCDO712 are shorter and thicker than most others with a length of 200-240 nm and a 18-20 nm diameter, whereas pIL253pilΔ1 derived pili in MG1363(pIL253pilΔ1) were thinner with a diameter of approximately 14 nm.

Conjugation efficiency.

One of the known functions of pili in gram negative bacteria is involvement in conjugation (80). To examine whether the *L. lactis* NCDO712 pil operon might play a role in DNA transfer by conjugation, we measured the efficiency of conjugation in the presence and absence of the pil operon. *L. lactis* NCDO712 carries a sex factor in its chromosome that is involved in co-integrate formation with and subsequent conjugal transfer of the lactose/protease plasmid pLP712 (97, 99). This process can be readily quantified using the plasmid-free, lactose deficient *L. lactis* MG1614 (Lac$^-$, PrtP$^-$, Strep$^R$, RifR) (Table 1) as a recipient and selecting for lactose-fermenting colonies that are also resistant to rifampicin and streptomycin. The efficiency of transfer of pLP712 from *L. lactis* NCDO712, MG1299 and MG1363 was up to 20-, 17- and 50-fold increased upon pili overexpression, respectively (Table 3). We did not find co-transformation of pIL253pil during the conjugation of pLP712. Although the observed increase in conjugation efficiency is not very high, these observations indicated that pili might contribute to the efficacy of exchange of DNA between lactococcal cells. We do not know if this effect is caused by pili mediated cell clumping or through pili that seem to make cell to cell contact (FIG. 6).

TABLE 3

Results of conjugation experiments. In all cases the strain L. lactis MG1614 was used as the recipient. The strains with pIL253pil showed an increase in the number of transconjugants obtained per donor CFU. When strain with empty plasmid (pIL253)was tested in conjugation experiment, pili overexpression enhanced conjugation efficiency by 50 fold.

| Donor | Transconjugants per donor CFU Average | SD (n = 4) | Fold increase |
|---|---|---|---|
| NCDO712 | 1.1E−07 | 3.54E−08 | |
| NCDO712(pIL253pil) | 2.4E−06 | 1.13E−07 | 21.91 |
| MG1299 | 1.4E−07 | 4.74E−07 | |
| MG1299(pIL253pil) | 1.6E−06 | 1.11E−06 | 11.18 |
| MG1363(pIL253) | 8.3E−10 | | |
| MG1363(pIL253pil) | 4.4E−08 | | 53.01 |

Discussion

Sequencing of the total DNA of L. lactis NCDO712 revealed the presence 6 plasmids in this strain of which some specify potentially important industrial traits. Functional nisin immunity and copper resistance genes are present on pNZ712 (51.7 kb), a plasmid that was not identified in an earlier study of the plasmids of L. lactis NCDO712 (95). This newly identified plasmid possibly escaped detection because pNZ712 has a size similar to that of the lactose/protease plasmid pLP712. Plasmid-encoded copper resistance has been described previously in Streptococcus (now Lactococcus) lactis (70, 91, 119), but has not been described in L. lactis NCDO712. According to earlier studies lcoRS are regulatory genes involved in transcription of lcoABC, while lcoABC itself confers copper resistance by lowering the accumulation of copper inside the lactococcal cell (143). However, next to the lcoRSABC cluster pNZ712 also contains pNZ712_23, a protein which is annotated as copper-(or silver)-translocating P-type ATPase that could also be involved in the increased copper resistance found NCDO712. Interestingly, in Lactococcus lactis C2, a recently diverged derivative of NCDO712 (86, 114), which was reported to carry 5 plasmids, the resistance to metal ions, including copper, was suggested to be encoded on a DNA region of the lactose plasmid pLM3001 of which the sequence remains unknown (91). Our results show that copper resistance and lactose utilization genes reside on different plasmids, indicating that plasmid re-arrangements may have occurred in NCDO712, C2, or in both strains (86).

We found that pSH74 (17 kb) contains an 8-kb pilus gene cluster. Pilus genes have been described earlier in L. lactis. Oxaran and co-workers (132) identified a chromosomally encoded pilus gene cluster in L. lactis IL1403, which was initially based on sequence analyses and homology searches to characterized pilus and sortase proteins. Similar to our work with NCDO712, detectable production of pili could only be achieved by overexpression of the pilus genes yhgD, yhgE, yhhA, yhhB in the same strain. For overexpression they used the medium-copy number vector pIL253 and the constitutive promoter P23, rather than its native promoter as we have used here. The native promoter region of spaCB seemed important for successful expression/cloning of the pilus gene cluster, since expression without leader resulted in deletions in spaCB after expression from other a nisin inducible and the constitutive purC promoter. The strategy with the native promoter was followed after observing a leader sequence of ~200-nt upstream of spaCB by visualizing RNA-seq data by Rockhopper (123) (van der Meulen, accepted). Based on negative staining and TEM analysis Oxaran et. al. detected pili under standard laboratory conditions in other L. lactis isolates. These were vegetable isolates such as KF282 and NCDO2118, as well as clinical isolates such as 2885-86 and 810-85. Interestingly, the chromosomally encoded pilus gene cluster yhgD, yhgE, yhhA, yhhB of IL1403 appeared to be present in all lactococcal genomes known to date, including those of L. lactis strains SK11, KF147, and MG1363 (llmg_1800-1803) (132).

In another study L. lactis TIL448 was shown to carry a plasmid-encoded 6.9-kb pilus gene cluster, yhgE2-srtC2-yhhB2-ORF4, that lead to the formation of pili at the cell surface (125) when overexpressed in either L. lactis MG1363 or in the wild type strain TIL448. Within this cluster yhgE2 was predicted to encode the pilus backbone, while srtC2 was proposed to facilitate pilin polymerization. ORF4, the putative pilus tip protein, contained a lectin-like domain (PF00139) predicted to have carbohydrate-binding properties, that were proposed to allow bacterial binding to plant cell walls. In addition, expression of yhgE2-srtC2-yhhB2-ORF4 was shown to increase the attachment of L. lactis TIL448 to intestinal epithelial Caco-2 cells (132).

For the pilus cluster identified in NCDO712 we could neither find homologies at the protein level nor in the organization of the pilus gene clusters when compared to those of L. lactis IL1403 or TIL448. Besides the differences at sequence level and operon organization, the pilus length and diameter seems to differ from most earlier identified lactococcal pili (125, 132, 151).

Comparing to well described pilus clusters the gene organization in NCDO712 is closest to that of the pilus operon of L. rhamnosus LGG (86, 146). The GC content in the L. lactis NCDO712 pilus operon (35.3%) to that of the rest of the genome (35.7%) suggests that the acquisition of the pilus gene cluster is not a recent event or has been transferred from a microbial species with a similar GC content. The latter explanation may be supported by the presence of a highly homologous pilus cluster in the genome of Leuconostoc citreum (>90% protein identity) with a GC content of 38.9%.

Based on gene homology and organization we hypothesize that the function of the pilin genes of L. lactis NCDO712 is similar to those in Lb. rhamnosus GG (86, 146) and other Gram-positive bacteria (108, 122, 133, 144). Pilus formation and attachment to peptidoglycan in Lactobacillus rhamnosus GG is governed by the pilin-specific sortase SrtC1 and the house-keeping sortase SrtA. The pilin-specific sortase C specifically targets a triple glycine motif LPxTGGxG at N-terminal end of pilin protein, and catalyzes the assembly of pilin proteins into pili (89, 121). The chromosomally encoded enzyme sortase A targets N-terminal LPxTGE or LPxTGD motifs (89) and catalyzes the covalent anchoring of extracellular proteins, including pilin proteins, to peptidoglycan in the cell wall. The sortase A recognition sequence does not necessarily prevent its recognition by a sortase other than SrtA (89). It means that sortases A and C may each be able to recognize both LPxTGD/E and LPxTGGxG motifs used for the regulation of pilin biosynthesis polymerization and anchoring (89), but the protein-structural features involved in motif recognition by sortases still remain unclear. For example, when spaA-srtC1 of Lb. rhamnosus GG were co-expressed in L. lactis NZ9000, it was observed that SrtC1 can recognize and polymerize the SpaA protein as well as pilus tip protein SpaC, while SrtA is only involved in anchoring of SpaB to the peptidoglycan. *Lb. rhamnosus* GG also carries a pilus gene cluster, spaFED, on its chromosome, where SpaD is the pilus backbone protein and SpaE is located at the base of the pilus structure, like SpaB (135, 157). SpaF, similar to SpaC, is the minor pilin subunit that locates to the tip of the pilus and was shown to be responsible for adhesion of pili-carrying cells to the intestinal mucus (137). *L. lactis* NCDO712 SpaA and SpaC contain the LPxTGGxG motif in its C-terminus for cleavage by the pilin-specific sortase C for further formation of isopeptide bonds to interconnect these pilin subunits. SpaA also carries the "E box" and YPKN "pilin motif". The "E box" is suggested to have a structural role in pilus assembly (80, 127, 144) as is illustrated by the involvement of the "E box" of SpaA from *Corynebacterium diphtheria* in the attachment of SpaB to polymerized SpaA fibres (87). The "pilin motif" is involved in intermolecular peptide bond formation between the carbonyl-group carbon of the threonine residue of the pilin subunit and the side-chain of the lysine in pilin motif of the neighboring pilin subunit (151). These bonds lead to the formation of membrane-associated covalently-linked dimer with a pilin motif that can interact with other pilin subunits, forming a elongated pilus fibre (151). Thereby, the presence of an E-box, LPxTGGxG and YPKN motifs in *L. lactis* SpaA suggests that this protein constitutes the major pilin backbone subunit.

As we described earlier the SpaC segment of SpaCB contains an LPxTGGxG SrtC motif we hypothesize that after cleavage of SpaCB by SrtC, the "E box" would link SpaC to SpaA proteins. It has been speculated that the vWFA domain, which is also present in SpaC of *L. rhamnosus* GG (105), may have lectin-like binding properties and could bind to sugars with high carbohydrate specificity. The SpaB segment in SpaCB carries the canonical LPxTG motif for cleavage and linkage to peptidoglycan by sortase A. Hence, SpaB is most likely at the base of the lactococcal pilus, and SpaC is the pilin tip protein. An internal deletion in spaCB led to the formation of much more, albeit aberrant and somehow disoriented, pili at the surface of the cells, which would be in agreement with a lack of the proper attachment of the pili via the basal subunit SpaB.

Since the *Lactobacillus rhamnosus* GG pilus operon is involved in attachment to human intestinal epithelial cells, Caco-2, we tested if the pilus operon identified here confers similar binding properties. However, no significant differences in attachment to Caco-2 or HT29 (a human colonic carcinoma cell line) cells were observed between stationary-phase cells of *L. lactis* NCDO712 or *L. lactis* either with or without pIL253pil (data not shown). The level of adherence of lactococcal cells was relatively low as compared to the level of adherence displayed by the *Lb. rhamnosus* GG cells that were used as a control in these experiments.

Cell aggregation or close-proximity is an important factor for conjugative plasmid transfer. Conjugative plasmid transfer in gram-positive cocci was studied (79, 101, 141), including lactococci (75, 141, 147), but there was no report on the role of pili in this process. Since pili overexpression leads to increased cell-clumping and we also observed direct cell-cell contact via pili in SEM images, we investigated the impact of pili expression on plasmid transfer frequencies and conclude that pili expression can enhance frequency of transconjugation by a factor of 11- to 53-fold per donor cell CPU. The underlying mechanisms remain unknown, but the pilin tip protein SpaC could bind to another cell, keeping the two cells in close proximity (80). Such close proximity of cells could facilitate and increase the conjugation frequency. We also cannot exclude that pili could enable conjugation of genetic material to other species.

Example 2. Bacteria as Structural Elements in a Fermented Food Product; Alteration of Lactococcal Surface Properties and its Functional Consequences on Fermented Milk Introduction Lactic acid bacteria (LAB) are gram-positive bacteria that are generally regarded as safe and they are used extensively in food and feed fermentations. They are also found on mucosal surfaces of humans and animal (34, 57). One of the dominant features during fermentation processes with LABs is that they produce lactic acid as the main metabolic end product and this leads to rapid acidification and hence preservation of the fermented material. An additional functionality of many strains is the production of volatile metabolites that are important flavour compound (51, 53). In fermentation the bacteria can also play an significant role in altering textural properties of the material through e.g. proteolytic activity or the production of extracellular polysaccharides (50).

In general the structure of fermented dairy products is very complex, consisting of caseins, whey proteins, fat droplets, serum or whey pockets, minerals, salts and microorganisms. Throughout this paper we refer to this structure as the matrix. In such a matrix interactions between milk components and their functionality are studied extensively (14, 24, 31, 35, 46). For example, the rheological properties of a milk gel depend on the size and number of fat droplets and the nature of available emulsifiers (43). If the matrix is stabilized by low molecular weight surfactants, then the milk gel is weak and has a high meltability, the extent to which gel flows and spreads upon heating, because the surface of fat droplets is smooth and non-interactive. However, if fat droplets are stabilized by whey proteins, then the milk gel is strong and has a low meltability because protein-protein cross-linking interactions are formed between emulsified fat droplets. Other interactions in the food matrix can be hydrophobic (6), electrostatic (11), hydrogen bonding (64), Van der Waals, depletion interaction (59), steric repulsion (16) and salt bridges (5).

In contrast to interactions between the milk components themselves very little is known about so called microbe-matrix interactions which describe the interaction between lactic acid bacteria and matrix components of the fermented products (7-10, 47).

Interactions between microorganisms and milk components occur via surface properties of both particles. Bacteria as well as matrix components have a charge and hydrophobicity. The surface properties of bacteria are determined by molecular composition of its cell wall, which can be decorated with (lipo-) teichoic acids, proteins, pili, or (exo/capsular)polysaccharides (EPS/CPS) (13, 22, 45). The molecular composition of the cell wall has a significant impact on the roughness of the bacterial surface, on bacterial chaining and on cell aggregation (see example 1). These properties govern the interactions between bacteria and the food matrix (7, 41). A well-studied example of a change in textural properties is the production of EPS by the bacterial culture used for the fermentation. EPS are hydrocolloids that can bind high amounts of water and therefore, increase milk ropiness and water holding capacity in protein-free pores of the fermented milk matrix. This leads to an increase in milk viscosity and it reduces syneresis (2, 26, 48). Additionally, the charge, stiffness and linearity of EPS molecules impact on rheological and physical properties of the fermented milk matrix. EPS modification by partial removal of side groups leads to its reduced efficiency as thickener (58).

Besides the role of EPS on textural properties of fermented milk little is known about the influence of bacterial surface properties on interactions with the matrix and its functional consequences on flavour and texture.

We here studied how the alteration of bacterial surface properties affect textural parameters and flavour volatiles of fermented milk. This was achieved by using 25 isogenic *L. lactis* strains which only differed in known surface properties and cell morphologies. We have found that particular surface alterations not only lead to distinct differences in gel hardness and viscosity of fermented milk but also to significant alterations in some flavour volatiles. Therefore, based on our results we conclude that bacteria can be used as structure elements in fermented foods.

Materials and Methods

Bacterial Strains and Growth Conditions

*L. lactis* was grown in M17 broth (Oxoid Ltd, Basingstroke, Hampshire, UK) supplemented wither with 1% glucose (GM17) or with 1% lactose (LM17) at 30° C. When required, erythromycin (Ery; 10 µg/ml), chloramphenicol (Cm; 5 µg/ml), rifampicin (Rif; 50 µg/ml), or streptomycin (Str; 100 µg/ml) were added to the indicated end-concentrations.

TABLE 4

Strains and plasmids used in this study.

| No | *L. lactis* strains | Characteristic | Reference |
|---|---|---|---|
| 1 | NCDO712 | *L. lactis* dairy isolate, lac⁺, contains 6 plasmids-pLP712, pSH71, pSH72, pSH73, pSH74, pNZ712. | (19), example 1 herein |
| 2 | NCDO712 (pIL253pil) | Ery$^R$; harboring pIL253 with pilin operon spaCB-spaA-srtC1-srtC2 from NCDO712 | example 1 herein |
| 3 | MG1363 | Plasmid-cured derivative of *L. lactis* NCDO712 | (19) |
| 4 | MG1363 (pIL253pil) | Ery$^R$; *L. lactis* MG1363 harboring pIL253 with pilin operon spaCB-spaA-srtC1-srtC2 from NCDO712 | example 1 herein |
| 5 | MG1363 (pIL253pilΔ1) | Ery$^R$; *L. lactis* MG1363 harboring pIL253 and pilin operon spaCB-spaA-srtC1-srtC2 from NCDO712 with 1,5-kb internal deletion in spaCB | example 1 herein |
| 6 | MG1299 (pIL253pil) | Ery$^R$; *L. lactis* lac⁺ derivative of NCDO712 which additionally to pLP712 harboring the pilin operon (spaCB-spaA-srtC1-srtC2) from the same NCDO712 strain | example 1 herein |
| 7 | MG1299 | Derivative of *L. lactis* NCDO712, harbors pLP712; lac⁺ | (19) |
| 8 | MG1362 | Derivative of *L. lactis* NCDO712 (described to harbor pSH72) | (19) |
| 9 | MG1063 | Derivative of *L. lactis* NCDO712 (described to harbor pSH73 and pSH72) | (19) |
| 10 | MG1261 | Derivative of *L. lactis* NCDO712 (described to harbor pSH73) | (19) |
| 11 | MG1365 | Derivative of *L. lactis* NCDO712 (described to harbor pSH71) | (19) |
| 12 | MG1614 | Str$^R$ and Rif$^R$; derivative of *L. lactis* MG1363 | (19) |
| 13 | MG1614_clu⁺ | lac⁺. Transconjugant of MG1614, harbors pLP712 from NCDO712 and shows clumping phenotype. | example 1 herein |
| 14 | MG1614_clu⁻ | Lac⁺ Transconjugant of MG1614, harbors pLP712 from NCDO712 and show non-clumping phenotype. | example 1 herein |
| 15 | MG1363ΔacmA | Derivative of *L. lactis* MG1363 with deletion of acmA, which leads to chaining phenotype | (55) |
| 16 | MG1363ΔahrC | Derivative of *L. lactis* MG1363 with deletion of ahrC | (32) |
| 17 | IL1403ΔacmAacmD | Derivative of *L. lactis* IL1403 with deletion of acmAacmD, which leads to chaining phenotype | (63) |
| 18 | IL1403(pIL253pil) | Ery$^R$; Derivative of *L. lactis* IL1403 harboring pilin operon from pSH74 of NCDO712; shows chaining phenotype and high hydrophobicity | example 1 herein |
| 19 | MG1363ΔdltD | Derivative of *L. lactis* MG1363 with deletion of dltD | (15, 56) |
| 20 | MG1363(pIL253) | Ery$^R$; Derivative of *L. lactis* MG1363 harboring plasmid pIL253 | example 1 herein |
| 21 | IL1403 | Plasmid-free derivative of *L. lactis* IL594 | (4) |
| 22 | MG1363pNZ521 (pIL253pil) | Cm$^R$ and Ery$^R$; derivative of *L. lactis* MG1363 harboring pNZ521 and pIL253pil (spaCB-spaA-srtC1-srtC2) from the NCDO712 strain | example 1 herein |
| 23 | MG1363pNZ521 | Cm$^R$; derivative of *L. lactis* MG1363 harboring proteolytic positive genes on pNZ521 | (44) |
| 24 | MG1363ΔgalE | Derivative of *L. lactis* MG1363 with deletion of galE leading to chain formation without galactose in a growth medium | (23) |

TABLE 4-continued

Strains and plasmids used in this study.

| No | L. lactis strains | Characteristic | Reference |
|---|---|---|---|
| 25 | MG1363pNZ4120 | Ery$^R$; derivative of L. lactis MG1363 harboring EPS gene cluster from B40 | (3) |
| | | Plasmids | |
| 1 | pIL253pil | Ery$^R$; 13.1 kb; pIL253 harboring pSH74 pilin operon spaCB-spaA-srtC1-srtC2 with 300 bp upstream region | example 1 herein |
| 2 | pIL253p/IΔ1 | Ery$^R$; 11.6 kb; pIL253 harboring spaCB-spaA-srtC1-srtC2 with 1,5-kb internal deletion in spaCB | example 1 herein |
| 3 | pNZ521 | Cm$^R$; encodes the extracellular serine proteinase (PrtP) from strain SK110 | (44) |
| 4 | pLP712 | The 55.39 kb plasmid encoding genes for lactose catabolism and a serine proteinase involved in casein degradation | (65) |
| 5 | pIL253 | Ery$^R$; 4.9 kb; Low copy-number derivative of pAMβ1 | (49) |
| 6 | pNZ4120 | Em$^R$; pIL253 derivative containing a 17-kb NcoI fragment carrying the eps gene cluster from NIZO B40 | (3) |

For experiments carried out in milk, full fat pasteurized and homogenized milk (3.6 g/100 ml fat, 3.5 g/100 ml protein, 4.7 g/100 ml lactose) (Friesland Campina) was purchased from a local shop and sterilized at 115° C. for 15 min to denature whey proteins and aggregate them with caseins and fats (9). Milk was supplemented with sterile 50% glucose solution (4% final concentration) and sterile 20% Bacto™ Casitone (Pancreatic digest of casein, BD, Sparks, Md., USA) solution to 0.2% final concentration to ensure growth of lactose and protease negative strains respectively. For lactose and protease positive strains this supplementation was replaced by the addition of the same volume of water to the milk. The warm (30° C.) milk was inoculated with 2% v/v overnight culture.

Milk acidification rate and pH.

Acidification rates and final pH were measured with a Cinac 14 ph+2T (Alliance instruments, Freppilon, France). pH electrodes were inserted into 10 ml tubes with inoculated milk and samples were measured for 21 h at 30° C. every 6 min.

Sedimentation profile of fermented milk.

400 µl of inoculated milk were transferred into LUMi-Fuge rectangular 2 mm synthetic cells (www.lum-gmbh.de). The cuvettes were incubated statically for approximately 21 hours at 30° C. Non-inoculated milk was used as a control. Sedimentation profiles of the fermented milk samples were determined using a LUMiFuge® 110-02 Technology (LUM GmbH, Berlin, Germany) according to the manufacturer's instructions. The rectangular synthetic cells (2 mm, PC) with 400₁11 fermented milk were centrifuged at 2325 g at 20° C. for 1 h. The measurement interval of the optical density along the cuvette was 30 sec, which created 121 profiles. The light factor was 2. The sedimentation rates of the samples were calculated using SepView5 to determine the slope of the integrated transmission change in time. Slopes with the highest fit (r>0.98) were used for sample comparison.

Matrix structure visualized with confocal laser scanning microscopy (CLSM).

One ml homogenized milk was supplemented 15 µl of a solution of 0.5% Acridine Orange and 0.025% Rhodamine B to stain proteins and fat droplets. This milk was inoculated with 1% overnight culture and 1 µl Syto 9 (non-diluted solution) was directly added to the sample to stain the bacterial cells. The inoculated milk sample was transferred to a CLSM slide with a cylindrical plastic cup attached to it which was then covered with a lid (ref to Hassan 1995) to prevent evaporation. The sample was incubated for 21 h at 30° C.

Images were taken using a Leica TCS SP 5 confocal laser scanning microscope (Leica Microsystems CMS GmbH, Mannheim, Germany) with Leica application Suite Advanced Fluorescence v. 2.7.3. build 9723. The Argon laser was used to visualize the bacteria stained with Syto9, and DPSS 561 laser was used to visualize milk protein/fat droplet matrix stained by Acridine Orange and Rhodamine B. The objective lens used was HCX PL APO 63×/1.2/water CORR CS.

Volatile compounds with GC-MS.

After the gel hardness measurements the milk samples (2.1 g) were transferred to a 10-mL dark brown glass headspace vial and were kept at −20° C. until analyzed. After sample thawing, 50 µl of internal standard (trichloropropane 5 ppm) was added to each sample. Volatile compounds were measured as earlier described (11) with the following changes. We used a Solid Phase Micro Extraction (SPME) extraction method with a grey fiber (Carboxen/polydimethylsiloxane/divinylbenzene, Supelco, USA) for 20 minutes at 40° C. The compounds were separated on a 30 m×0.25 µm FactorFour column (Agilent, The Netherlands) with a 1 ms (df=1 µm) stationary phase. The total run time, including cooling, was approximately 36 min Mass spectra were recorded by a DSQ mass spectrometer (Thermo Fisher Scientific Inc.). The fingerprints (chromatograms) were studied to detect differences in volatile compounds between the samples (control strain and derivatives). Peaks that were different between samples were identified using the NIST MS Search library version 2.0. For those peaks that could be identified the peak area was calculated using the software package Xcalibur (Thermo).

Gel strength of fermented milk.

The bacterial strains were pre-cultured overnight in milk supplemented with the appropriate antibiotic if required. For the gel strength and viscosity measurements, 300 ml milk was inoculated with 2% of the strains pre-cultured as described above. The 300 ml milk samples did not contain any antibiotics to minimize differences between samples. The prepared milk was distributed to 100 ml sterile glass cups (70 mm diameter). The cups were incubated statically for 21 hours at 30° C.

Gel strength was measured with a Texture Analyzer (TA.XTplus, Stable Micro Systems Ltd., Sprundel, NL) equipped with a 5 kg load cell. 100 ml of fermented milk Results Surface Altered Lactococci To investigate if changes in cell surface properties affect product functionality, we performed assays using isogenic *Lactococcus lactis* strains that differed in surface charge, hydrophobicity, chaining, clumping, attachment to proteins, pili expression and EPS production (Table 5).

TABLE 5

Phenotypic characteristics of *L. lactis* strains (n = 3) in a stationary growth phase at pH of 6.7. Charge has negative values and is shown in mV, CSH stands for cell surface hydrophobicity, Att_NaCN-for attachment to sodium caseinate, Att_NaNC90C-for attachment to sodium caseinate heated at 90° C. for 10 mm, Att_ParaCN-for attachment to paracaseinate, and E24 means emulsion stability after 24 h.

| *L. lactis* | ZP, mV | CSH, % | Att_NaCN, % | Att_NaCN90C, % | Att_ParaCN, % | E24, % |
|---|---|---|---|---|---|---|
| Pili overexpressing strains are chaining and clumping | | | | | | |
| IL1403 | −9.2 ± 0.5 | 0 ± 19.89 | 41.65 ± 13.59 | 67.22 ± 2.24 | 63.66 ± 1.56 | 0 ± 0 |
| IL1403(pIL253pil) | −13.87 ± 1.25 | 93.24 ± 4.47 | 1.79 ± 0.66 | 0 ± 0 | 29.36 ± 15.34 | 88.89 ± 19.25 |
| MG1299 | −30.25 ± 2.05 | 75.48 ± 3.26 | 82.83 ± 2.7 | 82.71 ± 0.27 | 79.23 ± 2.16 | 35.6 ± 24.85 |
| MG1299(pIL253pil) | −18.1 ± 1.29 | 99.06 ± 1.16 | 27.9 ± 24.22 | 0 ± 0 | 30.22 ± 52.34 | 99.33 ± 0.58 |
| MG1363pIL253 | −26.4 ± 1.8 | 3.75 ± 6.84 | 17.7 ± 8.65 | 37.86 ± 25.39 | 80.56 ± 6.19 | 0 ± 0 |
| MG1363(pIL253pil) | −11.87 ± 0.21 | 94.03 ± 2.16 | 4.61 ± 2.93 | 1.88 ± 0.59 | 6.12 ± 10.59 | 85.24 ± 15.01 |
| MG1363pNZ521 | −31.67 ± 0.76 | 18.74 ± 10.9 | 90.34 ± 2.76 | 88.82 ± 2.43 | 79.17 ± 8.96 | 0 ± 0 |
| MG1363pNZ521 (pIL253pil) | −16.97 ± 1.89 | 99 ± 1.04 | 0 ± 0 | 0 ± 0 | 0 ± 0 | 65.56 ± 29.88 |
| NCDO712 | −19.7 ± 0.46 | 99.44 ± 0.32 | 96.02 ± 0.64 | 95.68 ± 2 | 94.74 ± 0.6 | 99.67 ± 0.58 |
| NCDO712 (pIL253pil) | −20.5 ± 1.3 | 96.31 ± 0.62 | 1.74 ± 0.5 | 37.95 ± 9.96 | 35.08 ± 16.81 | 100 ± 0 |
| Chaining phenotype | | | | | | |
| IL1403ΔacmAacmD | −12.03 ± 0.35 | 9.48 ± 4.58 | 97.17 ± 0.6 | 96.24 ± 2.07 | 96.37 ± 1.27 | 0 ± 0 |
| MG1363ΔacmA | −31.4 ± 1.42 | 15.53 ± 4.48 | 88.95 ± 0.68 | 87.56 ± 0.97 | 83.51 ± 9.96 | 0 ± 0 |
| MG1363ΔgalE | −28.73 ± 0.76 | 14.91 ± 4.44 | 94.24 ± 2.05 | 95.63 ± 0.53 | 37.49 ± 24.57 | 0 ± 0 |
| MG1363ΔdltD | −29.17 ± 0.21 | 15.38 ± 3.52 | 84.94 ± 0.62 | 83.91 ± 3.05 | 82.4 ± 3.16 | 0 ± 0 |
| Non-chaining, non-clumping phenotype | | | | | | |
| MG1363 | −30.2 ± 0.66 | 5.78 ± 0.2 | 82.3 ± 0.9 | 82.77 ± 1.95 | 79.38 ± 1.73 | 0 ± 0 |
| MG1261 | −30.03 ± 1.16 | 21.76 ± 0.2 | 93.96 ± 1.39 | 92.55 ± 0.83 | 88.76 ± 6.29 | 0 ± 0 |
| MG1063 | −29 ± 0.87 | 16.67 ± 0 | 89.47 ± 2.64 | 89.61 ± 2.05 | 83 ± 5.07 | 0 ± 0 |
| MG1362 | −31.67 ± 3.25 | 5.56 ± 9.62 | 89.58 ± 3.43 | 84.93 ± 9.73 | 79.62 ± 14.1 | 0 ± 0 |
| MG1365 | −30.33 ± 1.16 | 28.59 ± 6.12 | 92.92 ± 1.76 | 93.1 ± 1.27 | 76.6 ± 26.36 | 0 ± 0 |
| MG1614_clu⁻ | −39.4 ± 0.5 | 73.85 ± 4.05 | 96.34 ± 0.88 | 94.64 ± 0.63 | 89.4 ± 4.95 | 0 ± 0 |
| MG13634ahrC | −29.53 ± 1.21 | 79.93 ± 10.68 | 84.47 ± 1.12 | 81.01 ± 2.73 | 80.24 ± 1.68 | 23.81 ± 2.06 |
| MG1363 (pIL253pilΔ1) | −16.93 ± 0.87 | 79.67 ± 16.92 | 66 ± 10.93 | 64.53 ± 14.39 | 86.28 ± 5.22 | 97.78 ± 3.85 |
| Clumping phenotype | | | | | | |
| MG1614 | −41.97 ± 2.43 | 20.39 ± 3.12 | 97.12 ± 0.8 | 94.83 ± 4.11 | 97.66 ± 1.25 | 0 ± 0 |
| MG1614_clu⁺ | −35.97 ± 0.4 | 90.18 ± 3.74 | 81.69 ± 15 | 58.13 ± 26.29 | 94.6 ± 0.64 | 31.33 ± 4.04 |
| EPS producing | | | | | | |
| MG1363 | −30.2 ± 0.66 | 5.78 ± 0.2 | 82.3 ± 0.9 | 82.77 ± 1.95 | 79.38 ± 1.73 | 0 ± 0 |
| MG1363pNZ4120 | −18.8 ± 2.19 | 0 ± 23.76 | 96.17 ± 1 | 98.27 ± 0.52 | 97.37 ± 0.15 | 0 ± 0 | were compressed uniaxially to a depth of 20 mm with a constant speed of 1 mm/sec by a probe with a grid-like geometry having 10 mm side squared openings. The peak force applied on the sample corresponds to the hardness of the milk gel.

Viscosity of fermented milk.

After the texture analysis, the viscosity of the fermented milk was measured with a rotational viscometer (Haake Searle RV20 Rotovisco and RC 20 Rheocontroller, ThermoScientific, Hofheim, Germany) with MV2P (middle viscous profiled) rotor. 60 g fermented milk was transferred to the MVP cup and allowed to rest for 15 min After resting the sample was measured at the shear rate gradually increased from 0 to 400 s$^{-1}$ for 5 min and then decreased from 400 to 0 s$^{-1}$ for 5 min The 25 strains included variants with different plasmids from the dairy isolate NCD0712 and strains in which particular genes were deleted or over-expressed. Deletion of acmA, acmAacmD, dltD and galE lead to a cell chaining and introduction of pNZ4120, a plasmid encoding the EPS gene cluster from *L. lactis* NIZO B40, lead to EPS production in MG1363 and an increased surface charge. We recently isolated transconjugant strains of MG1614 obtained by conjugation of the plasmid pLP712 from NCDO712. (Tarazanova et al. manuscript in preparation) (4). All transconjugants isolated during these experiments were indeed shown to carry the protease/lactose plasmid pLP712 (12). However, although there was transfer of pLP712 other changes occurred as two other phenotypes we found one which gives loose cocci and has a high surface hydrophobicity (designated MG1614_clu⁻), and the other phenotype which showed a clumping phenotype and the same high hydrophobicity (designated MG1614_cl$^+$) (Tarazanova et al. manuscript in preparation). Other MG1363 derivatives such as MG1365, MG1362, MG1063, MG1261, MG1299 differ from MG1363 by carrying of 1 or 2 plasmids from NCDO712 (shown in Table 4). Recently identified is a lactococcal gene cluster encoding the spaCB-spaA-srtC1-srtC2 genes whose overexpression results in the appearance of pili like structures on the cell surface (example 1). This pili expression results in chain formation, cell clumping and a high surface hydrophobicity. A strain with an internal deletion of 1.5 kb in spaCB (designated as MG1363 (pIL253pilΔ1)) does not show chaining and clumping but it retains high cell surface hydrophobicity. In this strain pili seem to be expressed but are not attached to the cell surface. These strains have also been used in this analysis (Table 5).

Acidification Rates

As the acidification rate and the final pH during milk fermentation can influence textural properties we followed the pH for all strains during 21 h of milk fermentation (Table 6). Fast acidification of milk results in excessive syneresis, while very slow milk acidification leads to a formation of a weaker gel (21, 33, 36-39). While the maximum acidification rates for most strains were ~0.5 pH/h, strains showing a chaining phenotype (MG1363ΔacmA, MG1363 AgalE) the pilin harboring strain MG1363(pIL253pil) and its control strain MG1363(pIL253) had slower maximum acidification rates (Table 6). The final pH for all milk samples fermented by derivatives of L. lactis MG1363 strains was 4.25±0.04, with the exception of the proteolytic positive strain harboring pili MG1363pNZ521(pIL253pil) and strain IL1403 and derivatives.

TABLE 6

End pH and maximum acidification rate for selected L. lactis strains

| L. lactis strain | pH | Max acidification rate (pH/h) |
| --- | --- | --- |
| NCDO712 | 4.24 ± 0.06 | −0.51 |
| MG1363 | 4.24 ± 0.05 | −0.53 |
| MG1362 | 4.2 ± 0.04 | −0.52 |
| MG1063 | 4.19 ± 0.05 | −0.53 |
| MG1261 | 4.21 ± 0.05 | −0.54 |
| MG1365 | 4.2 ± 0.05 | −0.50 |
| MG1363(pIL253) | 4.29 ± 0.05 | −0.36 |
| MG1363(pIL253pil) | 4.23 ± 0.05 | −0.39 |
| MG1299 | 4.23 ± 0.05 | −0.49 |
| MG1299(pIL253pil) | 4.27 ± 0.05 | −0.54 |
| MG1363ΔacmA | 4.24 ± 0.05 | −0.42 |
| MG1363ΔahrC | 4.28 ± 0.03 | −0.56 |
| MG1363ΔdltD | 4.24 ± 0.05 | −0.52 |
| MG1363ΔgalE | 4.21 ± 0.05 | −0.45 |
| MG1614 | 4.23 ± 0.05 | −0.54 |
| MG1614(pLP712)_clu$^+$ | 4.27 ± 0.05 | −0.50 |
| MG1614(pLP712)_clu$^-$ | 4.27 ± 0.06 | −0.50 |
| MG1363pNZ4120 | 4.34 ± 0.07 | −0.53 |
| MG1363pNZ521(pIL253pil) | 4.77 ± 0.04 | −0.46 |
| MG1363pNZ521 | 4.22 ± 0.05 | −0.49 |
| IL1403 | 4.45 ± 0.02 | −0.53 |
| IL1403ΔacmAacmD | 4.39 ± 0.01 | −0.51 |
| IL1403(pIL253pil) | 4.47 ± 0.01 | −0.51 |

Sedimentation profiles (LUMiFuge).

To investigate the influence of cell surface properties on milk stability, sedimentation profiles were measured. The principle of the measurement is that transmission of the sample is measured over the complete height of a cuvette in time during centrifugation of the cuvette. If a milk sample is stable, particles adsorb the light, and transmission remains low over the complete sample size. If the sample is not stable during centrifuging, sedimentation from the top to the bottom of cuvette is detected through an increase in transmission on the cleared part of the sample. Our results indicate a low sedimentation slope for milk fermented with the EPS producing MG1363pNZ4120 which is consistent with the fact that EPS binds water molecules, and therefore, exhibits lower syneresis and high viscosity (2, 3, 5, 8). We found that neither the over-expression of pili on surface of lactococcal bacteria nor cell chaining or clumping did affect the sedimentation profile when compared to control strains.

Localization of cells in fermented milk.

To investigate if alterations of the bacterial cell surface affect the location of cells in fermented milk we used confocal laser scanning microscopy (CLSM). Images from undisturbed coagulated milk were taken from samples that were fermented on the imaging slide itself. Due to the sedimentation of cells during the fermentation and the limited depth at which CSLM allows imaging (~40 μm) the number of cells in the image might be higher than in the middle of a sample. However, the visualized effect of surface properties on the bacterial location in a fermented dairy product is indicative for what occurs throughout the product. Imaging of the undisturbed fermented milk therefore provides information of the behavior of the bacteria in situ, as the components and the undisturbed structure of the fermented product can be observed. The results showed obvious differences between various strains. For example loose cocci and clumping cocci locate in the protein matrix close to serum regions (FIGS. 7, A and C); aggregated cells of MG1363(pIL253pil) tightly fill the cavities between the coagulated proteins in fermented milk (FIG. 7, B); chaining cells localize in a freeway in milk matrix: go through proteins and serum regions as well as locate in close proximity to those regions (FIGS. 7, D and E); EPS producing cells locate in serum regions (FIG. 7, F). Interestingly, the localization effect of pilin over-expression in MG1363 was not observed in strain IL1403 indicating that such effect might be background dependent. Overall CLSM results indicate that the surface properties can have a profound effect on the bacterial location in the food matrix.

Flavour volatiles.

To determine the effect of altered surface properties on flavour volatiles of fermented milk we analyzed the volatile compounds in the headspace of fermented milk using GC-MS. The analysis resulted in some statistically significant changes in flavour volatiles. For example, pili over-expression led to chaining and clumping and statistically significantly increased the formation of flavour volatiles during milk fermentation. This phenomenon might be explained by highly increased (>90%) hydrophobicity, and the bacteria with more hydrophobic surfaces have a bigger affinity for aroma compounds (7). However, because the magnitude of the differences is limited, less than 10 fold, all significant differences in flavour can probably not be perceived. This means that with the present invention the texture of fermented milk can be changed without changing the flavour.

Gel hardness.

We measured gel hardness and viscosity to determine if cell surface properties influence the rheological parameters of fermented milk. The gel hardness for MG1363 (pIL253pil) increased by approximately 46% compared to control MG1363(pIL253) (p=0.009). A similar trend was observed for a proteolytic-positive strain overexpressing pili (MG1363pNZ521(pIL253pil)) which increased the milk gel strength by 15% (p=0.04). For other three strains NCDO712

(pIL253pil), MG1299(pIL253pil), and IL1403(pIL253pil) the gel hardness did not change compared to their control strains (p>0.05). The results for IL1403(pIL253pil) could be explained by very low amount of pili on the surface of this bacteria compared to MG1363(pIL253pil). We would like to note that the acidification rates were similar for the samples MG1363(pIL253) and MG1363(pIL263pil) and for proteolytic positive samples MG1363pNZ521 and MG1363pNZ-521(pIL263pil), and can, therefore, be excluded as influencing factor on gel hardness. We also investigated if the combination of pili producing strains with EPS producers in the same fermentation leads to synergy effects on gel hardness, but did not find such effects (Table 7).

Gel hardness measurements showed that it is significantly altered by using cells that either form chains or have a clumping phenotype. IL1403ΔacmΔacmD, a chain forming derivative of IL1403, decreased the gel hardness when compared to its control strain IL1403. A similar trend was observed for chaining MG1363ΔacmA when it is compared to its control MG1363. The clumping strain MG1614_clu+ increased gel hardness by 4.3% compared to its control MG1614, however, changes in gel hardness below 10% are thought to not be perceived in the mouth. As an increase in gel hardness is not seen for all strains where the pili were overexpressed we conclude that the effect is strain dependent which can be explained by different surface properties of the strains used. Together these results show that bacteria with pili on its surface can significantly enhance the milk gel strength.

TABLE 7

Gel hardness (g) and viscosity (mPa · s) of milk fermented by surface altered *lactococci*. The results show the average of 3 biological replications.

| Strain | Gel hardness (g) | pH | Viscosity, mPa · s |
|---|---|---|---|
| Pili overexpressing strains compare to their control strains without pili | | | |
| MG1363(pIL253) | 40.1 ± 2.18 | 4.29 ± 0.05 | 722.7 ± 11.3 |
| MG1363(pIL253pilΔ1) | 45.1 ± 1.13* | 4.23 ± 0 | 1050 ± 19.1* |
| MG1363(pIL253pil) | 47.8 ± 1.8* | 4.23 ± 0.05 | 1079.3 ± 58.2* |
| MG1363pNZ521 | 42.8 ± 0.4 | 4.22 ± 0.05 | 773 ± 64.3 |
| MG1363pNZ521 (pIL253pil) | 49.1 ± 2.8* | 4.34 ± 0.006 | 1027.2 ± 30* |
| NCDO712 | 43.5 ± 0.6 | 4.24 ± 0.06 | 1498 ± 60.6 |
| NCDO712(pIL253pil) | 42.4 ± 3.2 | 4.23 ± 0.006 | 1192 ± 146.2* |
| MG1299 | 38.59 ± 0.6 | 4.23 ± 0.05 | 726.1 ± 68.1 |
| MG1299(pIL253pil) | 38.2 ± 0.6 | 4.27 ± 0.001 | 797 ± 54 |
| IL1403 | 37.5 ± 0.64 | 4.45 ± 0.02 | 680.1 ± 34.5 |
| IL1403(pIL253pil) | 37 ± 0.7 | 4.47 ± 0.001 | 745 ± 78 |
| Combinations of EPS and pili/no-pili forming strains | | | |
| MG1363pNZ4120 | 48.9 ± 1.9 | 4.32 ± 0.006 | 4556 ± 37.7* |
| MG1363pNZ4120 + MG1363(pIL253pil) | 51.9 ± 1.1 | 4.22 ± 0.006 | 3231 ± 78.9 |
| MG1363pNZ4120 + MG1363(pIL253pilΔ) | 44.4 ± 3.6 | 4.19 ± 0.006 | 2921 ± 277.7 |
| MG1363pNZ4120 + MG1363pIL253 | 46.9 ± 2.9 | 4.24 ± 0.006 | 3242.7 ± 396.7 |
| MG1363pNZ4120 + NCDO712 | 45.6 ± 6.8 | 4.18 ± 0.01 | 2847 ± 117.1 |
| MG1363pNZ4120 + NCDO712(pIL253pil) | 46.97 ± 1.48 | 4.21 ± 0 | 2976 ± 105.5 |
| Chaining strains | | | |
| IL1403 | 37.5 ± 0.64 | 4.45 ± 0.02 | 680.1 ± 34.5 |
| IL1403ΔacmAacmD | 35.4 ± 0.14* | 4.39 ± 0.01 | 1008.5 ± 109.3* |
| MG1363 | 47.2 ± 2.08 | 4.24 ± 0.06 | 926.1 ± 50.5 |
| MG1363ΔacmA | 41.5 ± 1.08* | 4.24 ± 0.05 | 1034.7 ± 18.9* |
| Transconjugants (clumping/non-clumping) | | | |
| MG1614 | 40 ± 0.43 | 4.23 ± 0.05 | 832.5 ± 40.9 |
| MG1614_clu− | 39 ± 1.19 | 4.27 ± 0.06 | 739 ± 37* |
| MG1614_clu+ | 41.7 ± 1 | 4.27 ± 0.05 | 887.9 ± 28 |
| NCDO712 derivatives carrying 1 or 2 plasmids; MG1363 derivatives with deletion of 1 gene | | | |
| NCDO712 | 42.4 ± 1.3 | 4.24 ± 0.06 | 867.2 ± 106.1 |
| MG1363 | 43.78 ± 0.89 | 4.24 ± 0.05 | 926.1 ± 50.5 |
| MG1363ΔahrG | 43.8 ± 0.43 | 4.28 ± 0.03 | 771 ± 205.5 |
| MG1363ΔdltD | 43.9 ± 0.56 | 4.24 ± 0.05 | 891.9 ± 66.9 |
| MG1363ΔgalE | 44.71 ± 0.58 | 4.21 ± 0.05 | 871.1 ± 181.3 |
| MG1063 | 45.17 ± 0.39 | 4.19 ± 0.05 | 986.97 ± 20.7 |
| MG1261 | 41 ± 0.91 | 4.21 ± 0.05 | 790.97 ± 20.6 |
| MG1362 | 44.1 ± 0.81 | 4.2 ± 0.04 | 945.1 ± 40.9 |
| MG1299 | 38.59 ± 0.6 | 4.23 ± 0.05 | 726.1 ± 68.1 |

*Significant at p < 0.05-comparisons were made to non-surface modified controls with the same gray-color code in the rows above.

Viscosity was increased by 19-35% in milk fermented with MG1363(pIL253pil) (p=0.0005) and MG1363pNZ521 (pIL253pil) (p=0.003) compared to the control conditions fermented with MG1363pIL253 and MG1363pNZ521, respectively (Table 7). An increased viscosity, however not significant, was observed for pili overexpressing strains such as lactose/protease positive strain MG1299(pIL253pil) (p=0.23) and for *L. lactis* IL1403(pIL253pil) (p=0.26). In comparison to milk fermented with the EPS producing strain MG1363pNZ4120 the increase in viscosity caused by pili production is lower. There was no synergy effects found when milk was fermented with a 1:1 mixture of EPS and pili producing strains. However it is likely that that an up to 35% increase in viscosity caused by pili expression is a substantial alteration of food texture. When cells produced a high number of pili they also showed increased chaining. These strains formed milk gels with increased viscosity. For example, the chaining strain MG1363ΔacmA and IL1403ΔacmΔacmD formed milk gel with a viscosity which increased by 11% and by approximately 50% compared to their controls MG1363 (p=0.025) and IL1403 (p=0.026) shown in Table 7. Acidification rate can be excluded as influencing factor on milk viscosity for it is similar for the compared samples. The results of milk viscosity show that surface properties such as cell aggregation, chaining, formation of EPS and pili, increase product thickness in the range of 20-48%.

Correlation between surface properties and textural parameters of fermented milk product.

No correlation was seen between cell surface charge, surface hydrophobicity, attachment to proteins, and emulsion stability, these are all independent parameters. However, the surface morphology such as clumping, expression of pili, and EPS formation influence the charge, hydrophobicity and attachment to proteins. For example, by making correlations for only pili-overexpressed stains and its control strains we saw that the presence of pili on bacterial surface led to increased surface hydrophobicity and, consequently, emulsion stability (r=0.91), while in general emulsion stability and hydrophobicity are independent parameters. Furthermore, clumping, over-expression of pili and EPS formation influence the gel hardness and viscosity (r>0.82).

Importantly, no correlation was seen between pH and viscosity (r=−0.07) and between pH and gel hardness (r=−0.59). Thus, chaining, clumping, formation of pili or EPS influence both the cells surface properties and textural parameters of a product.

Discussion.

Here we investigated the potential role of bacterial surface properties and morphologies on the production of volatile metabolites, the structure, and the textural parameters of fermented milk. The surface properties of lactococci were modified in terms of chaining, clumping, exopolysaccharide formation, and pili over-expression. All surface alterations were in an isogenic background to be able to compare the results. Furthermore, the milk composition, milk pre-treatment and fermentation conditions were the same to eliminate the influence of these factors on the results. The acidification rate of used strains was also measured to be sure that the acidification speed between strain of interest and its control strains are similar. Additionally, pH of fermented milk did not correlate with milk viscosity and gel hardness. Therefore, all these mentioned parameters can be excluded as influencing factors on structure, texture, and volatiles' formation of fermented milk. The results not only demonstrate that alteration of cell surface properties (chaining, clumping, formation of exopolysaccharides, pili over-expression) affect cell surface charge, hydrophobicity and the attachment to proteins, but also textural parameters of fermented milk, including viscosity, gel hardness and the bacterial localization in the food matrix (Table 8). Based on the observed effects of cell surface composition on textural parameters of fermented milk, we hypothesize that bacteria could be considered as structure element in a food matrix.

TABLE 8

The summary of textural parameters of milk gel fermented with surface altered *lactococci*.

| Phenotype | Strain | Viscosity | Gel hardness |
|---|---|---|---|
| Pili over-expression | MG1363(pIL253pil) | ↑* | ↑* |
|  | MG1363(pIL253pilΔ1) | ↑* | ↑* |
|  | MG1363pNZ521(pIL253pil) | ↑* | ↑* |
|  | MG1299(pIL253pil) | ↑ | ↑ |
|  | NCDO712(pIL253pil) | ≈ | ↓* |
|  | IL1403(pIL253pil) | ↑ | ≈ |
| Chaining | IL1403ΔacmAacmD | ↑* | ↓* |
|  | MG1363ΔacmA | ↑* | ↓* |
| Clumping | Transconjugant 5 | ↑ | ↑* |

↑ increased; ≈ did not change; ↓ decreased; * significance (p < 0.05)

As structure element bacterial cells possess amphiphilic surface properties, so the cells are charged and at the same time have hydrophobic areas which are determined by the complex molecular composition of cell wall. For example, the pili-overexpression in the strain MG1363pIL253 led in neutral pH to decreased charge from −26.4±1.8 mV to −11.87±0.21 mV, and increased hydrophobicity from 5% to 96%. The charge decrease can be explained by the positive net-charge of pilin proteins. Additionally, the charged residues of the pilin protein should be reflected on the outside of the pilus because charged residues in the core of a tight 3D structure are generally unfavorable; and most positive charge is from arginine which is quite bulky and double occurrences of a few positively charged amino acids would hinder protein folding even further (66). However, the surface of lactococcal bacteria is much more complex; therefore, the overall net surface charge of pili expressing strains remains negative. As well as having positively and negatively charged regions, pili have 30-40% hydrophobic patches (based on protein sequence analysis) which would be buried in the protein molecule or they will be involved in the inter-protein connections during pili organization. Possibly these pili hydrophobic patches are responsible for the increase in the cell surface hydrophobicity from 5-20% to 99%.

Figure 9:
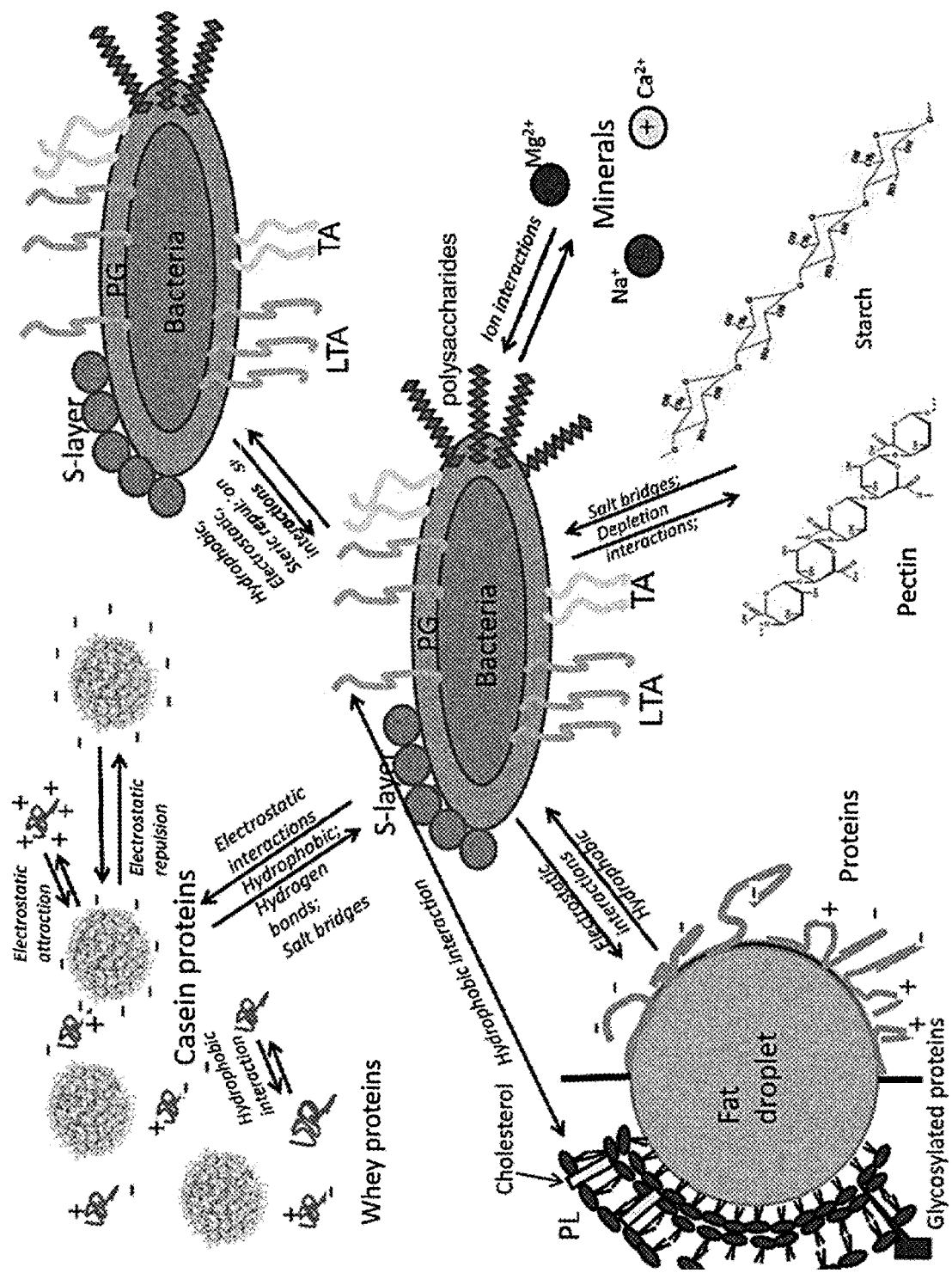

Bacterial surfaces engage in physico-chemical interactions with milk components. The cell surface composition is the polymeric layer. There are various interactions that can occur between the molecules of the polymeric layer of bacteria and milk components or between cell surfaces of two bacteria: Van der Waals interactions (29), electrostatic repulsions and attractions, hydrogen bonds, hydrophobic interactions, salt bridges and steric interactions (6, 60) (FIG. 9). The combination of all of these interactions at the same time is also possible. The structure, stability and textural properties of fermented milk matrix are determined by the type of microbe-matrix interaction and interaction force. The type of microbe-matrix interactions depend not only on the pH, the bacterial localization in milk before fermentation, the nutrient distribution in milk matrix, the roughness of the cell surface but also on the strain itself. Importantly, for most lactococcal cells, pH does not influence the cell surface charge, it constantly remains negative. Modifying the cell surface morphology, changes are seen surface properties, and consequently microbe-matrix interactions. The end result of this all is that the structure and textural parameters of milk significantly change.

Possessing amphiphilic properties and having complex surface molecular composition, as a structural element bacteria can have several roles in a fermented milk: 1) interact with proteins and other milk components or not, 2) can locate in serum regions or in protein matrix, and 3) form clumps or not. Based on these three items, the impact of bacteria on textural milk properties can be found. Considering the first item, bacterial surfaces engage in physico-chemical interactions with milk components. The cell surface composition we can call polymeric layer. Between the molecules of the polymeric layer of bacteria and milk proteins or between cell surfaces of two bacteria combination of several interactions can occur at the same time: Van der Waals interactions (26), electrostatic repulsions and attractions, hydrogen bonds, hydrophobic interactions, salt bridges, and steric interactions (5, 57). For instance, for LGG the force between micellar casein (or denatured whey) protein and cell is about 0.4 nN (6), and it is very strain-dependent. The type of microbe-matrix interaction and force strength between microbe-matrix seem to determine the structure, stability, and textural properties of fermented milk matrix. The type of microbe-matrix interactions depend on the pH, the bacterial localization in milk before fermentation, the nutrient distribution in milk matrix, the roughness of the cell surface and the strain itself. Importantly, for most lactococcal cells, the pH does not influence the cell surface charge, it constantly remains negative. We saw that by modifying the cell surface morphology, we change surface properties, and consequently microbe-matrix interactions. As a result, the structure and textural parameters of milk significantly change. In milk (pH 6.7) electrostatic repulsion occurs between negatively charged casein molecules and between milk proteins and negatively charged bacterial cells through presence of acid/base groups on their surfaces (e.g. in proteins). Electrostatic interactions depend on the pH and ion concentration in milk. At the same time the cell surface contains also hydrophobic patches (surface proteins, pili) which interact with hydrophobic patches of milk proteins or other bacterial surface molecules (pili or other surface proteins). Hydrophobic interactions are the strongest and its strength increases when the temperature increases (59). During milk fermentation the pH drops from 6.7 to 4.2 via coagulation point 4.6 of caseins (25). Protein aggregation starts already at pH 5.2-5.3, and at pH 4.6 casein micelles aggregate, because the negative charge of caseins is shielded by $H^+$ of lactic acid produced by the bacteria. Subsequently, hydrophobic patches of casein molecules unfold and milk proteins start to aggregate via hydrophobic interactions. At this point bacterial cells which do not interact with milk components become incorporated in the milk gel network. When the pH decreases below coagulation pH 4.6 of casein micelles, milk proteins become positively charged. In this case the bacterial attachment to milk proteins is governed by a combination of interactions including electrostatic and hydrophobic forces.

The second and third mentioned roles of bacteria were cell location in serum regions or in protein matrix and formation of chains/clumps which increases fermented milk viscosity and gel hardness. The microscopic observations of the cell localization of pili over-expressing cells in the milk matrix seem to show a more dense milk gel structure. These cells seem to be localized in the serum regions (FIG. 7 and FIG. 8, panel B). Pili over-expression increased the viscosity of fermented milk up to 35% (Table 7). This was seen independently for three pili over-expressing strains: MG1363(pIL253pil), MG1363pNZ521(pIL253pil), MG1299(pIL253pil), but not for NCDO712(pIL253pil) and IL1403(pIL253pil), which indicates that this effect might be background dependent. NCDO712 already harbors the pilin genes which make differences upon increasing the expression less pronounced. For IL1403 electron microscopy showed relatively few pili on the surface which might explain our findings. Importantly, a 20% increase in viscosity is likely to be perceived in a mouth and it would be interesting to test this in a sensory analysis. Increased viscosity might be explained by the increased solid content of proteins aggregates with cell aggregates in the milk serum phase. Here the size and shape of particles is of importance: cells form very strong aggregates and locate in serum cavities which mean the amount of free water is decreased.

As it was mentioned above, chaining bacteria (acmA/acmD deletions) increased viscosity up to 12-48%, but decrease gel hardness by 6-14% (Table 7, FIG. 8, panel C). The decreased gel hardness might be explained by cavities of serum in milk matrix: they do not provide any additional bonds to make gel stronger, and also possibly that the cells, which do not interact with the aggregated caseine micelles, are thus not included in the matrix but end up more like structure breakers, it means the matrix has to form around them. The increased viscosity of milk matrix fermented with chaining cells might be explained by cell morphology, cell size e.g. length is of importance here. No changes in volatile formation were detected for chaining strains compared to non-chaining controls. It could be explained by unchanged cell surface hydrophobicity leading to inability to bind more volatile molecules or simply because chaining does not affect the formation of any volatiles.

Such cell localization in the cavities of protein matrix, cell surface roughness, less cavities in the protein matrix, cell chaining, strong forces between cell-cell connections, attraction forces between cells-proteins, all these parameters seem to provide high viscosity and gel strength to milk matrix. Overall our findings suggest that by altering surface properties of dairy starter cultures it is possible to change product properties such as gel hardness and milk viscosity without changing the volatile profile. It will be highly interesting to see if the indicated properties can be perceived in sensory analysis. This would open possibilities to develop new concepts to improve fermented products.

Example 3. Bacteria as Structural Elements in a Fermented Food Product; Cell Distribution in Whey and Curd A functional property investigated in cheese manufacturing was if alterations on the cell surface of a dairy bacterial strain according to the invention changes the fraction of cells that remain in curd during cheese making. The results are listed in Table 9 here below. In contrast to earlier believes that in general roughly 90% of the cells remains in the curd and 10% is in the whey, the data showed variations from ~50% to ~80% of cells remaining in the curd with a bacterial cell that is not a bacterial cell according to the invention. Introduction of the empty vector pIL253 into strain MG1363 increased the fraction of cells in the curd from ~50% to ~86%. This is intriguing as the empty vector harbours only replication genes and an antibiotic marker. However, we did see with electron microscopy that the introduction of the empty pIL253 plasmid leads to an altered cell morphology. When overexpressing the pilin operon from pIL253 the fraction of cells remaining in curd increases further to ~98%. In cheese produced with an EPS producing strain only (MG1363pNZ4120) ~50% of cells remained in the curd while the combination of this strains with pili producing strains during manufacturing increased the cell fraction in curd to 99%. Together this indicates significant effects of surface properties/decoration on the cell distribution in curd and whey during cheese making using a dairy bacterial strain according to the invention.

TABLE 9

Cell distribution in whey and curd (%) after cell surface alterations.

| STRAIN | CFU/ml whey | | CFU/g curd | | Fraction in curd (%) | |
| --- | --- | --- | --- | --- | --- | --- |
| | MEAN | SD | MEAN | SD | MEAN | SD |
| Pili overexpression | | | | | | |
| MG1299 | 4.13E+07 | 2.33E+07 | 3.74E+08 | 3.19E+08 | 79.30 | 16.62 |
| MG1299pil | 7.05E+05 | 1.19E+05 | 4.02E+08 | 2.46E+07 | 99.82 | 0.04 |
| IL1403 | 4.23E+06 | 3.46E+06 | 1.03E+07 | 6.66E+06 | 65.43 | 31.23 |
| IL1403pil | 2.72E+05 | 1.17E+04 | 5.98E+07 | 9.28E+06 | 99.54 | 0.09 |
| MG1363 | 1.54E+07 | 1.28E+07 | 1.42E+07 | 1.13E+07 | 49.73 | 8.24 |
| MG1363pIL253 | 4.69E+06 | 2.98E+06 | 3.06E+07 | 1.56E+07 | 86.75 | 4.19 |

TABLE 9-continued

Cell distribution in whey and curd (%) after cell surface alterations.

| STRAIN | CFU/ml whey | | CFU/g curd | | Fraction in curd (%) | |
|---|---|---|---|---|---|---|
| | MEAN | SD | MEAN | SD | MEAN | SD |
| MG1363pil_28 | 1.76E+06 | 1.43E+06 | 8.08E+07 | 7.29E+07 | 97.41 | 0.82 |
| MG1363pil_17 | 6.62E+05 | 3.48E+05 | 1.73E+07 | 1.18E+07 | 95.71 | 1.25 |
| Mixture of EPS and pili producing strains | | | | | | |
| MG1363pNZ4120 | 5.62E+06 | 1.18E+06 | 6.77E+06 | 1.99E+06 | 54.13 | 5.17 |
| MG1363pil + MG1363eps | 5.23E+05 | 3.73E+05 | 4.48E+07 | 3.45E+07 | 98.75 | 0.29 |

REFERENCE LIST

1. Abbasnezhad, H., J. M. Foght, and M. R. Gray. 2011. Adhesion to the hydrocarbon phase increases phenanthrene degradation by *Pseudomonas fluorescens* LP6a. Biodegradation 22:485-96.
2. Amatayakul, T., a. L. Halmos, F. Sherkat, and N. P. Shah. 2006. Physical characteristics of yoghurts made using exopolysaccharide-producing starter cultures and varying casein to whey protein ratios. Int. Dairy J. 16:40-51.
3. Boels, I. C., R. Van Kranenburg, W. Marja, B. F. Chong, W. M. De Vos, M. W. Kanning, and M. Kleerebezem. 2003. Increased Exopolysaccharide Production in *Lactococcus lactis* due to Increased Levels of Expression of the NIZO B40 eps Gene Cluster Increased Exopolysaccharide Production in *Lactococcus lactis* due to Increased Levels of Expression of the NIZO B40 eps Gene 69:8-11.
4. Bolotin, A., P. Wincker, and S. Mauger. 2001. The complete genome sequence of the lactic acid bacterium *Lactococcus lactis* ssp. *lactis* IL1403. Genome Reseach 731-753.
5. Bosshard, H. R., D. N. Marti, and I. Jelesarov. 2004. Protein stabilization by salt bridges: Concepts, experimental approaches and clarification of some misunderstandings. J. Mol. Recognit. 17:1-16.
6. Burgain, J., C. Gaiani, G. Francius, a M. Revol-Junelles, C. Cailliez-Grimal, S. Lebeer, H. L. P. Tytgat, J. Vanderleyden, and J. Scher. 2013. In vitro interactions between probiotic bacteria and milk proteins probed by atomic force microscopy. Colloids Surf. B. Biointerfaces. Elsevier B. V. 104:153-62.
7. Burgain, J., J. Scher, G. Francius, F. Borges, M. Corgneau, a. M. Revol-Junelles, C. Cailliez-Grimal, and C. Gaiani. 2014. Lactic acid bacteria in dairy food: Surface characterization and interactions with food matrix components. Adv. Colloid Interface Sci. Elsevier B. V. 213:21-35.
8. Burgain, J., J. Scher, S. Lebeer, J. Vanderleyden, C. Cailliez-Grimal, M. Corgneau, G. Francius, and C. Gaiani. 2014. Significance of bacterial surface molecules interactions with milk proteins to enhance microencapsulation of *Lactobacillus rhamnosus* GG. Food Hydrocoll. Elsevier Ltd 41:60-70.
9. Burgain, J., J. Scher, S. Lebeer, J. Vanderleyden, M. Corgneau, J. Guerin, C. Caillet, J. F. L. Duval, G. Francius, and C. Gaiani. 2015. Impacts of pH-mediated EPS structure on probiotic bacterial pili-whey proteins interactions. Colloids Surfaces B Biointerfaces. Elsevier B. V. 134:332-338.
10. Busscher, H., and A. Weerkamp. 1987. Specific and non-specific interactions in bacterial adhesion to solid substrata. FEMS Microbiol. Lett. 46:165-173.
11. Cheng, J., Y. Ma, X. Li, T. Yan, and J. Cui. 2015. Effects of milk protein-polysaccharide interactions on the stability of ice cream mix model systems. Food Hydrocoll. Elsevier Ltd 45:327-336.
12. Costa, N. E., D. J. O'Callaghan, M. J. Mateo, V. Chaurin, M. Castillo, J. a. Hannon, P. L. H. McSweeney, and T. P. Beresford. 2012. Influence of an exopolysaccharide produced by a starter on milk coagulation and curd syneresis. Int. Dairy J. Elsevier Ltd 22:48-57.
13. Delcour, J., T. Ferain, M. Deghorain, E. Palumbo, and P. Hols. 1999. The biosynthesis and functionality of the cell-wall of lactic acid bacteria. Antonie Van Leeuwenhoek 76:159-84.
14. Dickinson, E. 2015. Microgels—An alternative colloidal ingredient for stabilization of food emulsions. Trends Food Sci. Technol. Elsevier Ltd 43:178-188.
15. Duwat, P., A. Cochu, S. D. Ehrlich, and A. Gruss. 1997. Characterization of *Lactococcus lactis* UV-sensitive mutants obtained by ISS1 transposition. Characterization of *Lactococcus lactis* UV-Sensitive Mutants Obtained by ISS1 Transposition. Microbiology 179:4473-4479.
16. Evans, M., I. Ratcliffe, and P. a. Williams. 2013. Emulsion stabilisation using polysaccharide-protein complexes. Curr. Opin. Colloid Interface Sci. Elsevier Ltd 18:272-282.
17. Folkenberg, D. M., P. Dejmek, A. Shiver, H. Skov Guldager, and R. Ipsen. 2006. Sensory and rheological screening of exopolysaccharide producing strains of bacterial yoghurt cultures. Int. Dairy J. 16:111-118.
18. Gallardo-Escamilla, F. J., a. L. Kelly, and C. M. Delahunty. 2005. Influence of Starter Culture on Flavor and Headspace Volatile Profiles of Fermented Whey and Whey Produced from Fermented Milk. J. Dairy Sci. Elsevier 88:3745-3753.
19. Gasson, M. J. 1983. Plasmid complements of *Streptococcus lactis* NCDO 712 and other lactic streptococci after protoplast-induced curing. J. Bacteriol. 154:1-9.
20. Gasson, M. J., and F. L. Davies. 1980. High-frequency conjugation associated with *Streptococcus lactis* donor cell aggregation. J. Bacteriol. 143:1260-1264.
21. Gastaldi, E., a Lagaude, S. Marchesseau, B. T. D. E. L. a Fuente, and B. T. DelaFuente. 1997. Acid Milk Gel Formation as Affected by Total Solids Content. J. Food Sci. 62:671-676.
22. Giaouris, E., M.-P. Chapot-Chartier, and R. Briandet. 2009. Surface physicochemical analysis of natural *Lactococcus lactis* strains reveals the existence of hydrophobic and low charged strains with altered adhesive properties. Int. J. Food Microbiol. Elsevier B. V. 131:2-9.
23. Grossiord, P., E. J. Luesink, E. E. Vaughan, A. Arnaud, W. M. De Vos, B. P. Grossiord, E. J. Luesink, E. E.

Vaughan, A. Arnaud, and W. M. De Vos. 2003. Characterization, Expression, and Mutation of the *Lactococcus lactis* galPMKTE Genes, Involved in Galactose Utilization via the Leloir Pathway. Society 185:870-878.

24. Hadde, E. K., T. M. Nicholson, J. a. Y. Cichero, and C. Deblauwe. 2015. Rheological characterisation of thickened milk components (protein, lactose and minerals). J. Food Eng. Elsevier Ltd 166:263-267.

25. Hamet, M. F., J. a. Piermaria, and A. G. Abraham. 2015. Selection of EPS-producing *Lactobacillus* strains isolated from kefir grains and rheological characterization of the fermented milks. LWT—Food Sci. Technol. Elsevier Ltd 63:129-135.

26. Hassan, A. N., R. Ipsen, T. Janzen, and K. B. Qvist. 2003. Microstructure and Rheology of Yogurt Made with Cultures Differing Only in Their Ability to Produce Exopolysaccharides. J. Dairy Sci. 86:1632-1638.

27. Hassan, A. N., J. F. Frank, and K. B. Qvist. 2002. Direct observation of bacterial exopolysaccharides in dairy products using confocal scanning laser microscopy. J. Dairy Sci. Elsevier 85:1705-8.

28. Holt, C., J. a. Carver, H. Ecroyd, and D. C. Thorn. 2013. Invited review: Caseins and the casein micelle: Their biological functions, structures, and behavior in foods. J. Dairy Sci. Elsevier 96:6127-6146.

29. Jacobs, a., F. Lafolie, J. M. Herry, and M. Debroux. 2007. Kinetic adhesion of bacterial cells to sand: Cell surface properties and adhesion rate. Colloids Surfaces B Biointerfaces 59:35-45.

30. Jarunglumlert, T., K. Nakagawa, and S. Adachi. 2015. Influence of aggregate structure of casein on the encapsulation efficiency of (3-carotene entrapped via hydrophobic interaction. Food Struct. Elsevier Ltd. 5:42-50.

31. Joyner (Melito), H. S., and H. Damiano. 2015. Influence of various hydrocolloids on cottage cheese cream dressing stability. Int. Dairy J. Elsevier Ltd 51:24-33.

32. Larsen, R., G. Buist, O. P. Kuipers, and J. Kok. 2004. ArgR and AhrC Are Both Required for Regulation of Arginine Metabolism in *Lactococcus lactis*. J. Bacteriol. 186:1147-1157.

33. Lee, W. J., and J. a. Lucey. 2010. Formation and physical properties of yogurt. Asian-Australasian J. Anim Sci. 23:1127-1136.

34. Leroy, F., and L. De Vuyst. 2004. Lactic acid bacteria as functional starter cultures for the food fermentation industry. Trends Food Sci. Technol. 15:67-78.

35. Li, J.-M., and S.-P. Nie. 2015. The functional and nutritional aspects of hydrocolloids in foods. Food Hydrocoll. Elsevier Ltd.

36. Lucey, J. a., and H. Singh. 1997. Formation and physical properties of acid milk gels: A review. Food Res. Int. 30:529-542.

37. Lucey, J. a., C. T. Teo, P. a. Munro, and H. Singh. 1997. Rheological properties at small (dynamic) and large (yield) deformations of acid gels made from heated milk. J. Dairy Res. 64:591-600.

38. Lucey, J. a. 2004. Cultured dairy products: an overview of their gelation and texture properties. Int. J. Dairy Technol. 57:77-84.

39. Lucey, J. a. 2001. The relationship between rheological parameters and whey separation in milk gels. Food Hydrocoll. 15:603-608.

40. Ly, M. H., M. Aguedo, S. Goudot, M. L. Le, P. Cayot, J. a. Teixeira, T. M. Le, J.-M. Belin, and Y. Waché. 2008. Interactions between bacterial surfaces and milk proteins, impact on food emulsions stability. Food Hydrocoll. 22:742-751.

41. Ly-Chatain, M. H., M. Linh, M. L. Le, J. Belin, Y. Wache, M. Le Thanh, J. Belin, and Y. Wache. 2010. Cell surface properties affect colonisation of raw milk by lactic acid bacteria at the microstructure level. Food Res. Int. Elsevier Ltd 43:1594-1602.

42. Macciola, V., G. Candela, and a. De Leonardis. 2008. Rapid gas-chromatographic method for the determination of diacetyl in milk, fermented milk and butter. Food Control 19:873-878.

43. Mao, Y., and D. J. McClements. 2013. Modulation of food texture using controlled heteroaggregation of lipid droplets: Principles and applications. J. Appl. Polym. Sci. n/a-n/a.

44. Meijer, W. C., and J. Hugenholtz. 1997. Proteolytic enzyme activity in lactococci grown in different pretreated milk media. J. Appl. Microbiol. 83:139-46.

45. Meyrand, M., A. Guillot, M. Goin, S. Furlan, J. Armalyte, S. Kulakauskas, N. G. Cortes-Perez, G. Thomas, S. Chat, C. Péchoux, V. Dupres, P. Hols, Y. F. Dufrêne, G. Trugnan, and M.-P. Chapot-Chartier. 2013. Surface proteome analysis of a natural isolate of *Lactococcus lactis* reveals the presence of pili able to bind human intestinal epithelial cells. Mol. Cell. Proteomics 12:3935-47.

46. Morell, P., S. M. Fiszman, P. Varela, and I. Hernando. 2014. Hydrocolloids for enhancing satiety: Relating oral digestion to rheology, structure and sensory perception. Food Hydrocoll. Elsevier Ltd 41:343-353.

47. Ploux, L., A. Ponche, and K. Anselme. 2010. Bacteria/Material Interfaces: Role of the Material and Cell Wall Properties. J. Adhes. Sci. Technol. 24:2165-2201.

48. Prasanna, P. H. P., a. S. Grandison, and D. Charalampopoulos. 2013. Microbiological, chemical and rheological properties of low fat set yoghurt produced with exopolysaccharide (EPS) producing *Bifidobacterium* strains. Food Res. Int. Elsevier Ltd 51:15-22.

49. Simon, D., and A. Chopin. 1988. Construction of a vector plasnfid family and its use for molecular cloning in *Streptococcus lactis* 70:559-566.

50. Smid, E. J., and M. Kleerebezem. 2014. Production of Aroma Compounds in Lactic Fermentations. Annu. Rev. Food Sci. Technol. 5:313-326.

51. Smit, B. a, W. J. M. Engels, M. Alewijn, G. T. C. a Lommerse, E. a H. Kippersluijs, J. T. M. Wouters, and G. Smit. 2004. Chemical conversion of alpha-keto acids in relation to flavor formation in fermented foods. J. Agric. Food Chem. 52:1263-8.

52. Smit, B. A., J. E. T. van Hylckama Vlieg, W. J. M. Engels, L. Meijer, J. T. M. Wouters, and G. Smit. 2005. Identification, cloning, and characterization of a *Lactococcus lactis* branched-chain alpha-keto acid decarboxylase involved in flavor formation. Appl. Environ. Microbiol. 71:303-11.

53. Smit, G., B. a Smit, and W. J. M. Engels. 2005. Flavour formation by lactic acid bacteria and biochemical flavour profiling of cheese products. FEMS Microbiol. Rev. 29:591-610.

54. Sodini, I., F. Remeuf, S. Haddad, and G. Corrieu. 2004. The relative effect of milk base, starter, and process on yogurt texture: a review. Crit. Rev. Food Sci. Nutr. 44:113-37.

55. Steen, A., G. Buist, G. J. Horsburgh, G. Venema, 0. P. Kuipers, S. J. Foster, and J. Kok. 2005. AcmA of *Lacto-*

55. *coccus lactis* is an N-acetylglucosaminidase with an optimal number of LysM domains for proper functioning. FEBS J. 272:2854-2868.
56. Steen, A., E. Palumbo, M. Deghorain, S. Cocconcelli, J. Delcour, O. P. Kuipers, G. Buist, P. Hols, P. S. Cocconcelli, and J. Kok. 2005. Autolysis of *Lactococcus lactis* Is Increased upon d-Alanine Depletion of Peptidoglycan and Lipoteichoic Acids Autolysis of *Lactococcus lactis* Is Increased upon D—Alanine Depletion of Peptidoglycan and Lipoteichoic Acids. J. Bacteriol. 187:114-124.
57. Stiles, M. E., and W. H. Holzapfel. 1997. Lactic acid bacteria of foods and their current taxonomy. Int. J. Food Microbiol. 36:1-29.
58. Tuinier, R., W. H. van Casteren, P. J. Looijesteijn, H. a Schols, a G. Voragen, and P. Zoon. 2001. Effects of structural modifications on some physical characteristics of exopolysaccharides from *Lactococcus lactis*. Biopolymers 59:160-6.
59. Tuinier, R., T.-H. Fan, and T. Taniguchi. 2015. Depletion and the dynamics in colloid-polymer mixtures. Curr. Opin. Colloid Interface Sci. Elsevier Ltd 20:66-70.
60. Ubbink, J., and P. Schar-Zammaretti. 2005. Probing bacterial interactions: integrated approaches combining atomic force microscopy, electron microscopy and biophysical techniques. Micron 36:293-320.
61. Van de Bunt, B., P. a Bron, L. Sijtsma, W. M. de Vos, and J. Hugenholtz. 2014. Use of non-growing *Lactococcus lactis* cell suspensions for production of volatile metabolites with direct relevance for flavour formation during dairy fermentations. Microb. Cell Fact. 13:176.
62. Van Oss, C. J. 2003. Long-range and short-range mechanisms of hydrophobic attraction and hydrophilic repulsion in specific and aspecific interactions. J. Mol. Recognit. 16:177-190.
63. Visweswaran, G. R. R., A. Steen, K. Leenhouts, M. Szeliga, B. Ruban, A. Hesseling-Meinders, B. W. Dijkstra, O. P. Kuipers, J. Kok, and G. Buist. 2013. AcmD, a Homolog of the Major Autolysin AcmA of *Lactococcus lactis*, Binds to the Cell Wall and Contributes to Cell Separation and Autolysis. PLoS One 8:1-11.
64. Wang, L., Y. Cao, K. Zhang, Y. Fang, K. Nishinari, and G. O. Phillips. 2015. Hydrogen bonding enhances the electrostatic complex coacervation between κ-carrageenan and gelatin. Colloids Surfaces A Physicochem. Eng. Asp. Elsevier B. V. 482:604-610.
65. Wegmann, U., K. Overweg, S. Jeanson, M. Gasson, and C. Shearman. 2012. Molecular characterization and structural instability of the industrially important composite metabolic plasmid pLP712. Microbiology 158:2936-45.
66. Tsumoto, K., M. Umetsu, I. Kumagai, D. Ejima, J. S. Philo, and T. Arakawa. 2004. Role of Arginine in Protein Refolding, Solubilization, and Purification. Biotechnol. Frog. 20:1301-1308.
67. Ainsworth, S., J. Mahony, and D. van Sinderen. 2014. The plasmid complement of *Lactococcus lactis* UC509.9 encodes multiple bacteriophage resistance systems. Appl. Environ. Microbiol. 80:4341-9.
68. Ainsworth, S., S. Stockdale, F. Bottacini, J. Mahony, and D. van Sinderen. 2014. The *Lactococcus lactis* plasmidome: much learnt, yet still lots to discover. FEMS Microbiol. Rev. 38:1066-88.
69. Ajunwa, O. M., O. A. Odeniyi, A. J. Adeleke, K. E. Nwanekwu, and C. E. Obiukwu. 2014. VARIATION IN THE PRESENCE OF PLASMIDS ASSOCIATED WITH PROTEINASE AND BACTERIOCIN PRODUCTION OF *LACTOCOCCUS LACTIS* ISOLATED FROM NATURALLY FERMENTED MILK 21:381-388.
70. AKELIK, M. 2001. Identification of a Lactose Utilization and Copper Resistance Plasmid in *Lactococcus lactis* subsp. *lactis* MCL64. Turkish J. Vet. Anim 25:783-787.
71. Anderson, D. G., and L. L. McKay. 1984. Genetic and physical characterization of recombinant plasmids associated with cell aggregation and high-frequency conjugal transfer in *Streptococcus lactis* ML3. J. Bacteriol. 158:954-62.
72. Aziz, R. K., D. Bartels, A. a Best, M. DeJongh, T. Disz, R. a Edwards, K. Formsma, S. Gerdes, E. M. Glass, M. Kubal, F. Meyer, G. J. Olsen, R. Olson, A. L. Osterman, R. a Overbeek, L. K. McNeil, D. Paarmann, T. Paczian, B. Parrello, G. D. Pusch, C. Reich, R. Stevens, O. Vassieva, V. Vonstein, A. Wilke, and O. Zagnitko. 2008. The RAST Server: rapid annotations using subsystems technology. BMC Genomics 9:75.
73. Barrick, J. E., G. Colburn, D. E. Deatherage, C. C. Traverse, M. D. Strand, J. J. Borges, D. B. Knoester, A. Reba, and A. G. Meyer. 2014. Identifying structural variation in haploid microbial genomes from short-read resequencing data using breseq. BMC Genomics 15:1039.
74. Belkum, M. J. V. A. N., B. J. A. N. Hayema, R. E. Jeeninga, J. A. N. Kok, and G. Venema. 1991. Organization and Nucleotide Sequences of Two Lactococcal Bacteriocin Operons 57:492-498.
75. Bolotin, A., P. Wincker, and S. Mauger. 2001. The complete genome sequence of the lactic acid bacterium *Lactococcus lactis* ssp. *lactis* IL1403. Genome Reseach 731-753.
76. Broadbent, J. R., and J. K. Kondo. 1991. Genetic construction of nisin-producing *Lactococcus lactis* subsp. *cremoris* and analysis of a rapid method for conjugation. Appl. Environ. Microbiol. 57:517-524.
77. Campelo, A. B., C. Roces, M. L. Mohedano, P. Lopez, A. Rodriguez, and B. Martinez. 2014. A bacteriocin gene cluster able to enhance plasmid maintenance in *Lactococcus lactis*. Microb. Cell Fact. 13:77.
78. Carver, T., S. R. Harris, M. Berriman, J. Parkhill, and J. a McQuillan. 2012. Artemis: an integrated platform for visualization and analysis of high-throughput sequence-based experimental data. Bioinformatics 28:464-9.
79. Casey, J., C. Daly, and G. F. Fitzgerald. 1991. Chromosomal integration of plasmid DNA by homologous recombination in *Enterococcus faecalis* and *Lactococcus lactis* subsp. *lactis* hosts harboring Tn919. Appl. Environ. Microbiol. 57:2677-2682.
80. Clarke, M., L. Maddera, R. L. Harris, and P. M. Silverman. 2008. F-pili dynamics by live-cell imaging. Proc. Natl. Acad. Sci. U.S.A 105:17978-17981.
81. Coakley, A. D., G. F. Fitzgerald, and R. P. Ross. 1997. Application and Evaluation of the Phage Resistance- and Bacteriocin-Encoding Plasmid pMRC01 for the Improvement of Dairy Starter Cultures 63:1434-1440.
82. Cozzi, R., A. Nuccitelli, M. D'Onofrio, F. Necchi, R. Rosini, F. Zerbini, M. Biagini, N. Norais, C. Beier, J. L. Telford, G. Grandi, M. Assfalg, M. Zacharias, D. Maione, and C. D. Rinaudo. 2012. New insights into the role of the glutamic acid of the E-box motif in group B *Streptococcus* pilus 2a assembly. FASEB J. 26:2008-18.
83. Cui, Y., T. Hu, X. Qu, L. Zhang, Z. Ding, and A. Dong. 2015. Plasmids from Food Lactic Acid Bacteria: Diversity, Similarity, and New Developments. Int. J. Mol. Sci. 16:13172-13202.
84. Dai, G., N. W. Dunn, G. E. Allison, K. L. Jury, P. Su, and P. Zhu. 2000. Improvement of plasmid encoded lactococcal bacteriophage resistance by mutator strain Epicurian coli XL1-Red 721-725.

85. Davey, G. P. 1984. Plasmid Associated with Diplococcin Production in *Streptococcus cremoris* 48:895-896.
86. Davies, F. L., H. M. Underwood, and M. J. Gasson. 1981. The Value of Plasmid Profiles for Strain Identification in Lactic Streptococci and the Relationship between Streptoccocus *lactis* 712, ML3 and C2. J. Appl. Microbiol. 51:325-337.
87. De Jong, A., H. Pietersma, M. Cordes, 0. P. Kuipers, and J. Kok. 2012. PePPER: a webserver for prediction of prokaryote promoter elements and regulons. BMC Genomics 13:299.
88. De Vos, W. 1987. Gene cloning and expression in lactic streptococci. FEMS Microbiol. Lett. 46:281-295.
89. Douillard, F. P. P., P. Rasinkangas, I. von Ossowski, J. Reunanen, A. Palva, and W. M. M. de Vos. 2014. Functional Identification of Conserved Residues Involved in *Lactobacillus rhamnosus* Strain GG Sortase Specificity and Pilus Biogenesis. J. Biol. Chem. 289:15764-15775.
90. Duan, K., C. Q. Liu, Y. J. Liu, J. Ren, and N. W. Dunn. 1999. Nucleotide sequence and thermostability of pND324, a 3.6-kb plasmid from *Lactococcus lactis*. Appl. Microbiol. Biotechnol. 53:36-42.
91. Efstathiou, J., and L. McKay. 1977. Inorganic salts resistance associated with a lactose-fermenting plasmid in *Streptococcus lactis*. J. Bacteriol. 130:257-265.
92. Eij sink, V. G. H., L. Axelsson, D. B. Diep, L. S. Havarstein, H. Holo, and I. F. Nes. 2002. Production of class II bacteriocins by lactic acid bacteria; an example of biological warfare and communication 639-654.
93. Fallico, V., R. P. Ross, G. F. Fitzgerald, and O. McAuliffe. 2012. Novel conjugative plasmids from the natural isolate *Lactococcus lactis* subspecies *cremoris DPC*3758: a repository of genes for the potential improvement of dairy starters. J. Dairy Sci. Elsevier 95:3593-608.
94. Filloux, A. 2010. A variety of bacterial pili involved in horizontal gene transfer. J. Bacteriol. 192:3243-5.
95. Gasson, M. J. 1983. Plasmid complements of *Streptococcus lactis* NCDO 712 and other lactic streptococci after protoplast-induced curing. J. Bacteriol. 154:1-9.
96. Gasson, M. J., and F. L. Davies. 1980. High-frequency conjugation associated with *Streptococcus lactis* donor cell aggregation. J. Bacteriol. 143:1260-1264.
97. Gasson, M. J., S. Swindell, S. Maeda, and H. M. Dodd. 1992. Molecular rearrangement of lactose plasmid DNA associated with high-frequency transfer and cell aggregation in *Lactococcus lactis* 712. Mol. Microbiol. 6:3213-23.
98. Gevers, D., G. Huys, and J. Swings. 2003. In vitro conjugal transfer of tetracycline resistance from *Lactobacillus* isolates to other Gram-positive bacteria. FEMS Microbiol. Lett. 225:125-130.
99. Godon, J. J., K. Jury, C. A. Shearman, and M. J. Gasson. 1994. The *Lactococcus lactis* sex-factor aggregation gene cluA. Mol. Microbiol. Wiley Online Library 12:655-63.
100. Górecki, R. K., A. Koryszewska-Bagińska, M. Golebiewski, J. Żylińska, M. Grynberg, and J. K. Bardowski. 2011. Adaptative Potential of the *Lactococcus Lactis* IL594 Strain Encoded in Its 7 Plasmids. PLoS One 6:e22238.
101. Grohmann, E., G. Muth, and M. Espinosa. 2003. Conjugative plasmid transfer in gram-positive bacteria. Microbiol. Mol . . . 67:277-301.
102. Holo, H., and I. F. Nes. 1989. High-Frequency Transformation, by Electroporation, of *Lactococcus lactis* subsp. *cremoris* Grown with Glycine in Osmotically Stabilized Media 55:3119-3123.
103. Ingham, C. J., M. van den Ende, P. C. Wever, and P. M. Schneeberger. 2006. Rapid antibiotic sensitivity testing and trimethoprim-mediated filamentation of clinical isolates of the Enterobacteriaceae assayed on a novel porous culture support. J. Med. Microbiol. 55:1511-9.
104. Jack, R. W., J. R. Tagg, and B. Ray. 1995. Bacteriocins of Gram-Positive Bacteria. Microbiol. Rev. 59:171-200.
105. Kankainen, M., L. Paulin, S. Tynkkynen, I. von Ossowski, J. Reunanen, P. Partanen, R. Satokari, S. Vesterlund, A. P. a Hendrickx, S. Lebeer, S. C. J. De Keersmaecker, J. Vanderleyden, T. Hamalainen, S. Laukkanen, N. Salovuori, J. Ritari, E. Alatalo, R. Korpela, T. Mattila-Sandholm, A. Lassig, K. Hatakka, K. T. Kinnunen, H. Karjalainen, M. Saxelin, K. Laakso, A. Surakka, A. Palva, T. Salusjarvi, P. Auvinen, and W. M. de Vos. 2009. Comparative genomic analysis of *Lactobacillus rhamnosus* GG reveals pili containing a human-mucus binding protein. Proc. Natl. Acad. Sci. U.S.A 106:17193-8.
106. Khunajakr, N., C. Liu, P. Charoenchai, and N. Dunn. 1999. A plasmid-encoded two-component regulatory system involved in copper-inducible transcription in *Lactococcus lactis*. Gene 229:229-235.
107. Klaenhammer, T. R., and R. B. Sanozky. 1985. Conjugal transfer from *Streptococcus lactis* ME2 of plasmids encoding phage resistance, nisin resistance and lactose-fermenting ability: evidence for a high-frequency conjugative plasmid responsible for abortive infection of virulent bacteriophage. J. Gen. Microbiol. 131:1531-41.
108. Kline, K., K. Dodson, M. Caparon, and S. Hultgren. 2010. A tale of two pili: assembly and function of pili in bacteria. Trends Microbiol. 18:224-232.
109. Kojic, M., B. Jovcic, I. Strahinic, J. Begovic, J. Lozo, K. Veljovic, and L. Topisirovic. 2011. Cloning and expression of a novel lactococcal aggregation factor from *Lactococcus lactis* subsp. *lactis* BGKP1. BMC Microbiol. 11:265.
110. Kojic, M., I. Strahinic, and L. Topisirovic. 2005. Proteinase PI and lactococcin A genes are located on the largest plasmid in *Lactococcus lactis* subsp. *lactis* bv. diacetylactis S50 314:305-314.
111. Kok, J., J. M. van der Vossen, and G. Venema. 1984. Construction of plasmid cloning vectors for lactic streptococci which also replicate in *Bacillus subtilis* and *Escherichia coli*. Appl. Environ . . . .48:726-731.
112. Kuipers, 0. P., P. G. G. a De Ruyter, M. Kleerebezem, and W. M. De Vos. 1997. Controlled overproduction of proteins by lactic acid bacteria. Trends Biotechnol. 15:135-140.
113. Kumar, P., S. Henikoff, and P. C. Ng. 2009. Predicting the effects of coding non-synonymous variants on protein function using the SIFT algorithm. Nat. Protoc. 4:1073-1081.
114. Le Bourgeois, P., M. L. Daveran-Mingot, and P. Ritzenthaler. 2000. Genome plasticity among related *Lactococcus* strains: Identification of genetic events associated with macrorestriction polymorphisms. J. Bacteriol. 182:2481-2491.
115. Le, D. T. L., T. L. Tran, M. P. Duviau, M. Meyrand, Y. Guerardel, M. Castelain, P. Loubiere, M. P. Chapot-Chartier, E. Dague, and M. Mercier-Bonin. 2013. Unraveling the role of surface mucus-binding protein and pili in muco-adhesion of *Lactococcus lactis*. PLoS One 8:e79850.
116. Leenhouts, K. J., J. Kok, and G. Venema. 1991. Lactococcal plasmid pWVO1 as an integration vector for lactococci. Appl. Environ. Microbiol. 57:2562-2567.

117. Lelie, D. Van der, and F. Chavarri. 1991. Identification of a new genetic determinant for cell aggregation associated with lactose plasmid transfer in *Lactococcus lactis*. Appl . . . 57.
118. Linares, D. M., J. Kok, and B. Poolman. 2010. Genome sequences of *Lactococcus lactis* MG1363 (revised) and NZ9000 and comparative physiological studies. J. Bacteriol. 192:5806-12.
119. Liu, C., P. Charoechai, and N. Khunajakr. 2002. Genetic and transcriptional analysis of a novel plasmid-encoded copper resistance operon from *Lactococcus lactis*. Gene 297:241-247.
120. Maisnier-patin, S., and J. Richard. 1996. Cell wall changes in nisin-resistant variants of *Listeria innocua* grown in the presence of high nisin concentrations 97.
121. Mandlik, A., A. Swierczynski, A. Das, and H. Ton-That. 2008. Pili in Gram-positive bacteria: assembly, involvement in colonization and biofilm development. Trends Microbiol. 16:33-40.
122. Marraffini, L., A. C. DeDent, and O. Schneewind. 2006. Sortases and the art of anchoring proteins to the envelopes of gram-positive bacteria. Microbiol. Mol. Biol. Rev. 70:192-221.
123. McClure, R., D. Balasubramanian, Y. Sun, M. Bobrovskyy, P. Sumby, C. a. Genco, C. K. Vanderpool, and B. Tjaden. 2013. Computational analysis of bacterial RNA-Seq data. Nucleic Acids Res. 41:1-16.
124. McKay, L. L., K. a. Baldwin, and P. M. Walsh. 1980. Conjugal transfer of genetic information in group N streptococci. Appl. Environ. Microbiol. 40:84-91.
125. Meyrand, M., A. Guillot, M. Goin, S. Furlan, J. Armalyte, S. Kulakauskas, N. G. Cortes-Perez, G. Thomas, S. Chat, C. Péchoux, V. Dupres, P. Hols, Y. F. Dufrêne, G. Trugnan, and M.-P. Chapot-Chartier. 2013. Surface proteome analysis of a natural isolate of *Lactococcus lactis* reveals the presence of pili able to bind human intestinal epithelial cells. Mol. Cell. Proteomics 12:3935-47.
126. Mierau, I., and M. Kleerebezem. 2005. 10 years of the nisin-controlled gene expression system (NICE) in *Lactococcus lactis*. Appl. Microbiol. Biotechnol. 68:705-17.
127. Mierau, I., P. Leij, I. van Swam, B. Blommestein, E. Floris, J. Mond, and E. J. Smid. 2005. Industrial-scale production and purification of a heterologous protein in *Lactococcus lactis* using the nisin-controlled gene expression system NICE: the case of lysostaphin. Microb. Cell Fact. 4:15.
128. Millen, A. M., P. Horvath, P. Boyaval, and D. a Romero. 2012. Mobile CRISPR/Cas-mediated bacteriophage resistance in *Lactococcus lactis*. PLoS One 7:e51663.
129. Mills, S., 0. E. McAuliffe, A. Coffey, G. F. Fitzgerald, and R. P. Ross. 2006. Plasmids of lactococci—genetic accessories or genetic necessities? FEMS Microbiol. Rev. 30:243-73.
130. O'Driscoll, J., F. Glynn, G. F. Fitzgerald, and D. van Sinderen. 2006. Sequence analysis of the lactococcal plasmid pNP40: a mobile replicon for coping with environmental hazards. J. Bacteriol. 188:6629-39.
131. Ojala, V., J. Laitalainen, and M. Jalasvuori. 2013. Fight evolution with evolution: plasmid-dependent phages with a wide host range prevent the spread of antibiotic resistance. Evol. Appl. 6:925-32.
132. Oxaran, V., F. Ledue-Clier, Y. Dieye, J.-M. Herry, C. Péchoux, T. Meylheuc, R. Briandet, V. Juillard, and J.-C. Piard. 2012. Pilus biogenesis in *Lactococcus lactis*: molecular characterization and role in aggregation and biofilm formation. PLoS One 7:1-18.
133. Proft, T., and E. N. Baker. 2009. Pili in Gram-negative and Gram-positive bacteria-structure, assembly and their role in disease. Cell. Mol. Life Sci. 66:613-35.
134. Reunanen, J., I. von Ossowski, A. P. a Hendrickx, A. Palva, and W. M. de Vos. 2012. Characterization of the SpaCBA pilus fibers in the probiotic *Lactobacillus rhamnosus* GG. Appl. Environ. Microbiol. 78:2337-44.
135. Rintahaka, J., X. Yu, R. Kant, A. Palva, and I. von Ossowski. 2014. Phenotypical analysis of the *Lactobacillus rhamnosus* GG fimbrial spaFED operon: surface expression and functional characterization of recombinant SpaFED pili in *Lactococcus lactis*. PLoS One 9:e113922.
136. Russell, J. B. 2001. Nisin Resistance of *Streptococcus bovis* 67:808-813.
137. Rutherford, K., J. Parkhill, J. Crook, T. Horsnell, and P. Rice. 2000. Artemis: sequence visualization and annotation 16:944-945.
138. Ruyter, P. De, O. Kuipers, and W. de Vos. 1996. Controlled gene expression systems for *Lactococcus lactis* with the food-grade inducer nisin. Appl. . . . 62:3662-3667.
139. Salminen, S., A. Von Wright, and A. Ouwehand. 2004. Lactic acid bacteria: microbiology and functional aspects.
140. Sambrook, J., E. F. Fritsch, and T. Maniatis. 1989. Molecular cloning: a laboratory manual. Cold Spring Habor Laboratory press.
141. Schaberg, D. R., and M. J. Zervos. 1986. Intergeneric and interspecies gene exchange in gram-positive cocci. Antimicrob. Agents Chemother. 30:817-822.
142. Scott, J. R., and D. Zahner. 2006. Pili with strong attachments: Gram-positive bacteria do it differently. Mol. Microbiol. 62:320-30.
143. Siezen, R., and B. Renckens. 2005. Complete sequences of four plasmids of *Lactococcus lactis* subsp. *cremoris* SK11 reveal extensive adaptation to the dairy environment. Appl. Environ. Microbiol. 71:8370-8383.
144. Sim, N.-L., P. Kumar, J Hu, S. Henikoff, G. Schneider, and P. C. Ng. 2012. SIFT web server: predicting effects of amino acid substitutions on proteins. Nucleic Acids Res. 40:W452-7.
145. Simon, D., and A. Chopin. 1988. Construction of a vector plasnfid family and its use for molecular cloning in *Streptococcus lactis* 70:559-566.
146. Sing, W. D., and T. R. Klaenhammer 1991. Characterization of Restriction-Modification Plasmids from *Lactococcus lactis* ssp. *cremoris* and Their Effects When Combined with pTR2030. J. Dairy Sci. Elsevier 74:1133-1144.
147. Steele, J. L., and L. L. McKay. 1986. Partial characterization of the genetic basis for sucrose metabolism and nisin production in *Streptococcus lactis*. Appl. Environ. Microbiol. 51:57-64.
148. Stentz, R., K. Jury, T. Eaton, M. Parker, A. Narbad, M. Gasson, and C. Shearman. 2004. Controlled expression of CluA in *Lactococcus lactis* and its role in conjugation. Microbiology 150:2503-12.
149. Sterkenburg, A., P. V. A. N. Leeuwen, and J. T. M. Wouters. 1988. Loss of phage resistance encoded by plasmid pSK112 in chemos-tat cultures of *Lactococcus lactis* ssp. *cremoris* SKI 10 70:451-456.
150. Taguchi, F., and Y. Ichinose. 2011. Role of type IV pili in virulence of *Pseudomonas syringae* pv. *tabaci* 6605: correlation of motility, multidrug resistance, and HR-inducing activity on a nonhost plant. Mol. Plant. Microbe. Interact. 24:1001-1011.
151. Telford, J. L., M. a Barocchi, I. Margarit, R. Rappuoli, and G. Grandi. 2006. Pili in gram-positive pathogens. Nat. Rev. Microbiol. 4:509-19.

152. Ton-That, H., L. a Marraffini, and O. Schneewind. 2004. Protein sorting to the cell wall envelope of Gram-positive bacteria. Biochim Biophys. Acta 1694:269-78.
153. Ton-That, H., L. a Marraffini, and O. Schneewind. 2004. Sortases and pilin elements involved in pilus assembly of *Corynebacterium diphtheriae*. Mol. Microbiol. 53:251-261.
154. Ton-That, H., and O. Schneewind. 2004. Assembly of pili in Gram-positive bacteria. Trends Microbiol. 12:228-234.
155. Tripathi, P., A. Beaussart, G. Andre, T. Rolain, S. Lebeer, J. Vanderleyden, P. Hols, and Y. F. Dufrene. 2012. Towards a nanoscale view of lactic acid bacteria. Micron. Elsevier Ltd 1-8.
156. Van der Meer, J. R., J. Polman, M. M. Beerthuyzen, R. J. Siezen, 0. P. Kuipers, and W. M. De Vos. 1993. Characterization of the *Lactococcus lactis* nisin A operon genes nisP, encoding a subtilisin-like serine protease involved in precursor processing, and nisR, encoding a regulatory protein involved in nisin biosynthesis. J. Bacteriol. 175:2578-88.
157. Von Ossowski, I., J. Reunanen, R. Satokari, S. Vesterlund, M. Kankainen, H. Huhtinen, S. Tynkkynen, S. Salminen, W. M. de Vos, and A. Palva. 2010. Mucosal adhesion properties of the probiotic *Lactobacillus rhamnosus* GG SpaCBA and SpaFED pilin subunits. Appl. Environ. Microbiol. 76:2049-57.
158. Walsh, P. M., and L. L. McKay. 1981. Recombinant plasmid associated with cell aggregation and high-frequency conjugation of *Streptococcus lactis* ML3. J. Bacteriol. 146:937-944.
159. Wegmann, U., M. O'Connell-Motherway, A. Zomer, G. Buist, C. Shearman, C. Canchaya, M. Ventura, A. Goesmann, M. J. Gasson, 0. P. Kuipers, D. Van Sinderen, and J. Kok. 2007. Complete genome sequence of the prototype lactic acid bacterium *Lactococcus lactis* subsp. *cremoris* MG1363. J. Bacteriol. 189:3256-3270.
160. Wegmann, U., K. Overweg, S. Jeanson, M. Gasson, and C. Shearman. 2012. Molecular characterization and structural instability of the industrially important composite metabolic plasmid pLP712. Microbiology 158:2936-45.
161. Wells, J. M., P. W. Wilson, and R. W. Le Page. 1993. Improved cloning vectors and transformation procedure for *Lactococcus lactis*. J. Appl. Bacteriol. 74:629-636.
162. Zerbino, D. R. 2011. Using the Velvet de novo assembler for short-read sequencing technologies. Curr. Protoc. Bioinforma. 1-13.
163. Zerbino, D. R., and E. Birney. 2008. Velvet: algorithms for de novo short read assembly using de Bruijn graphs. Genome Res. 18:821-9.

The invention claimed is:

1. A dairy bacterial strain with clumping and/or chaining properties when cultured under liquid conditions, wherein the clumping property results in clumps of at least 20 bacteria per average clump, and wherein the chaining property results in chains of at least 8 bacteria per average chain, and wherein the strain comprises an increased amount of expression product of a pilin gene cluster compared to that of *Lactococcus lactis* subsp. *cremoris* NCDO712 when cultured under identical conditions.

2. The dairy bacterial strain according to claim 1, wherein the pilin gene cluster has a nucleotide sequence that has at least 30% sequence identity with SEQ ID NO: 1.

3. The dairy bacterial strain according to claim 1, wherein the dairy bacterial strain is a lactic acid bacterial strain.

4. The dairy bacterial strain according to claim 3, which is a *Lactococcus* strain.

5. The dairy bacterial strain according to claim 4, which is a *Lactococcus lactis* strain, a *Lactococcus lactis* subsp. *lactis* strain, or a *Lactococcus lactis* subsp. *cremoris* strain.

6. The dairy bacterial strain according to claim 1, having at least one property selected from the group consisting of capacity to texturize milk, capacity to increase viscosity when cultured in milk, capacity to increase stress to shearing when cultured in milk and capacity to increase the fraction of bacteria that remain in curd during cheese making.

7. The dairy bacterial strain according to claim 1 which does not comprise a clumping agent.

8. A composition comprising a dairy bacterial strain according to claim 1.

9. The composition according to claim 8, further comprising another dairy bacterial strain (within the same composition or separate as a kit of parts), optionally a *Streptococcus thermophilus* and/or a *Lactobacillus* species.

10. The composition according to claim 8 which is in a freeze dried, frozen or liquid suspension state.

11. A method for production of the dairy bacterial strain according to claim 1, comprising culturing a precursor dairy bacterial strain under conditions that are conducive to the development of clumping and/or chaining properties and, optionally, isolating the dairy bacterial strain.

12. The method according to claim 11, comprising mutating the dairy bacterial strain, optionally by chemical treatment, radiation treatment and/or recombinant treatment.

13. A dairy bacterial strain produced by the method according to claim 11.

14. A method for production of a dairy food product from a precursor food product which method comprises inoculating the precursor food product with a strain according to claim 1 or with a composition thereof and incubating the inoculated precursor food product.

15. The method according to claim 14, further comprising adding an ingredient selected from the group consisting of a flavoring agent, a fruit or fruit concentrate, a syrup, a prebiotic, a bacterial strain, optionally a probiotic, a coloring agent, a thickening agent, a preserving agent, and an enzyme.

* * * * *

SEQUENCE LISTING

<160> NUMBER OF SEQ ID NOS: 6

<210> SEQ ID NO 1
<211> LENGTH: 7714
<212> TYPE: DNA
<213> ORGANISM: Lactococcus lactis

<400> SEQUENCE: 1

```
atgaagaaaa agtgggcgac ttggctcagc cttttggtac tatgtttgag tatagtagca        60
aatattagcc aaggatacac agtattagca gattcatcta attcactaac ctcaggggat       120
ccaaccacag cagatccatt taattatata aaaaatggtg atgtggctta tccaaaacaa       180
ggcacatcaa cttatcaaaa tggcaaaaca gatgaagata tcgtaaacta tgatttttca       240
caatcaagca gtgaaggcca gtctagcata aaaaatattt tcggaagtgg ggcacttact       300
tttgataacg gctatcatta ttatcaaaat gatgggtatg ttaagaagat agttatgcct       360
actaatgatc ccacccaatt taaagtccgt ttagatatga taggtgagga gttaaaaaca       420
accaaacctg ttgacatcgc catggtatta gataattcaa cgtcaatgaa ttatgatatg       480
ggagcaggga agacaagatg gcagactttg aaagactctg ttaaaaattt tgctaaccaa       540
ttaattggtc catcttcaaa taataatgat aatgtaagaa taggctttc aagtttggt        600 tctgagcggc aaaggattag tatttggcca ggttattctg atataccatt tacaaaaatt       660
ggtaaatttt catcaaactc atcttttacc tctaactata ctcagttatt gaattcaagt       720
atttatactc ctacagcagc accaaggctt tctggtaccc cgacattttt aggtgtagat       780
gcaggatata agatgttgtc agatgctaca tatggtgcac gttctgattc agtaaaagta       840
ttgattgttc taacagatgg agaaccgaca ttttggaatt caggatccta cactagctta       900
agtaatgtgg gatcaacgac taattatgat tatttttcaa ctccgtatta ttctggtaat       960
ggagtgaaat ctgaatctaa ttatacgagt acaataaatt ttgtcaatca aagagccaat      1020
gcgaatccag gagtatcaaa gtattcgatt ggtatttcta cagttaataa cagtggcata      1080
aaatcagtct taaaggcgct aggaccagat ggtacttttg aagcgtcaaa tcaacaagat      1140
```

```
ctagtggatg ctttagacaa aattaggacg tcgattagta agtctattca aaaaggctca   1200
ttgattgacc ctatgagtca gtatgtcacg ttaaatacga acagcataca gacatatgat   1260
ttgaaagttg atagtaatag tatatcagcg acaggctcaa atcgtagtgt taaaactgat   1320
aataaccaaa tctctattga taatttaagt attggtaaaa atgaaggagt acgtgtagag   1380
tatacagtct ccttaaaaca acaatattgg gatggacagt ttcatccagc taacggcaca   1440
acttatttac aaaataataa gttatcacca gctcaatatc ttcattttgc agttccatcc   1500
attaagtatg atacttttaa tctaccagtt caaaaaattt gggatgatca aaataaccag   1560
tatcaaacga gacaagatat tatcttacaa ctacaatctt ttgtgaacaa tacatggcaa   1620
aatgtatctg ataagacatt tgccattaag gcaagtgcga cagatgatca actcaaaggt   1680
gttatttctg gtattccatc caaggatggt gcaaatcaac caattaaata tcgacttgtt   1740
gagttgtttg gaaatactga gcaagcagtt aatggttatg ctacaccaag ttattcaacg   1800
ccaagggaaa taacatatac agatatagtt aatggtaatg tgtctaaaga caagccgtta   1860
gctgtaacaa atacattatt aaaaacagct attagtttta caaaagttgg taatgataat   1920
cagactcctt tagcaggagc tgagtttacc ctttatgcct ctgatggaaa aacacaaatt   1980
ggatcgccag tcacgtctga taaaaatggc ctagttaaat tcgatcaaca agtaccaatt   2040
gggaaatact aatcaaaga aactaaaaca ccacttggtt atgtcaaagc ttctgatatt   2100
aatatttcgg taactgctca aaatggacaa cttgtcattt caggtttgcc aactggcagt   2160
aaggttaaaa atatattaga tgatttcaaa ttaattatca ctaaaaaaga taataatggc   2220
aatgctgtat ctggtgttaa atttaaactt gttggttcaa ataattataa taaggaacaa   2280
gaatctgatg ctagtaatgg aaatgtattt acttttcaag ggttaaaacc aggcaagtat   2340
gcattaactg agactaaaac accagaaaaa tatgttggtc taaaacaaga tgtgatcatt   2400
ttgattgggg acgatggtaa agtcactatt gatggacagc cgctacctga tcaaccaatt   2460
accacaactg gtaatatcat taagcttgat gtgacgaata cgataaaagg tattctccct   2520
agtacaggtg gctctggtcg gacaggctat tttatagcga gtcttatctt tatgggatta   2580
gttgcgatta tcggtggtat cttctactat cgtaatagac gtctacgtca tcataaactt   2640
cttaaaggtc cacataacaa aagtcatctg ttactgttgc tgttaatcac gtctctggga   2700 ataacccttta caaatgctca gaaaatagca gcagatgaac aaccgattac ctttatctta   2760
cataaacgtg tctttaaaga tagtggagac ttaaaaacaa ttaaagataa tgggttagtg   2820
attacaccta atgatcccaa ttcaggtgtg attgattcgg ataaaacata tgggttgaat   2880
ggtgtcactt tcgatgttta tgatgtcact agttatgtgt caaatgcttt aaaaagtaca   2940
tctaaagagg cgcttatgaa acacgtcaca aatactgata aggctagcct attggccgaa   3000
ataaagccat atcagccaac aagtcaggaa gttgtgacgg tttcaagcga tggagatgat   3060
ggtgttgcac gatttagtgt tcaacctact tctcaaaaca gtgcttatct gatactggag   3120
aagcagatct ctgacaaaga tgctggtaaa gtcaagatga cggcaacacc gatgttggtt   3180
atattaccag tagcgaatcc tgttgataaa acatcatttt tgacaacgat aaatctgtat   3240
cctaaaaata cagcagtcaa aacaccagtt atcccaccag taaacccggt aaatccgaaa   3300
ccacctcatt tccctttttt acctgataca ggtgaagtta agtcggtaat ggttgttttg   3360
ggtggcattg tcgtaatcat agcagttagc ttttggtata accgacgtaa gccaaagccg   3420
tcataaacta aagtctttgt caattattgt caagcttata tagaaaattt tggagaaaaa   3480
```

```
tatgaaaaca aacaaattct tacaagtgat tttagcaaca attttgttgt taacaaccgc    3540
ttttgtgtca aatcagcata ttatttagta ataataagga aaaattaaga tgatctttta    3600
tagattgatt ttgaaaggag atagggacac accttaaaac gaagcacagt gtaaaaatca    3660
ctcactcaaa aatggagaat aaaatgaaaa aagaaaaatt attaaaatta gtaatgacgt    3720
tattgctagc gttgatagct attgttgccc caatttcatc tgcttttgcg gatgacacaa    3780
ttgatgactc tacaaaggtt aatgtgacct taaataaact gatttggaat gataatgcac    3840
caactgattt ccaaaataca ggtgcaaaaa tgaactttga cggttcagct acaccattaa    3900
atggatctga atttacgctt tatgatgtta caagtcaata ttataactat attgctaata    3960
agagccaaca agcagccatt agccaaattc aagcagacgc aagtcaagtt gctccaaatt    4020
atgcaaaaaa cattaaatca gttaccactg ctgggcaagg acaggcttta ttcaatgatt    4080
tgtcagtaaa gaataaatca ggacaatata acgtttatct tttccttgaa actaaaaccc    4140
ctgacaatat tacagttaca aaattgtcag ctcctattgt gttggcaatg ccgatttaca    4200
ctttagataa acaacaacaa cctactgaca cactaaatca agacattcaa ctttatccta    4260
aaaacgttac atctaaagat acaaaagaat ttacaaatgt tggatcattt agtaaggtaa    4320
ctgttggaga tcagtctttt gctaatgtga caacaggcga tgttttaaac tatactttga    4380
ccgttaacat tcctgctaat attggtgatg caaatgctgt taataaatat tcgattttg     4440
ataaaccatc tgatggactt gcactcgtta acaatacagt tactgtggga agtttgactg    4500
cgggaaatgg aacttcagag gattatgata ttgcttatgt aaatggtgga ttcacggtta    4560
atttacatct gaacagtgat aatgttaaag cattggctgg taaaaaaata caattaactt    4620
ataatatgaa attgacggca gatgtgaatc cggataattt acaaagtaac aaagcgagtg    4680
tccaaattaa taattcgcct gaacaacaaa tcacccctcc aactcctgta ggtactggtg    4740
gttacaaatt tatcaaaaag gatgctcaaa ctggaaaaaa cttatctggg gcagagtttg    4800
tcgtggctaa tagtgataaa tcaaaatttg caaaatttag tggtcaaaac tcaaaaagtg    4860
aatatgtatt tgattcatgg gtctcaaaag atcaagcaac aaaaattgtt tccggaaatg    4920
atggatcatt caatgtaatc ggacttacaa atgggaatta cgtacttaat gaaactaaag    4980
caccttcagc taactatgtt ctcttaaaag atggtacaat tacatttaca gttgtacatg    5040
gtaaatatgt cacatcaaac ttagatgtta agaatacacc taaagggcta ttgccatcaa    5100
ctggtggtgc tggtatctac gccttcatca ttattggtgc agcaatgatg attggtgcat    5160
atatttggtt taaaaaatca agacaacaag cagaagttta agtctttaga ctaacaggtt    5220
ttttcctgaa gttaaaggtt aacgttaaca aggctgggga actttcccag ccttgttgtg    5280
tttcggaaag gaaggtgtat cagcattgaa aaaacaatac ccgcagcaag ataacttaaa    5340
aaacgaaaga atcaatttat ggcttaaggt tttgatggcg cttttgttct tgcaggtgc     5400
aatggtattt tcctacccct ttgttgtcga tacaatcaat aatttttatg atcaacgtgt    5460
gattgataac tatcaaatcc aatatcaaac agcacataaa gcgcaacaaa aaaaacagtt    5520
ggcccagatg aaagcagaaa atgaatcctt gctcaaacaa gagcatacga caaacattcc    5580
tggcatgggc ttagttgaag atccgtttga aagtgcacta aaaaataatg tgaaaccaag    5640
caaagcttat ttgcaatctc atatgatagg tgccatttt attccttcta tccatgttag    5700
tttacctatt tttaatgaaa ctaacgacga gttattagaa aaaggcgcta cagtattaca    5760
ggggacttct tatccgatag gtggtatcag tacacattca gttttgactg gcacagtgg     5820
tctaccagat aaaaaactct ttacggattt ggataaactg aaaaaaggtg acttatttta    5880
```

-continued

```
tattgaagta ttgggtgaga aattagctta tcgtgcagtt aactttaaaa cggtattacc      5940
aacacaacta gagagtttaa agatagtgga tggcaaagat ttagtcactt tagtgacttg      6000
taccccttat atggttaata cgcatcgttt attagtcacg ggagaacgtg ttccttttgt      6060
cgaacaaaag atgaccaagc aaatcaaaaa agcacaagcc tatcatcaga atagactact      6120
cgcttttgca gtcggtattc cgattttctg tttattattt gcatatttta tatggcgcaa      6180
gtttgtctat tatctgtgta tcaaacatcg ctatgatttt gtattctacg ctgtagctaa      6240
tggacaagga atagctaatt tagccttttta tctgatagag aaaaagggga aaataccagt      6300
attaagagac ggtgaacggc ttaaagcaat cagtgataaa gatgggcgtg tcctgtttga      6360
agatatccca ggtggccgct atgttgctta tcctgatgag caaaccgctt ttccaaaagt      6420
atctggattt gtgcgactgt tacaggatca acactttaca cttaagtctc atggtgcacg      6480
cgtaaaaaga accggtaagc aacaccatcg tgactatatc attgatacgg gacatcatgc      6540
gaaataaaaa caagccacaa ggaaaggcta aaaaagcat aggcaagcgt ttttttgatta      6600 atttgatggt ttatagttta ttttgattg gtatattgat catgctatat ccgttttata      6660
tcagtgcctt aaatgactac ttagataatg ttcgcgtgtc gctttataag gatagtttac      6720
aaaaagctca cgacacacaa gaaaagcagt tgaaagcagc taatgaaaaa ttagctaaac      6780
aaggcttgac accctctaaa gatccttta aagatgacaa agcaagtggt gtttctgaag      6840
attattataa aaaacatcta ctaggcacca ttgatattcc taagatcaac attaaaatcc      6900
cactatttga tacgactaat agtgaactgt tagaaattgg tgcaacaacc ttaaatggga      6960
cctcataccc attaggaggt caaaatacac acgctgtgat tgcggctcat cgagggctac      7020
cagaccgtgc acttttttact gatttaccaa aactaaaaga aggggatatc tttgttttag      7080
aagtattggg tcataagtta gcctatgagg tgaagacgat tgttgtggtg aaaccagaag      7140
aaacacaggt cttaaagata gagccagggc aagactggt gacgttattg acttgtacac      7200
cttatatgat caactctcat cgcttactag taactggcag tcgtgtccct tatacgccca      7260
aagttgaaaa gatgttagcg caaaatgacc ataatcgcaa actgatccaa cttgctttgc      7320
tagtcttatt taccttacta gtttgcttaa tgctctggat actttatcgt attatccacc      7380 aataccttgct cactaagcaa aatatgtcga ttatttttaca gattatcacc tcagatcaat      7440
cgccttacgc acaacctttta catctttatg atcgaacggg taaagagca ttgaagcgtc      7500 aaggtgaggc ggtgatatta ataccagatg cgacgggtac ttatcagatt gatcacttag      7560
caaaagggat gtattgttta aaaaccaaag atgatgcgct atgtgtgttg atcggacaaa      7620
ctaagataaa agcgatgact tatcaactta agtaatgaa aagatctaaa ttatcctta      7680 aacaactctc aaagcaagta attcaaatta ctta                                  7714
```

<210> SEQ ID NO 2
<211> LENGTH: 383
<212> TYPE: DNA
<213> ORGANISM: Lactococcus lactis

<400> SEQUENCE: 2

```
tttccatgaa taaaaggatt ttttatttt cttttccaa atttgatagt agatttaaaa       60
ctttgcaaca gaaccgtaat tgattagcaa aaatattttt ttcaaataag atagataaat     120
cagtgtaaaa tcgacaaata aggtcttgca ttttctatag aattgatata tagttaatta     180
gatcggcagt tactgatgaa acaggctata ccttgaaatg tactcgattt atcgagtatt     240
```

```
atgatataaa tctagatgat ataaattaaa aagttgagcg taataattgt tttgagtttc      300
caaccgaatt aagctgtttt cagatctttg atcggtgtca agatttgctt acatatatat      360
tttaagagaa aggggggacga tat                                              383

<210> SEQ ID NO 3
<211> LENGTH: 24
<212> TYPE: DNA
<213> ORGANISM: Artificial Sequence
<220> FEATURE:
<223> OTHER INFORMATION: PCR primer

<400> SEQUENCE: 3
ggaccagatg gtactttga agcg                                               24

<210> SEQ ID NO 4
<211> LENGTH: 26
<212> TYPE: DNA
<213> ORGANISM: Artificial Sequence
<220> FEATURE:
<223> OTHER INFORMATION: PCR primer

<400> SEQUENCE: 4
ggtaaagtca ctattgatgg acagcc                                            26

<210> SEQ ID NO 5
<211> LENGTH: 36
<212> TYPE: DNA
<213> ORGANISM: Artificial Sequence
<220> FEATURE:
<223> OTHER INFORMATION: PCR primer

<400> SEQUENCE: 5
ccgctgcagt ttgcaacaga accgtaattg attagc                                 36

<210> SEQ ID NO 6
<211> LENGTH: 50
<212> TYPE: DNA
<213> ORGANISM: Artificial Sequence
<220> FEATURE:
<223> OTHER INFORMATION: PCR primer

<400> SEQUENCE: 6
cggctcgagt taagtaattt gaattacttg ctttgagagt tgtttaaagg                   50
```